(12) United States Patent
Liu et al.

(10) Patent No.: US 10,934,286 B2
(45) Date of Patent: Mar. 2, 2021

(54) HETEROCYCLIC SULFONES AS ROR GAMMA MODULATORS

(71) Applicant: BRISTOL-MYERS SQUIBB COMPANY, Princeton, NJ (US)

(72) Inventors: Qingjie Liu, Newtown, PA (US); T. G. Murali Dhar, Newtown, PA (US); Lan-ying Qin, Plainsboro, NJ (US); Lyndon A. M. Cornelius, Jackson, NJ (US); Hai-Yun Xiao, Belle Mead, NJ (US); Jianqing Li, Guilford, CT (US); Robert J. Cherney, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/341,474

(22) PCT Filed: Oct. 12, 2017

(86) PCT No.: PCT/US2017/056257
§ 371 (c)(1),
(2) Date: Apr. 12, 2019

(87) PCT Pub. No.: WO2018/071620
PCT Pub. Date: Apr. 19, 2018

(65) Prior Publication Data
US 2019/0300523 A1  Oct. 3, 2019

Related U.S. Application Data

(60) Provisional application No. 62/407,702, filed on Oct. 13, 2016.

(51) Int. Cl.
*C07D 471/04* (2006.01)
*C07D 491/147* (2006.01)

(52) U.S. Cl.
CPC ....... *C07D 471/04* (2013.01); *C07D 491/147* (2013.01)

(58) Field of Classification Search
CPC .................. C07D 471/04; C07D 491/147
See application file for complete search history.

(56) References Cited

U.S. PATENT DOCUMENTS 10,273,259 B2 * 4/2019 Duan .................. A61P 17/06

FOREIGN PATENT DOCUMENTS

| EP | 2368886 A1 | 9/2011 |
|---|---|---|
| WO | WO2007084595 A2 | 7/2007 |
| WO | WO2015042212 A1 | 3/2015 |
| WO | WO2015103509 A1 | 7/2015 |
| WO | WO2016179460 A1 | 11/2016 |

OTHER PUBLICATIONS

Chang. Journal of Experimental Pharmacology, 2012, 4, 141-148 (Year: 2012).*
Schafer. Dermatology, 2006, 212, 327-337 (Year: 2006).*
U.S. Appl. No. 15/148,209, filed May 6, 2016, Granted U.S. Pat. No. 9,815,859.
U.S. Appl. No. 15/701,818, filed Sep. 12, 2017, Published US/20180002358A1.
PCT/US2017/055687, Filing Date: Oct. 9, 2017, Published WO2018/071314.
PCT/US2017/060501, Filing Date: Nov. 8, 2017, Published WO2018/089402.
International Search Report for Application No. PCT/US2017/056257, dated Dec. 18, 2017.

* cited by examiner

*Primary Examiner* — Noble E Jarrell
(74) *Attorney, Agent, or Firm* — Elliott Korsen

(57) ABSTRACT

There are described RORγ modulators of the formula (I), or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ Gamma activity in a cell and methods for treating a subject suffering from a disease or disorder in which the subject would therapeutically benefit from modulation of RORγ Gamma activity, for example, autoimmune and/or inflammatory disorders.

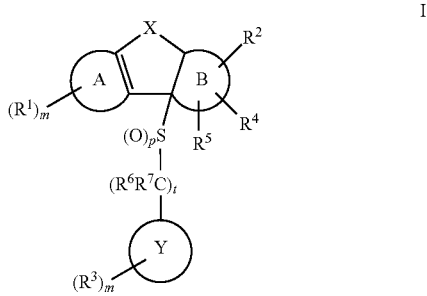

I

20 Claims, No Drawings

HETEROCYCLIC SULFONES AS ROR GAMMA MODULATORS

CROSS-REFERENCE TO RELATED APPLICATIONS

This application claims the benefit of U.S. Provisional Application No. 62/407,702, filed Oct. 13, 2016, the disclosure of which is incorporated herein by reference in its entirety.

FIELD OF THE INVENTION

This invention relates to modulators of the retinoid-related orphan receptor RORγ and methods for using said modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors, RORα, RORβ, and RORγ, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γ6 cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the Formula (I),

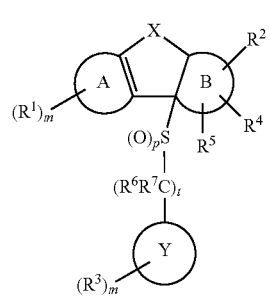

or pharmaceutically acceptable salts thereof, wherein all substituents are defined herein. The invention includes stereoisomers, tautomers, solvates, or prodrugs thereof.

In another aspect, the invention comprises pharmaceutical compositions comprising a compound according to Formula (I), stereoisomeric form or pharmaceutically acceptable salt, as described herein, and a pharmaceutically acceptable carrier, excipient, or diluent.

In another aspect, the invention comprises methods for modulating RORγ in a cell comprising contacting the cell with an effective amount of a compound according to Formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of a compound according to Formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of a compound according to Formula (I), or a stereoisomeric form, pharmaceutically acceptable salt or pharmaceutical composition as described herein.

DETAILED DESCRIPTION OF THE INVENTION

In one aspect, the invention comprises compounds of Formula (I),

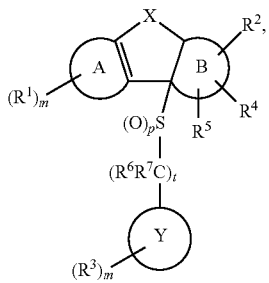

I or a stereoisomer or pharmaceutically acceptable salt thereof, wherein

X is $-CR^4R^5-$, $-(CR^4R^5)_2-$, $-OCR^6R^7-$, $-S(O)_pCR^6R^7-$, $-S(O)(NR^g)CR^6R^7-$ or $-NR^6CR^6R^7-$; wherein when X is $-OCR^6R^7-$, $-S(O)_pCR^6R^7-$, $-S(O)(NR^g)CR^6R^7-$ or $-NR^6CR^6R^7-$; the structure contemplated, for example when X is $-OCR^6R^7-$, would be

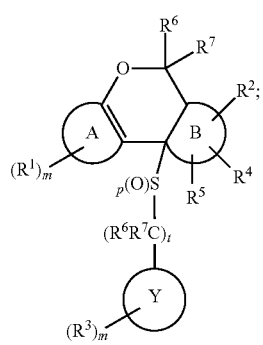

A is a 5- or 6-membered monocyclic heteroaromatic ring;
B is a 5- or 6-membered monocyclic heterocyclic ring;
Y is a 5 or 6-membered aromatic or heteroaromatic ring;

$R^1$ is, independently at each occurrence, selected from hydrogen, CD3, halo, $OCF_3$, CN, $S(O)_p(C_1$-$C_6)$alkyl, $S(O)(NR^g)(C_1$-$C_6)$alkyl, $-S(O)_p(C_1$-$C_6)$alkyl-OH, $S(O)(NR^g)(C_1$-$C_6)$alkyl-OH, -thioalkoxyalkoxy (e.g. $-SCH_2CH_2OCH_3$), $NR^{11}R^{11}$, $C_{1-6}$ alkyl substituted with 0-3 $R^{1a}$, $O-C_{1-6}$ alkyl substituted with 0-3 $R^{1a}$, $-(CR^{1b}R^{1c})_r$-3-14 membered carbocycle substituted with 0-3 $R^{1a}$ and $-(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^{1a}$;

$R^{1a}$ is, independently at each occurrence, hydrogen, =O, halo, $CF_3$, $OCF_3$, CN, $NO_2$, $-(CR^{1b}R^{1c})_r$-$OR^b$, $-(CR^{1b}R^{1c})_r$-$S(O)_pR^b$, $-(CR^{1b}R^{1c})_r$-$S(O)(NR^g)R^b$, $-(CR^{1b}R^{1c})_r$-$C(O)R^b$, $-(CR^{1b}R^{1c})_r$-$C(O)OR^b$, $-(CR^{1b}R^{1c})_r$-$OC(O)R^b$, $-(CR^{1b}R^{1c})_r$-$NR^{11}R^{11}$, $(CR^{1b}R^{1c})_r$-$C(O)NR^{11}R^{11}$, $-(CR^{1b}R^{1c})_r$-$NR^bC(O)R^c$, $-(CR^{1b}R^{1c})_r$-$NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{1b}R^{1c})_r$-3-14 membered carbocycle substituted with 0-3 $R^a$, or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{1b}$ and $R^{1c}$ are, independently at each occurrence, hydrogen, halogen or $C_{1-6}$ alkyl;

$R^2$ is selected from hydrogen, CN, $-(CR^{2e}R^{2f})_r$-$C(O)R^{2d}$, $-(CR^{2e}R^{2f})_r$-$C(O)OR^{2b}$, $-(CR^{2e}R^{2f})_r$-$C(O)NR^{11}R^{11}$, $-(CR^{2e}R^{2f})_r$-$S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})_r$-3-10 membered carbocycle substituted with 0-4 $R^a$, and $-(CR^{2e}R^{2f})_r$-4-7 membered heterocycle comprising carbon atoms, and 1-4 heteroatoms selected from N, O, P(O), $S(O)_p$ and $S(O)(NR^g)$, substituted with 0-4 $R^a$;

$R^{2a}$ is, independently at each occurrence, hydrogen, =O, halo, $OCF_3$, CN, $NO_2$, $-(CR^{2e}R^{2f})_r$-$OR^b$, $-(CR^{2e}R^{2f})_r$-$S(O)_pR^b$, $-(CR^{2e}R^{2f})_r$-$S(O)(NR^g)R^b$, $-(CR^{2e}R^{2f})_r$-$C(O)R^b$, $-(CR^{2e}R^{2f})_r$-$C(O)OR^b$, $-(CR^{2e}R^{2f})_r$-$OC(O)R^b$, $-(CR^{2e}R^{2f})_r$-$OC(O)NR^{11}R^{11}$, $-(CR^{2e}R^{2f})_r$-$OC(O)OR^c$, $-(CR^{2e}R^{2f})_r$-$NR^{11}R^{11}$, $-(CR^{2e}R^{2f})_r$-$C(O)NR^{11}R^{11}$, $-(CR^{2e}R^{2f})_r$-$NR^bC(O)_pR^c$, $-(CR^{2e}R^{2f})_r$-$NR^bC(O)OR$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-4-7 membered heterocycle comprising carbon atoms, and 1-4 heteroatoms selected from N, O, $S(O)_p$ and $S(O)(NR^g)$, substituted with 0-4 $R^a$;

$R^{2b}$ is, independently at each occurrence, hydrogen, $CF_3$, $-(CR^{2e}R^{2f})_q$-$OR^b$, $-(CR^{2e}R^{2f})_q$-$S(O)_pR^b$, $-(CR^{2e}R^{2f})_q$-$S(O)(NR)R^b$, $-(CR^{2e}R^{2f})_r$-$C(O)R^c$, $-(CR^{2e}R^{2f})_r$-$C(O)OR^b$, $-(CR^{2e}R^{2f})_q$-$OC(O)R^b$, $-(CR^{2e}R^{2f})_q$-$NR^{11}R^{11}$, $-(CR^{2e}R^{2f})_r$-$C(O)NR^{11}R^{11}$, $-(CR^{2e}R^{2f})_q$-$NR^bC(O)R^c$, $-(CR^{2e}R^{2f})_q$-$NR^bC(O)OR^c$, $-(CR^{2e}R^{2f})_q$-$NR^bC(O)NR^{11}R^{11}$, $-(CR^{2e}R^{2f})_q$-$S(O)_2NR^{11}R^{11}$, $-(CR^{2e}R^{2f})_q$-$NR^bS(O)_2R^c$, $C_{1-6}$ alkyl substituted with 0-2 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, —$(CR^{2e}R^{2f})_r$—$C_{3-10}$ cycloalkyl substituted with 0-3 $R^d$, where the cycloalkyl ring may be fused, bridged or spirocyclic, —$(CR^{2e}R^{2f})_r$-phenyl substituted with 0-2 $R^a$, or a —$(CR^{2e}R^{2f})_r$-4-10 membered heterocycle where the heterocycle may be fused, bridged or spirocyclic, containing 1-4 heteroatoms selected from N, O, $S(O)_p$ and $S(O)(NR^g)$, substituted with 0-4 $R^a$;

$R^{2e}$ and $R^{2f}$ are, independently at each occurrence, hydrogen, halogen or $C_{1-6}$ alkyl; $R^3$ is, independently at each occurrence, selected from hydrogen, halo, $N_3$, CN, —$(CR^{1b}R^{1c})_r$—$OR^{3b}$, —$(CR^{1b}R^{1c})_r$—$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, $S(O)_p$ and $S(O)(NR^g)$, both optionally substituted with 0-3$R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$;

$R^{3b}$ is, independently at each occurrence, hydrogen, $CF_3$, —$(CR^{1b}R^{1c})_qOR^b$, —$(CR^{1b}R^{1c})_qS(O)_pR^b$, —$(CR^{1b}R^{1c})_qS(O)(NR)R^b$, —$(CR^{1b}R^{1c})_r$—$C(O)R^{3d}$, —$(CR^{1b}R^{1c})_r$—$C(O)OR^b$, —$(CR^{1b}R^{1c})_qOC(O)R^b$, —$(CR^{1b}R^{1c})_qNR^{11}R^{11}$, —$(CR^{1b}R^{1c})_r$—$C(O)NR^{11}R^{11}$, —$(CR^{1b}R^{1c})_qNR^bC(O)R^{3c}$, —$(CR^{1b}R^{1c})_qNR^bC(O)OR^c$, —$(CR^{1b}R^{1c})_qNR^bC(O)NR^{11}R^{11}$, —$(CR^{1b}R^{1c})_qS(O)_2NR^{11}R^{11}$, —$(CR^{1b}R^{1c})_qNR^bS(O)_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C(=O)C_{1-4}$ alkyl, $C(=O)OC_{1-4}$ alkyl, $C_{1-6}$ alkyl or $C_{1-6}$ haloalkyl; or $R^6$ and $R^7$ taken together are =O;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^d$;

or one $R^{11}$ and a second $R^{11}$, both attached to the same nitrogen atom, combine to form a heterocycle comprising carbon atoms and 1-4 heteroatoms selected from N, O, $S(O)_p$ and $S(O)(NR^g)$, substituted with 0-4 $R^d$;

$R^a$ is, independently at each occurrence, hydrogen, =O, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—$C(O)R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $SO(NR^g)R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $SO(NR^g)(C_{1-6}$ alkyl), $CO_2H$, $CO_2(C_{1-6}$ alkyl), OH, $C_{3-6}$ cycloalkyl, $CF_3$; $O(C_{1-6}$ alkyl); or an optionally substituted —$(CR^{1b}R^{1c})_r$-5-10 membered heterocycle comprising carbon atoms and 1-4 heteroatoms selected from N, O, $S(O)_p$ and $S(O)(NR^g)$, phenyl or $C_{3-6}$ cycloalkyl, each group optionally substituted with halo, CN, $CF_3$, $C_{1-6}$ alkyl or $O(C_{1-6}$ alkyl);

$R^g$ is, independently at each occurrence, hydrogen, $C_{1-6}$ alkyl substituted with 0-3 $R^f$, $C_{1-6}$ haloalkyl, —$(CR^{1b}R^{1c})_r$—$C(O)R^b$, —$(CR^{1b}R^{1c})_r$—$C(O)OR^b$, —$(CR^{1b}R^{1c})_r$—$C(O)NR^{11}R^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(O) and $S(O)_p$ substituted with 0-4 $R^f$;

m is 0, 1, 2 or 3;

p and q are, independently at each occurrence, 0, 1, or 2;

r is 0, 1, 2, 3, or 4; and t is 0 or 1.

In a second aspect, the invention comprises compounds of the formula

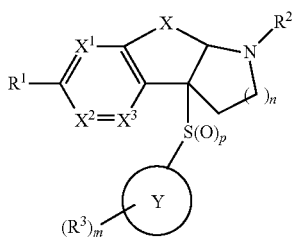

wherein

X is —CR$^4$R$^5$—, —(CR$^4$R$^5$)$_2$, —OCR$^6$R$^7$—, —S(O)$_p$CR$^6$R$^7$—, —S(O)(NR$^g$)CR$^6$R$^7$— or —NR$^6$CR$^6$R$^7$—;

X$^1$, X$^2$ and X$^3$ are, independently, selected from N or CR$^{1d}$;

Y is a 5 or 6-membered aromatic or heteroaromatic ring;

R$^1$ is selected from hydrogen, CD$_3$, halo, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is selected from hydrogen, CN, —(CR$^{2e}$R$^{2f}$)$_r$—C(O)R$^{2d}$, —(CR$^{2e}$R$^{2f}$)$_r$—C(O)OR$^{2b}$, —(CR$^{2e}$R$^{2f}$)$_r$—C(O)NR$^{11}$R$^{11}$, —(CR$^{2e}$R$^{2f}$)$_r$—S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)$_r$-3-10 membered carbocycle substituted with 0-4 R$^a$, and —(CR$^{2e}$R$^{2f}$)$_r$-4-7 membered heterocycle comprising carbon atoms, and 1-4 heteroatoms selected from N, O, P(O), S(O)$_p$ and S(O)(NR$^g$), substituted with 0-4 R$^a$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)$_r$—C$_{3-10}$ cycloalkyl substituted with 0-3 R$^d$, where the cycloalkyl ring may be fused, bridged or spirocyclic, —(CR$^{2e}$R$^{2f}$)$_r$-phenyl substituted with 0-2 R$^a$, or a —(CR$^{2e}$R$^{2f}$)$_r$-4-10 membered heterocycle where the heterocycle may be fused, bridged or spirocyclic, containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$) R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$NR$^b$C(O)R$^c$, —(CR$^{1b}$R$^{1c}$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR)R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R⁴ and R⁵ are independently hydrogen, $C_{1-6}$ alkyl or $C_{1-6}$ haloalkyl, or R⁴ and R⁵ together with the carbon atom to which they are attached form a 3- to 6-membered spirocarbocyclyl ring or a spiroheterocyclyl ring;

R⁶ and R⁷ are independently hydrogen, C(=O)$C_{1}$-4 alkyl, C(=O)O$C_{1-4}$ alkyl, $C_{1-6}$ alkyl or $C_{1-6}$ haloalkyl;

R¹¹ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^d$;

or one R¹¹ and a second R¹¹, both attached to the same nitrogen atom, combine to form a heterocycle comprising carbon atoms and 1-4 heteroatoms selected from N, O, $S(O)_p$ and $S(O)(NR^g)$, substituted with 0-4 $R^d$;

$R^d$ is, independently at each occurrence, hydrogen, =O, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$, or —$(CR^{1b}R^{1c})_r$-6-10 membered carbocycle substituted with 0-3 $R^d$;

R is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—$C(O)R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $SO(NR^g)R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $SO(NR^g)(C_{1-6}$ alkyl), $CO_2H$, $CO_2(C_{1-6}$ alkyl), OH, $C_{3-6}$ cycloalkyl, $CF_3$; $O(C_{1-6}$ alkyl); or an optionally substituted —$(CR^{1b}R^{1c})_r$-5-10 membered heterocycle comprising carbon atoms and 1-4 heteroatoms selected from N, O, $S(O)_p$ and $S(O)(NR^g)$, phenyl or $C_{3-6}$ cycloalkyl, each group optionally substituted with halo, CN, $CF_3$, $C_{1-6}$ alkyl or $O(C_{1-6}$ alkyl);

$R^g$ is, independently at each occurrence, hydrogen, $C_{1-6}$ alkyl substituted with 0-3 $R^f$, $C_{1-6}$ haloalkyl, —$(CR^{1b}R^{1c})_r$—$C(O)R^b$, —$(CR^{1b}R^{1c})_r$—$C(O)OR^b$, —$(CR^{1b}R^{1c})_r$—$C(O)NR^{11}R^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(O) and $S(O)_p$ substituted with 0-4 $R^f$;

m is 0, 1, 2 or 3;

n is 0, 1 or 2;

p and q are, independently at each occurrence, 0, 1, or 2; and r is 0, 1, 2, 3, or 4;

or a stereoisomer or pharmaceutically-acceptable salt thereof.

In a third aspect, the invention comprises compounds of the formula

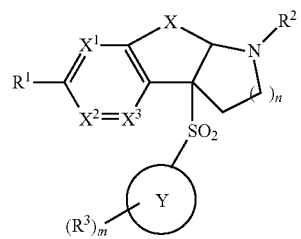

wherein

X is —$CR^4R^5$—, —$(CR^4R^5)_2$—, —$OCR^6R^7$—, —$S(O)_pCR^6R^7$—, —$S(O)(NR^g)CR^6R^7$— or —$NR^6CR^6R^7$—;

$X^1$, $X^2$ and $X^3$ are, independently, selected from N or $CR^{1d}$;

Y is a 5 or 6-membered aromatic or heteroaromatic ring;

R¹ is selected from halo, $C_{1-6}$ alkyl substituted with 0-3 $R^{1a}$, O—$C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^{1a}$;

$R^{1a}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, $(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^c)_r$-5-7 membered heterocycle comprising carbon atoms and 1-4 heteroatoms selected from N, O, $S(O)_p$ and $S(O)(NR^g)$, substituted with 0-3 $R^a$;

$R^{1b}$ and $R^{1c}$ are, independently at each occurrence, hydrogen, halogen or $C_{1-6}$ alkyl;

$R^1d$ is, independently at each occurrence, hydrogen, $CD_3$, halo, $CF_3$, and $C_1$-$C_4$ alkyl;

R² is selected from hydrogen, CN, —$(CR^{2e}R^{2f})_r$—$C(O)R^{2d}$, —$(CR^{2e}R^{2f})_r$—$C(O)OR^{2b}$, —$(CR^{2e}R^{2f})_r$—$C(O)NR^{11}R^{11}$, —$(CR^{2e}R^{2f})_r$—$S(O)_2R^{2c}$, $C_{1-6}$ alkyl substituted with 0-3 $R^{2a}$, $C_{2-6}$ alkenyl substituted with 0-3 $R^{2a}$, —$(CR^{2e}R^{2f})_r$-3-10 membered carbocycle substituted with 0-4 $R^a$, and —$(CR^{2e}R^{2f})_r$-4-7 membered heterocycle comprising carbon atoms, and 1-4 heteroatoms selected from N, O, P(O), $S(O)_p$ and $S(O)(NR^g)$, substituted with 0-4 $R^a$;

$R^{2a}$ is, independently at each occurrence, hydrogen, =O, halo, $OCF_3$, CN, $NO_2$, —$(CR^{2e}R^{2f})_r$—$OR^b$, —$(CR^{2e}R^{2f})_r$—$S(O)_pR^b$, —$(CR^{2e}R^{2f})_r$—$S(O)(NR^g)R^b$, —$(CR^{2e}R^{2f})_r$—C (O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^2$)$_r$—C$_{3-10}$ cycloalkyl substituted with 0-3 R$^d$, where the cycloalkyl ring may be fused, bridged or spirocyclic, —(CR$^{2e}$R$^{2f}$)$_r$-phenyl substituted with 0-2 R$^a$, or a —(CR$^{2e}$R$^{2f}$)$_r$-4-10 membered heterocycle where the heterocycle may be fused, bridged or spirocyclic, containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^G$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^e$, C(O)NR$^e$R$^e$, —NR$^e$C(O)R$^e$, CO$_2$H, CO$_2$R$^e$, —NR$^e$SO$_2$R$^e$, SO$_2$R$^e$, SO(NR$^g$)R$^e$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or $-(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $SO(NR^g)(C_{1-6}$ alkyl), $CO_2H$, $CO_2(C_{1-6}$ alkyl), OH, $C_{3-6}$ cycloalkyl, $CF_3$; $O(C_{1-6}$ alkyl); or an optionally substituted $-(CR^{1b}R^{1c})_r$-5-10 membered heterocycle comprising carbon atoms and 1-4 heteroatoms selected from N, O, $S(O)_p$ and $S(O)(NR^g)$, phenyl or $C_{3-6}$ cycloalkyl, each group optionally substituted with halo, CN, $CF_3$, $C_{1-6}$ alkyl or $O(C_{1-6}$ alkyl);

$R^g$ is, independently at each occurrence, hydrogen, $C_{1-6}$ alkyl substituted with 0-3 $R^f$, $C_{1-6}$ haloalkyl, $-(CR^{1b}R^{1c})_r-C(O)R^b$, $-(CR^{1b}R^{1c})_r-C(O)OR^b$, $-(CR^{1b}R^{1c})_r-C(O)NR^{11}R^{11}$, $-(CR^{1b}R^{1c})_r$-3-14 membered carbocycle, or $-(CR^{1b}R^{1c})_r$-5-7 membered heterocycle comprising carbon atoms and 1-4 heteroatoms selected from N, O, P(O) and $S(O)_p$ substituted with 0-4 $R^f$;

m is 0, 1, 2 or 3;

n is 0, 1 or 2;

p and q are, independently at each occurrence, 0, 1, or 2; and r is 0, 1, 2, 3, or 4;

or a stereoisomer or pharmaceutically-acceptable salt thereof.

In a fourth aspect, the invention comprises compounds of the formula

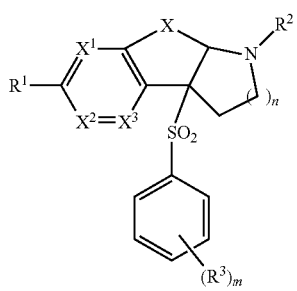

wherein

X is $-CR^4R^5-$, $-(CR^4R^5)_2-$, $-OCR^6R^7-$, $-S(O)_pCR^6R^7-$, $-S(O)(NR^g)CR^6R^7-$ or $-NR^6CR^6R^7-$;

$X^1$, $X^2$ and $X^3$ are, independently, selected from N or $CR^{1d}$;

$R^1$ is selected from halo, $C_{1-6}$ alkyl substituted with 0-3 $R^{1a}$, O—$C_{1-6}$ alkyl substituted with 0-3 $R^{1a}$, $-(CR^{1b}R^{1c})_r$-3-14 membered carbocycle substituted with 0-3 $R^{1a}$ and $-(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^{1a}$;

$R^{1a}$ is, independently at each occurrence, hydrogen, =O, halo, $CF_3$, $OCF_3$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $-(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{1b}R^{1c})_r$-3-14 membered carbocycle substituted with 0-3 $R^a$, or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is selected from hydrogen, CN, $-(CR^{2e}R^{2f})_r-C(O)R^{2d}$, $-(CR^{2e}R^{2f})_r-C(O)OR^{2b}$, $-(CR^{2e}R^{2f})_r-C(O)NR^{11}R^{11}$, $-(CR^{2e}R^{2f})_r-S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})_r$-3-10 membered carbocycle substituted with 0-4 $R^a$, and $-(CR^{2e}R^{2f})_r$-4-7 membered heterocycle comprising carbon atoms, and 1-4 heteroatoms selected from N, O, P(O), $S(O)_p$ and $S(O)(NR^g)$, substituted with 0-4 $R^a$;

$R^{2a}$ is, independently at each occurrence, hydrogen, =O, halo, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-S(O)(NR^g)R^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-OC(O)NR^{11}R^{11}$, $-(CR^{2e}R^{2f})_r-OC(O)OR^c$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R$, $-(CR^{2e}R^{2f})_r-NR^bC(O)OR$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-4-7 membered heterocycle comprising carbon atoms, and 1-4 heteroatoms selected from N, O, $S(O)_p$ and $S(O)(NR^g)$, substituted with 0-4 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})_qS(O)(NR^g)R^b$, $-(CR^{2e}R^{2f})_r-C(O)R^c$, $-(CR^{2e}R^{2f})_r-C(O)OR^b$, $-(CR^{2e}R^{2f})_qOC(O)R^b$, $-(CR^{2e}R^{2f})_qNR^{11}R^{11}$, $-(CR^{2e}R^{2f})_r-C(O)NR^{11}R^{11}$, $-(CR^{2e}R^{2f})_qNR^bC(O)R^c$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^e$, $C_{1-6}$ alkyl substituted with 0-2 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $-(CR^{2e}R^{2f})_r-C_{3-10}$ cycloalkyl substituted with 0-3 $R^d$, where the cycloalkyl ring may be fused, bridged or spirocyclic, $-(CR^{2e}R^{2f})_r$-phenyl substituted with 0-2 $R^a$, or a $-(CR^{2e}R^{2f})_r$-4-10 membered heterocycle where the heterocycle may be fused, bridged or spirocyclic, containing 1-4 heteroatoms selected from N, O, $S(O)_p$ and $S(O)(NR^g)$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, $-(CR^{1b}R^{1c})_r-OR^{3b}$, $-(CR^{1b}R^{1c})_r-NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$) R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)R$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^d$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;

n is 0, 1 or 2;

p and q are, independently at each occurrence, 0, 1, or 2; and r is 0, 1, 2, 3, or 4;

or a stereoisomer or pharmaceutically-acceptable salt thereof.

In a 5$^{th}$ aspect, the invention comprises compounds of the formula

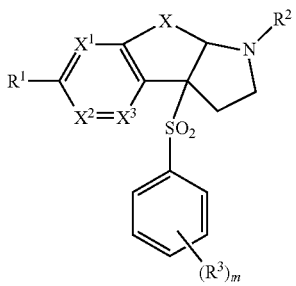

or a stereoisomer or pharmaceutically-acceptable salt thereof.

In a 6$^{th}$ aspect, the invention comprises compounds of the formula

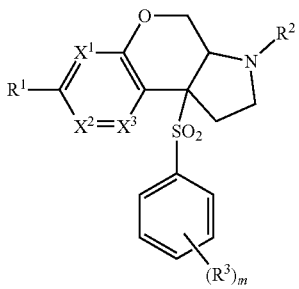

or a stereoisomer or pharmaceutically-acceptable salt thereof.

In a 7th aspect, the invention comprises compounds of the formula

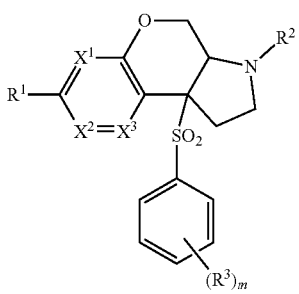

or a stereoisomer or pharmaceutically-acceptable salt thereof.

In an 8th aspect, the invention comprises compounds of the formula

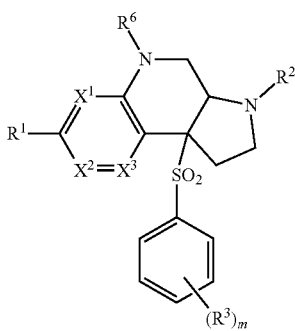

or a stereoisomer or pharmaceutically-acceptable salt thereof.

In a 9th aspect, the invention comprises compounds within the 6th aspect, wherein $X^1$, $X^2$ and $X^3$ are, independently, selected from N or CH;

$R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl$)_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, $(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 10th aspect, the invention comprises compounds within the 7th aspect, wherein $X^1$, $X^2$ and $X^3$ are, independently, selected from N or CH;

$R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl$)_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)$ $R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In an 11th aspect, the invention comprises compounds within the 8th aspect,
wherein
one of $X^1$, $X^2$ and $X^3$ is N, and the other two of $X^1$, $X^2$ and $X^3$ are CH;

$R^1$ is halo, phenyl substituted with 0-3 $R^{1a}$, $C_{1-6}$ alkyl substituted with 0-3 $R^{1a}$, or $O$—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl$)_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)$ $R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 12th aspect, the invention comprises compounds within the 9th aspect,
wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$ or $O$—$C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —$C(O)OR^{2b}$, —$C(O)R^{2d}$, —$C(O)NR^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

In a 13th aspect, the invention comprises compounds according to the 11th aspect,
wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —C(O)O$R^{2b}$, —C(O)$R^{2d}$, —C(O)N$R^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, S(O)$_p$ and S(O)(N$R^g$), substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, S(O)$_p$ and S(O)(N$R^g$), substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

In a 14$^{th}$ aspect, the invention comprises compounds according to the 12$^{th}$ aspect,
wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —C(O)O$R^{2b}$, —C(O)$R^{2d}$, —C(O)N$R^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, S(O)$_p$ and S(O)(N$R^g$), substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, S(O)$_p$ and S(O)(N$R^g$), substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

In another aspect, there is provided a compound of Formula (I), or stereoisomers, tautomers, pharmaceutically acceptable salts, solvates, or prodrugs thereof, wherein $R^2$ is:

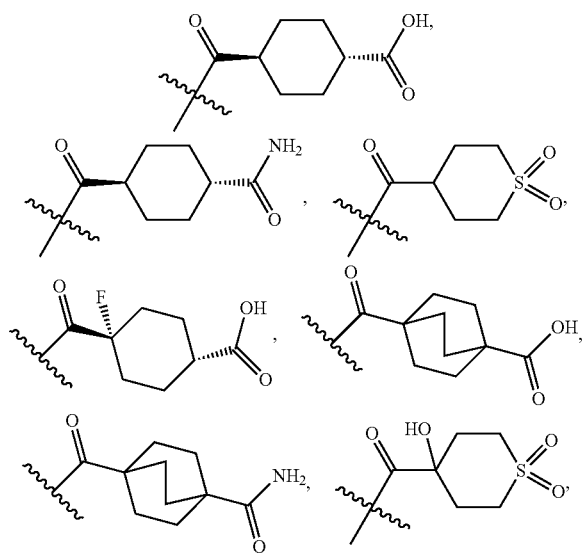

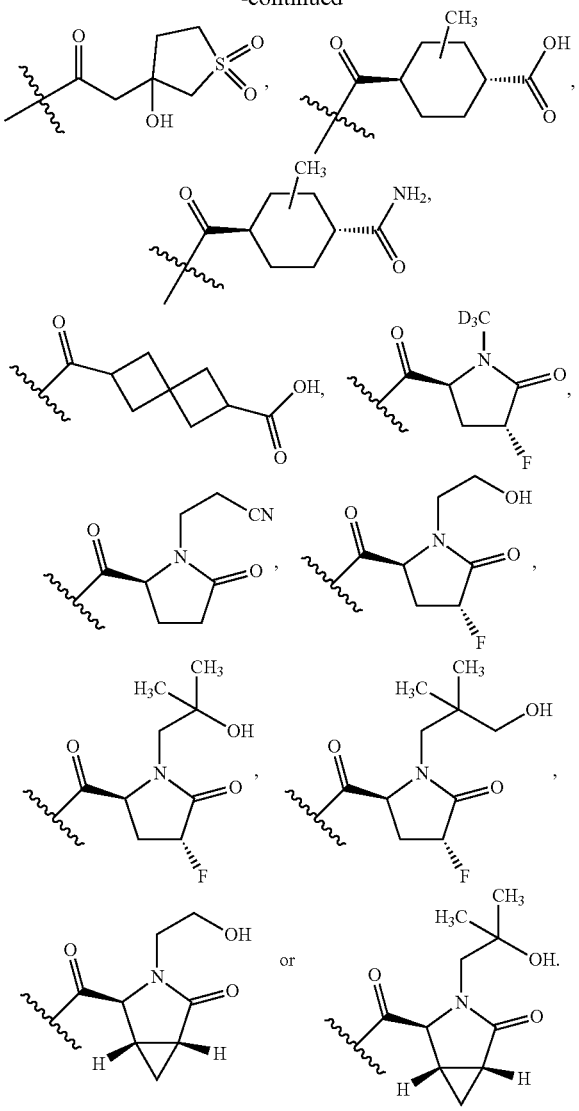

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group, for example, aryl or heteroaryl groups which are optionally substituted for example with alkyl, halo or haloalkyl. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group C

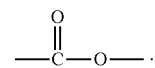

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Thus, examples of aryl groups include:

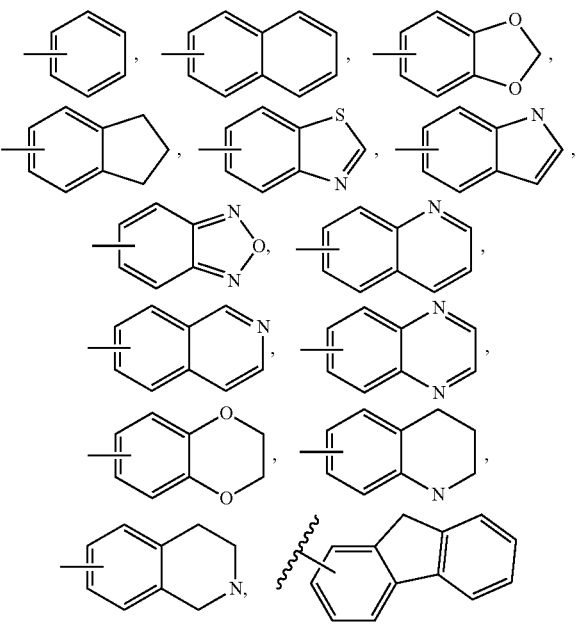

(fluorenyl) and the like, which optionally may be substituted at any available carbon or nitrogen atom. A preferred aryl group is optionally-substituted phenyl.

Accordingly, in compounds of Formula I, the term "cycloalkyl" includes cyclopropyl, cyclobutyl, cyclopentyl, cyclohexyl, cycloheptyl, bicyclooctyl, etc., as well as the following ring systems:

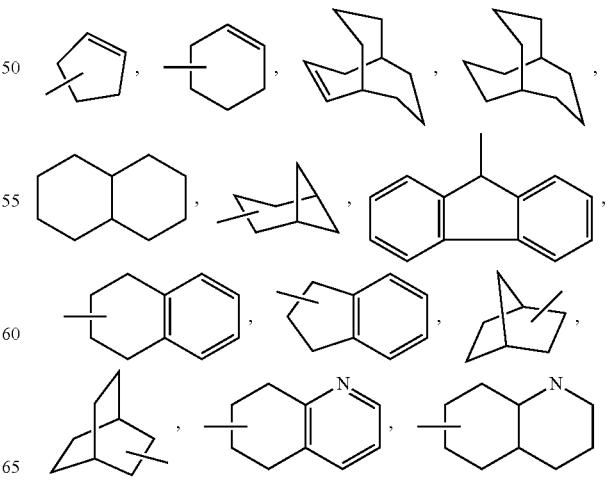

and the like, which optionally may be substituted at any available atoms of the ring(s). Preferred cycloalkyl groups include cyclopropyl, cyclopentyl, cyclohexyl, and

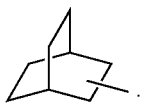

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

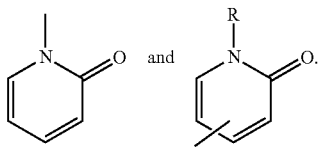

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrolinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of Formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of Formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formula I may be formed, for example, by reacting a compound of the Formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, hydrogen sulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogen sulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. One enantiomer of a compound of Formula I may display superior activity compared with the other.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the Formula I, and/or a salt and/or solvate thereof. Any compound that will be converted in vivo to provide the bioactive agent (i.e., the compound for Formula I) is a prodrug within the scope and spirit of the invention. For example, compounds containing a carboxy group can form physiologically hydrolyzable esters which serve as prodrugs by being hydrolyzed in the body to yield Formula I compounds per se. Such prodrugs are preferably administered orally since hydrolysis in many instances occurs principally under the influence of the digestive enzymes. Parenteral administration may be used where the esterper se is active, or in those instances where hydrolysis occurs in the blood. Examples of physiologically hydrolyzable esters of compounds of Formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the Formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to Formula (I), stereoisomeric form, N-oxide, pharmaceutically acceptable salt, solvate, hydrate or pharmaceutical composition as described herein. See, e.g, L. A. Solt et al., "Action of RORs and their ligands in (patho)physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," Nucl. Recept. Signal. 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g, M. Leppkes et al., "ROR-gamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the $CD_2$ promoter induces polyclonal plasmacytosis and autoantibody production in transgenic mice," *Eur. J. Immunol.,* 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J Clin. Invest.,* 2012 Jun. 1; 122(6):2252-6; and S. P. Raychaudhuri, "Role of IL-17 in Psoriasis and Psoriatic Arthritis," Clin. Rev. Allergy Immunol., 2013; 44(2): 183-193, each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factor T-bet and RORγt in mice," Blood, 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

Scheme 1 illustrates a method for the preparation of compounds 7. An appropriately functionalized carbonyl compound 1 (which can be purchased or synthesized using methods known in the literature), wherein R is $R^1$ or another group which may be converted to $R^1$ using methods known in the literature, may be reacted with an appropriate thiol in the presence of an acid such as HCl or $TiCl_4$ to afford a vinyl sulfide 2a, a thioketal 2b, a bis-sulfide 2c, or a mixture containing 2a and/or 2b and/or 2c. Oxidation of sulfide 2a, thioketal 2b, bis-sulfide 2c, or a mixture of 2a and/or 2b and/or 2c can be accomplished using a reagent such as m-chloroperoxybenzoic acid to afford sulfone 3a, bis-sulfone 3b, bis-sulfone 3c, or a mixture of 3a and/or 3b and/or 3c. A nucleophile such as an amino alcohol 4 can then be added, yielding an alcohol 5. The hydroxy group of this compound can be converted to a leaving group such as the corresponding methanesulfonate 6 using, for example, methanesulfonyl chloride and triethylamine, followed by treatment with a base such as potassium tert-butoxide, to give tricyclic amine 7.

SCHEME 1

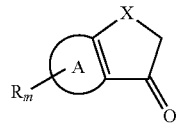

1

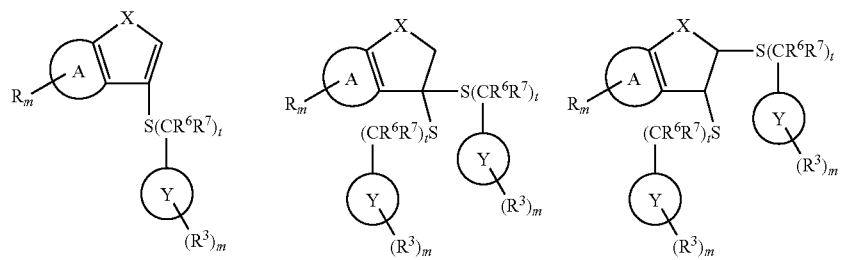

2a      2b      2c

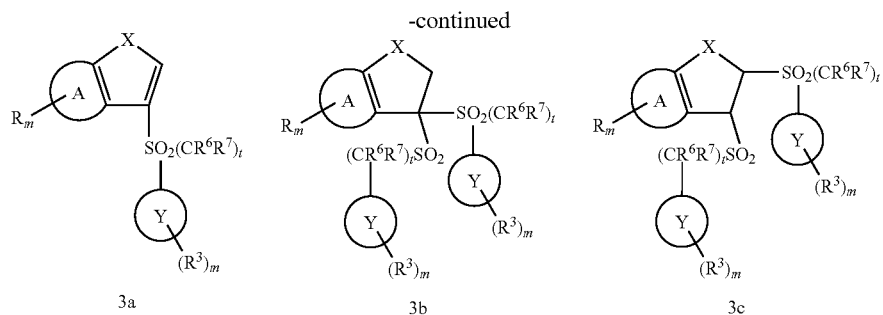

3a            3b            3c

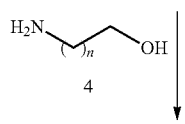

4

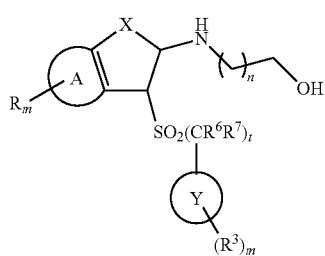

5

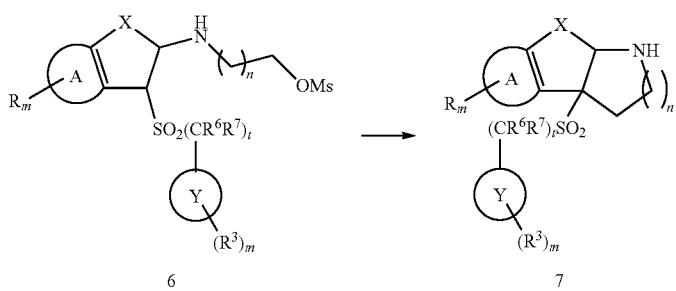

6            7

An alternative preparation of vinylic sulfide 2a, which can be converted to 7 as described above, is shown in Scheme 2. An appropriately functionalized carbonyl compound 1 can be converted to a vinylic trifluoromethanesulfonate 8, for example by treatment with trifluoromethanesulfonic anhydride and 2-chloropyridine, or with a base such as potassium bis(trimethylsilyl)amide followed by a reagent such as N-phenyl-trifluoromethanesulfonimide. This material can be treated with a thiol or lithium thiolate in the presence of a suitable palladium catalyst (see, for example, *Synlett* 1977, (7), 561) to provide 2a.

SCHEME 2

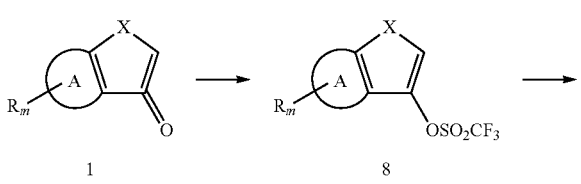

1            8

-continued

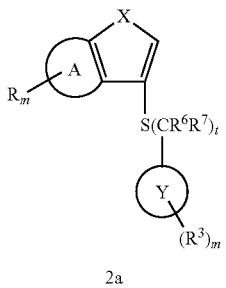

2a

Scheme 3 illustrates methods which can provide access to protected amine intermediates through modification of compounds 7 (Scheme 1). Amine 7, wherein R is a halide such as Cl, Br or I, can be treated with di-tert-butyl dicarbonate to provide the protected amine 9. Any of a number of well-known methods for converting an aromatic halide to a different group can then be applied to convert 9 into 10, where R' is a different substituent. Some examples, not meant to be limiting, are: (1) treatment with an aryl or alkenyl boronic acid or boronate ester in the presence of a suitable palladium catalyst, commonly known as the Suzuki coupling (see, for example, *Chem. Rev.* 1979, 95, 2457; *J. Organometallic Chem.* 1999, 576, 147), to give 10 where R' can be aryl, heteroaryl or alkenyl (the latter of which can be further converted to the corresponding alkyl by catalytic reduction); (2) treatment with a zinc reagent such as zinc(II) cyanide or an alkyl- or cycloalkylzinc halide in the presence of a suitable palladium catalyst, commonly known as the Negishi coupling (see, for example, *Metal-Catalyzed Cross-Coupling Reactions* ($2^{nd}$ edition), 2004, 815), to give 10 where R' can be, for example, alkyl, cycloalkyl or cyano; (3) treatment with an amine or amide in the presence of a suitable palladium catalyst, commonly known as the Buchwald-Hartwig coupling (see, for example, *Chem. Sci.* 2011, 2, 27; *Acc. Chem. Res.* 1998, 31, 805; *Angew. Chem. Int. Ed.* 2008, 47, 6338), to give 10 where R' can be, for example, dialkylamino; (4) treatment with an organomagnesium halide in the presence of a suitable iron catalyst (see, for example, *Org. React.* 2014, 83, 1; *J. Am. Chem. Soc.,* 2002, 13856), to give 10 where R' can be, for example, methyl or trideuteromethyl; (5) treatment with a fluorinated alkyl halide in the presence of a copper catalyst (see, for example, *Tetrahedron* 1969, 25, 5921; *Angew. Chem. Int. Ed.* 2011, 50, 3793), to give 10 where R' can be, for example, trifluoromethyl, heptafluoropropyl, heptafluoroisopropyl, or the like; (6) treatment with copper(I) halide to give 10 where R' is a different halide from R in 9; or (7) treatment with an optionally substituted carbinol in the presence of a suitable base or a suitable copper or palladium catalyst to give 10 where R' is an optionally substituted alkoxy group. Removal of the Boc protecting group can be achieved by treatment with a strong acid such as HCl or trifluoroacetic acid. The same or similar methods can also be applied to a protected amine 11 wherein R is a halide such as Cl, Br or I to give the corresponding 12 where R' is a different group, as described above.

Alternatively, a compound 9 where R is hydroxy can be converted to a compound 10 where R' is, for example, Br by treatment with a reagent such as phosphorus oxybromide. A compound 9 where R is hydroxy can also be converted to a compound 10 where R' is an optionally substituted alkoxy group by treatment with an alkylating agent such as an optionally substituted alkyl halide in the presence of a suitable reagent such as a base or a silver salt. As described above, removal of the Boc protecting group can be achieved by treatment with a strong acid such as HCl or trifluoroacetic acid. The same or similar methods can also be applied to a protected amine 11 wherein R is a hydroxy to give the corresponding 12 where R' is a different group, as described above.

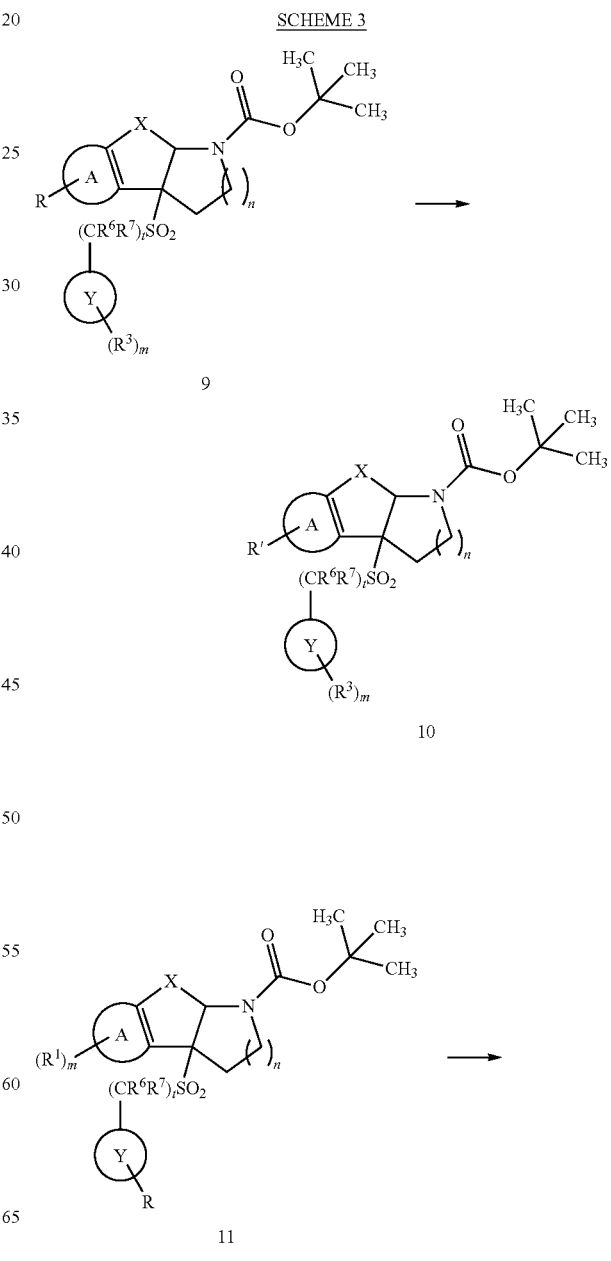

SCHEME 3

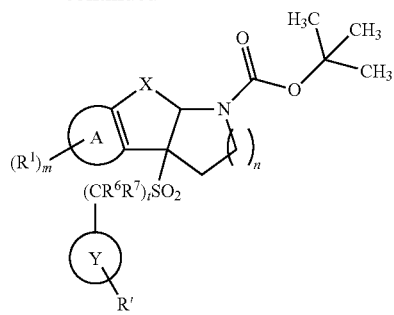

12

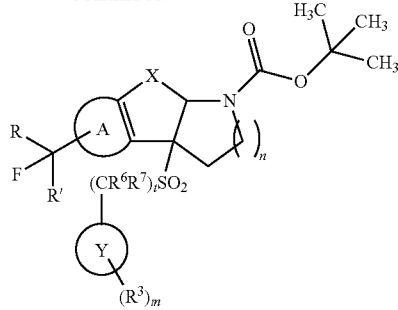

14

An alternative method for the conversion of a compound 9 where $R^1$ is Br or I to a compound 13 or 14 is shown in Scheme 4. Compound 9 can be treated with an organometallic reagent such as n-butyllithium, and then reacted with a carbonyl containing compound RC(=O)R' to provide alcohol 13. Optionally, alcohol 13 may be treated with a fluorinating agent such as (diethylamino)sulfur trifluoride, affording a fluorinated analog such as 14. Treatment of 13 or 14 with a strong acid such as HCl or trifluoroacetic acid would then remove the Boc protecting group.

SCHEME 4

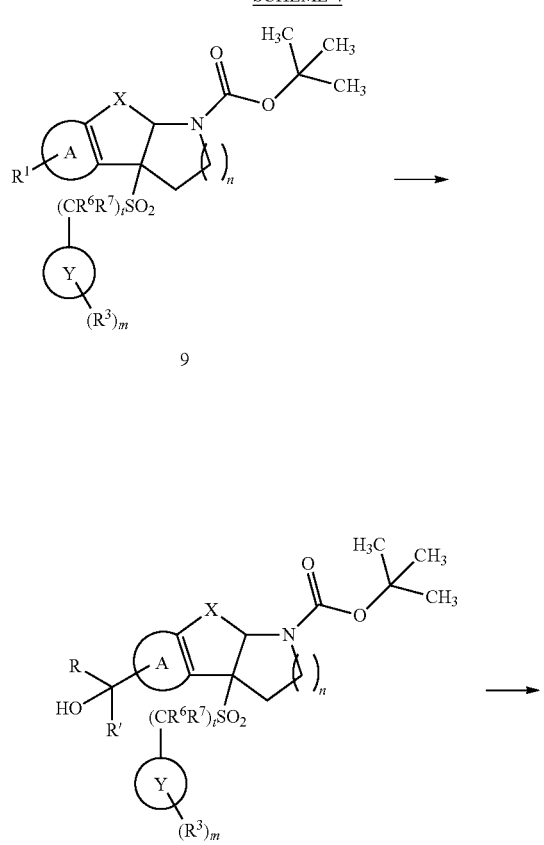

A variety of methods well known in the literature can be used for conversion of amines 7 to compounds of the present invention. Some examples are shown in Scheme 5. An amine 7 can be treated with an acid anhydride RC(=O)OC(=O)R or an acid chloride RC(=O)Cl in the presence of a base such as triethylamine or pyridine to provide an amide 15. Alternatively, an amine 7 can be treated with an acid RC(=O)OH in the presence of a suitable base and a coupling reagent such as (benzotriazol-1-yloxy)tris(dimethylamino)phosphonium hexafluorophosphate (BOP), O-(7-azabenzotriazol-1-yl)-1,1,3,3-tetramethyluronium hexafluorophosphate (HATU), benzotriazol-1-yl-oxytripyrrolidinophosphonium hexafluorophosphate (PyBOP), or a combination of 1-hydroxybenzotriazole (HOBT) and N-(3-dimethylaminopropyl)-N'-ethylcarbodiimide (EDC) to provide an amide 15. An amine 7 can also be treated with a sulfonyl chloride $RSO_2Cl$ in the presence of a suitable base to provide a sulfonamide 16. An amine 7 can also be treated with an isocyanate RN=C=O to provide a urea 17 (where R' is H), or with an aminocarbonyl chloride RN(R')C(=O)Cl to provide a urea 17. Alternatively, an amine 7 can be treated with phosgene or triphosgene to provide the intermediate N-chlorocarbonyl derivative, which can then be treated with an amine RN(R')H to provide a urea 17. An amine 7 can be treated with a sulfamyl chloride $RN(R')SO_2Cl$ to provide a sulfamide 18. An amine 7 can be treated with an appropriate substituted or unsubstituted alkyl halide, cycloalkyl halide, or arylalkyl halide RC(R')(H)X' where X' is Br, I or Cl, or with a related alkyl group containing another leaving group X' such as methanesulfonate or trifluoromethanesulfonate, in the presence of a suitable base, to provide an alkylated amine 19. Alternatively, an amine 7 can be treated with an aldehyde RCHO or a ketone RC(=O)R', in the presence of a reducing agent such as sodium cyanoborohydride or sodium triacetoxyborohydride, to provide an alkylated amine 19 (where R' is H if an aldehyde is used). An amine 7 can be treated with an aryl or heteroaryl iodide ArI, an aryl or heteroaryl bromide ArBr, an aryl or heteroaryl chloride ArCl, or an aryl or heteroaryl trifluoromethanesulfonate $ArOS(=O)_2CF_3$ in the presence of a suitable palladium catalyst to provide an arylamine 20 (a reaction commonly known as the Buchwald-Hartwig coupling; see, for example, *Chem. Sci.* 2011, 2, 27; *Acc. Chem. Res.* 1998, 31, 805; *Angew. Chem. Int. Ed.* 2008, 47, 6338).

SCHEME 5

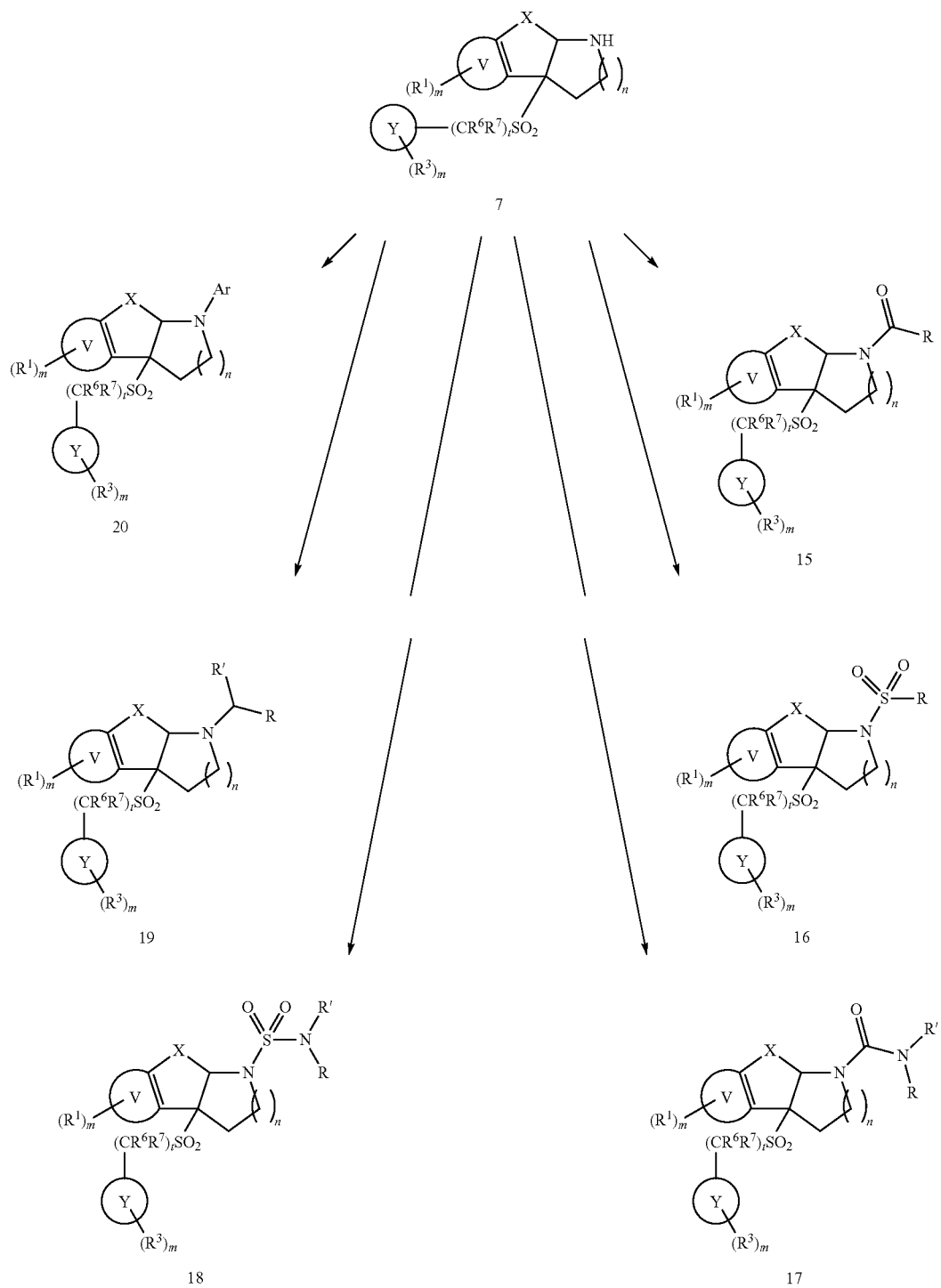

A variety of available methods may be used for conversion of intermediates or compounds of the invention to other intermediates or compounds of the invention. Some examples, well known to those skilled in the art of organic chemistry, include but are not limited to: conversion of a carboxylic acid ester to a carboxylic acid; conversion of a carboxylic acid to an amide; conversion of an amine to an amide, a urea, or a sulfonamide; alkylation or arylation of an amine; conversion of a halo group on an aromatic ring to an alkyl group, an aryl group or an amino group; and electrophilic substitution of an aromatic ring.

It will be appreciated by one skilled in the art of organic chemistry that various steps in a synthesis may be performed in an alternative sequence from that described in order to give a desired compound or compounds.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. In some instances alternative preparations of Intermediates or Examples are described. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. The intent of describing alternative preparations is to further enable the preparation of the Examples of this invention. In some instances some functional groups in the outlined Examples and claims may be replaced by well known bioisosteric replacements known in the art, for example, replacement of a carboxylic acid group with a tetrazole or a phosphate moiety. Starting materials and intermediates for which no preparation is explicitly shown are available commercially, are known in the literature, or may be prepared by analogy to similar compounds which are known in the literature.

Drying of organic solutions to remove residual water was done by allowing to stand over anhydrous sodium sulfate or anhydrous magnesium sulfate, followed by decantation or filtration. Solvent removal was performed by concentration under reduced pressure. Column chromatography was generally performed with pre-packed silica gel cartridges using a CombiFlash® automated chromatography apparatus (Teledyne Isco), eluting with the solvent or solvent mixture indicated. Analytical and preparative high performance liquid chromatography (HPLC) were generally performed using a reverse phase column of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic (SFC) purification or separation of enantiomers or diastereomers was performed using conditions described for the individual cases. Mass spectral data were obtained by liquid chromatography mass spectroscopy (LCMS) using electrospray ionization.

Many Intermediates and Examples are homochiral (entirely or mostly a single enantiomer), but in some cases the absolute configuration has not been proven. In those cases, a text notation to the left of the structure will indicate that the compound is homochiral, and indicates whether the compound was obtained from (or is derived from an intermediate which was obtained from) the specified peak eluting during chiral SFC separation. However, in all cases, the stereochemistry within the tricyclic ring system is cis. Thus, for example, the structure 21 shown below indicates that, while the material is homochiral, the absolute stereochemistry of the material, which was derived from the first-eluting peak during SFC separation, is not known, but is either the absolute stereochemistry shown in 21a or that shown in 21b.

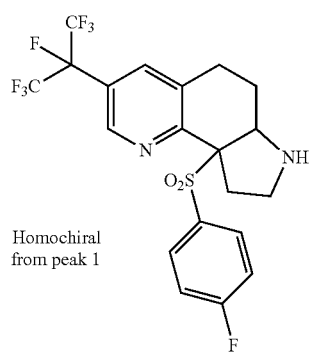

21

Homochiral
from peak 1

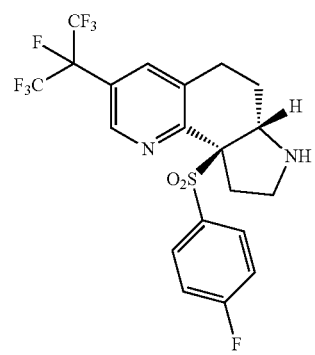

21a

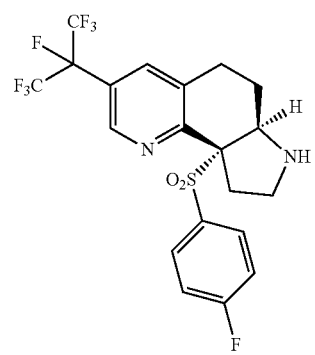

21b

In some cases, an Intermediate or Example is derived from combining a homochiral starting material with a non-homochiral or racemic starting material, yielding a mixture of two or more configurational isomers. In such cases, if the absolute stereochemistry of the homochiral starting material is not known, a text notation will indicate that the chiral centers of the tricyclic moiety are those of the homochiral tricyclic intermediate derived from the indicated peak eluting during chiral SFC separation (as above), while the non-homochiral asymmetric center or centers are indicated by a wavy line, for example as shown in structure 22 below.

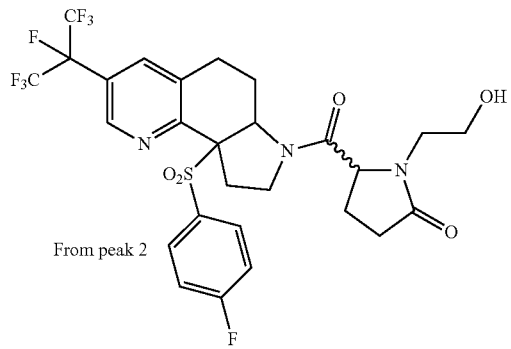

22

In some cases, a mixture of configurational isomers resulting from combining a homochiral starting material with a non-homochiral starting material has been separated by a method such as chiral SFC to give a homochiral product wherein the absolute stereochemistry at some or all of the asymmetric centers is not known. In such cases, the absolute configurations of any known chiral centers are shown explicitly, while a text notation will indicate the peak (from the separation of the diastereomeric mixture) from which the product was isolated. An example is shown in Structure 23 below, which indicates that, while the absolute configurations at all chiral centers are not known, the product 23 is homochiral and was isolated from peak 2 eluting during chiral separation of a mixture of configurational isomers.

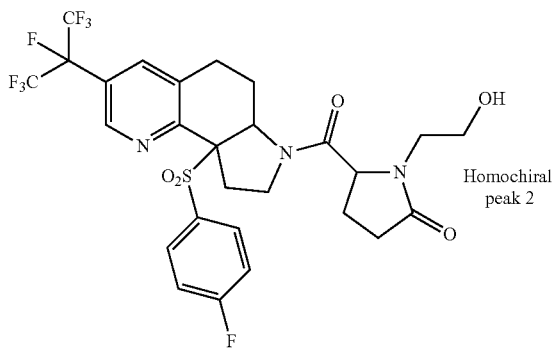

23

If the absolute configuration at an asymmetric center of an Intermediate or Example is known, or that asymmetric center is derived from a precursor whose absolute configuration is known, this is explicitly shown in the structure of the Intermediate or Example. If no absolute configuration is explicitly shown at an asymmetric center in a structure, and no text notation is present with the structure (as above), that chiral center is either racemic or of undefined stereochemistry.

Chemical names were determined using ChemBioDraw Ultra, version 14.0.0.126 (PerkinElmer Inc.). The following abbreviations are used:

| ABBREVIATION | NAME |
|---|---|
| DAST | (diethylamino)sulfur trifluoride |
| dba | dibenzylideneacetone |
| DCE | 1,2-dichloroethane |
| DCM | dichloromethane |
| DIEA | diisopropylethylamine |
| DMF | N,N-dimethylformamide |
| DMSO | dimethyl sulfoxide |
| EDC | N-(3-dimethylaminopropyl)-N'-ethylcarbodiimide |
| EtOAc | ethyl acetate |
| h | hour(s) |
| HATU | O-(7-azabenzotriazol-1-yl)-1,1,3,3-tetramethyluronium hexafluorophosphate |
| HOBT | 1-hydroxybenzotriazole |
| HPLC | high performance liquid chromatography |
| IPA | 2-propanol |
| LCMS | liquid chromatography-mass spectrometry |
| mCPBA | m-chloroperoxybenzoic acid |
| MeCN | acetonitrile |
| MeOH | methanol |
| min | minute(s) |
| MsCl | methanesulfonyl chloride |
| rt | room temperature |
| SFC | super-critical fluid chromatography |
| TEA | triethylamine |
| TFA | trifluoroacetic acid |
| THF | tetrahydrofuran |
| $t_R$ | chromatographic retention time |
| Xantphos | 4,5-bis(diphenylphosphino)-9,9-dimethylxanthene |

HPLC Methods

Method A: (Analytical)
Column: Acquity UPLC® BEH $C_{18}$ 2.1×50 mm, 1.7 m (Waters Corp.); mobile phase A: water with 0.05% TFA; mobile phase B: MeCN with 0.05% TFA; temperature: 50° C.; flow rate 0.80 mL/min; gradient: 2-98% B over 1 min, then 0.5 min isocratic at 98% B.

Method B: (Analytical)
Column: XBridge Shield BEH RP18 4.6×50 mm, 5 m (Waters Corp.); mobile phase A: MeOH-water 10:90 with 0.1% TFA; mobile phase B: MeOH-water 90:10 with 0.1% TFA; temperature: rt; flow rate 4 mL/min; gradient: 0-100% B over 4 min, then isocratic at 100% B.

Method C: (Analytical)
Column: Waters XBridge Cis, 2.1×50 mm, 1.7 m (Waters Corp.); mobile phase A: MeCN-water 5:95 with 0.1% TFA; mobile phase B: 95:5 MeCN-water with 0.1% TFA; temperature: 50° C.; flow rate 1 mL/min; gradient: 0-100% B over 3 min, then isocratic at 100% B.

Method D: (Preparative)
Column: XBridge™ $C_{18}$ 19×200 mm, 5 μm (Waters Corp.); mobile phase A: 5:95 MeCN-water with 10 mM ammonium acetate; mobile phase B: 95:5 MeCN-water with 10 mM ammonium acetate; flow rate 20 mL/min; gradient: increasing B, then isocratic at 100% B.

Method E: (Preparative)
Column: Luna® $C_{18}$ 30×100 mm, 5 μm (Phenomenex Inc.); mobile phase A: water with 0.1% TFA; mobile phase B: MeCN with 0.1% TFA; flow rate 30 mL/min; gradient: increasing B, then isocratic at 100% B.

Method F: (Preparative)
Column: XBridge™ $C_{18}$ 19×200 mm, 5 μm (Waters Corp.); mobile phase A: 5:95 MeCN-water with 0.1% TFA; mobile phase B: 95:5 MeCN-water with 0.1% TFA; flow rate 20 mL/min; gradient: increasing B, then isocratic at 100% B.

Intermediate 1

9a-((4-fluorophenyl)sulfonyl)-3-(perfluoropropan-2-yl)-6,6a,7,8,9,9a-hexahydro-5H-pyrrolo[2,3-h]quinoline dihydrochloride (Single Enantiomer)

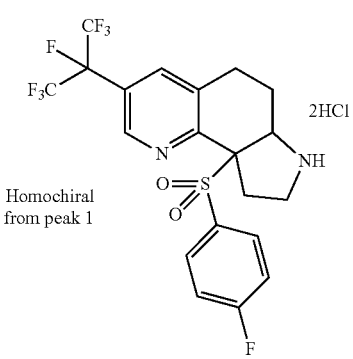 [SMILES: O=S(=O)(c1ccc(F)cc1)C12CCNC1CCc1cc(C(F)(C(F)(F)F)C(F)(F)F)cnc12]

Homochiral from peak 1

Step A: 3-bromo-7,8-bis((4-fluorophenyl)thio)-5,6,7,8-tetrahydroquinoline

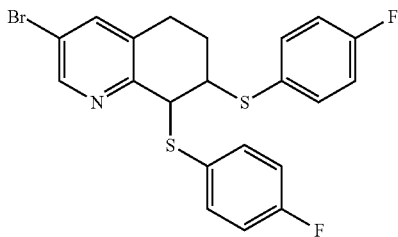 [SMILES: Fc1ccc(SC2CCc3cc(Br)cnc3C2Sc2ccc(F)cc2)cc1]

A suspension of 3-bromo-6,7-dihydroquinolin-8(5H)-one (5.58 g, 24.7 mmol) in IPA (49.4 mL) was treated with 4-fluorobenzenethiol (6.05 mL, 56.8 mmol). The solution was cooled in an ice-water bath and bubbled with HCl gas for about 5 min, and the resulting mixture (a suspension) was allowed to warm to rt overnight. After 17 h, significant starting material remained by LCMS. Additional IPA (49.4 mL) was added and the mixture was again bubbled with HCl gas for 10 min. After 3 h more, the mixture was poured into an ice-water mixture, EtOAc was added, and solid $NaHCO_3$ was slowly added with stirring until gas evolution ceased. The organic phase was separated, washed sequentially with saturated aqueous $NaHCO_3$ and brine, dried and concentrated to provide a yellow syrup. This was subjected to column chromatography to provide impure 3-bromo-7,8-bis((4-fluorophenyl)thio)-5,6,7,8-tetrahydroquinoline a light yellow syrup (3.67 g, 32% yield, about 80% purity), used without further purification. LCMS m/z 463.9, 465.9 (M+H)$^+$, HPLC $t_R$ 1.24 min (method A). $^1$H NMR (400 MHz, $CDCl_3$) δ 8.58 (d, J=2.2 Hz, 1H), 7.65 (d, J=2.0 Hz, 1H), 7.32-7.25 (m, 2H), 7.14 (t, J=6.3 Hz, 2H), 6.98-6.90 (m, 4H), 4.41 (s, 1H), 3.64-3.59 (m, 1H), 3.05 (m, 1H), 2.87-2.68 (m, 2H), 2.11-2.03 (m, 1H).

Step B: Mixture of 3-bromo-7,8-bis((4-fluorophenyl)sulfonyl)-5,6,7,8-tetrahydroquinoline and 3-bromo-8-((4-fluorophenyl)sulfonyl)-5,6-dihydroquinoline

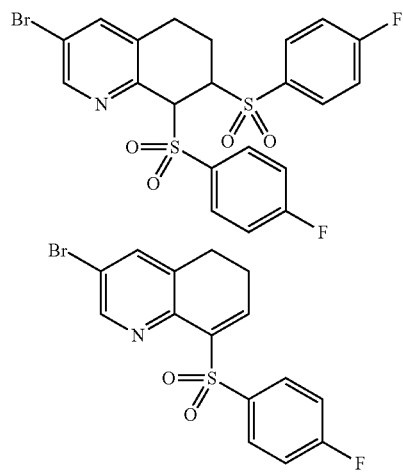

A solution of crude 3-bromo-8,8-bis((4-fluorophenyl)thio)-5,6,7,8-tetrahydroquinoline (3.45 g, 7.43 mmol) in DCM (120 mL) was stirred on an ice-water bath and treated with a solution of mCPBA (8.32 g, 37.1 mmol) in DCM (80 mL). The mixture was warmed to rt and stirred for 1.5 h, then was partitioned between DCM and saturated aqueous $NaHCO_3$. The organic phase was washed sequentially with saturated aqueous $NaHCO_3$, aqueous $Na_2S_2O_3$ and brine, dried and concentrated to give a mixture of 3-bromo-7,8-bis((4-fluorophenyl)sulfonyl)-5,6,7,8-tetrahydroquinoline and 3-bromo-8-((4-fluorophenyl)sulfonyl)-5,6-dihydroquinoline (about 3:1) as a white amorphous solid (3.92 g), used without further purification. LCMS m/z 527.0, 529.9 (M+H)$^+$, HPLC $t_R$ 1.00 min (75%), and m/z 367.9, 369.9 (M+H)$^+$, HPLC $t_R$ 0.97 min (25%) (method A).

Step C: 2-((3-bromo-8-((4-fluorophenyl)sulfonyl)-5,6,7,8-tetrahydroquinolin-7-yl)amino)ethanol

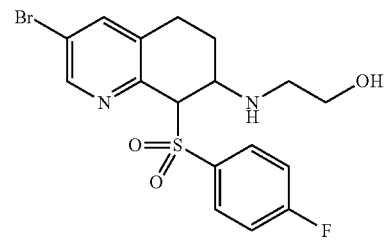 [SMILES: O=S(=O)(c1ccc(F)cc1)C1c2ncc(Br)cc2CCC1NCCO]

A solution of a crude mixture of 3-bromo-7,8-bis((4-fluorophenyl)sulfonyl)-5,6,7,8-tetrahydroquinoline and 3-bromo-8-((4-fluorophenyl)sulfonyl)-5,6-dihydroquinoline (3.92 g) in THF (74 mL) was stirred on an ice-water bath and treated with 2-aminoethanol (1.79 mL, 29.7 mmol). The mixture was warmed to rt, stirred for 1 h, and partitioned between EtOAc and saturated aqueous $NaHCO_3$. The organic phase was washed with brine, dried and concentrated to provide crude 2-((3-bromo-8-((4-fluorophenyl)sulfonyl)-5,6,7,8-tetrahydroquinolin-7-yl)amino)ethanol as a yellow amorphous solid (3.19 g, 80% purity), used without further purification. LCMS m/z 428.9, 430.9 (M+H)⁺, HPLC t_R 0.67 min (method A).

Step D: 3-bromo-9a-((4-fluorophenyl)sulfonyl)-6,6a,7,8,9,9a-hexahydro-5H-pyrrolo[2,3-h]quinoline (racemic)

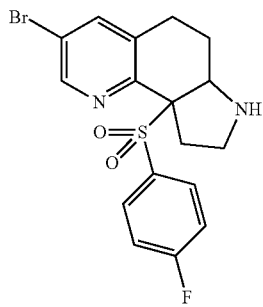 [SMILES: O=S(=O)(c1ccc(F)cc1)C12CCNC1CCc1cc(Br)cnc12]

A solution of crude 2-((3-bromo-8-((4-fluorophenyl)sulfonyl)-5,6,7,8-tetrahydroquinolin-7-yl)amino)ethanol (3.19 g) in DCM (198 mL) was stirred on an ice-water bath and treated sequentially with MsCl (0.533 mL, 6.84 mmol) and TEA (0.953 mL, 6.84 mmol). The mixture was warmed to rt and stirred for 1 h. A solution of potassium tert-butoxide (3.34 g, 29.7 mmol) in THF (40 mL) was added slowly and stirring was continued for 1 h. The mixture was partitioned between DCM and aqueous NaHCO₃. The organic phase was washed with brine, dried and concentrated to provide crude racemic 3-bromo-9a-((4-fluorophenyl)sulfonyl)-6,6a,7,8,9,9a-hexahydro-5H-pyrrolo[2,3-h]quinoline as a light brown amorphous solid (2.73 g, 70% purity), used without further purification. LCMS m/z 411.0, 413.0 (M+H)⁺, HPLC t_R 0.68 min (method A).

Step E: tert-butyl 3-bromo-9a-((4-fluorophenyl)sulfonyl)-6,6a,9,9a-tetrahydro-5H-pyrrolo[2,3-h]quinoline-7(8H)-carboxylate (racemic)

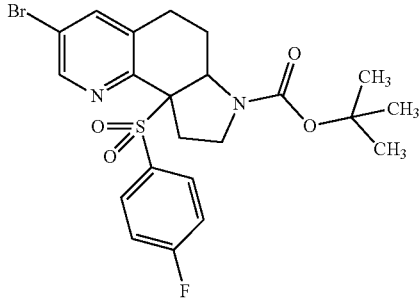 [SMILES: CC(C)(C)OC(=O)N1CCC2(S(=O)(=O)c3ccc(F)cc3)c3ncc(Br)cc3CCC12]

A solution of crude 3-bromo-9a-((4-fluorophenyl)sulfonyl)-6,6a,7,8,9,9a-hexahydro-5H-pyrrolo[2,3-h]quinoline (2.83 g) in DCM (43.3 mL) was treated sequentially with a solution of di-tert-butyl dicarbonate (1.34 mL, 5.78 mmol) in DCM (4.82 mL) and TEA (1.34 mL, 9.63 mmol). The mixture was stirred at rt for 2 h, then was partitioned between DCM and aqueous NaHCO₃. The organic phase was dried and concentrated, and the residue was subjected to column chromatography on silica gel (80 g), eluting with EtOAc-hexanes (10-20%), to provide crude racemic tert-butyl 3-bromo-9a-((4-fluorophenyl)sulfonyl)-6,6a,9,9a-tetrahydro-5H-pyrrolo[2,3-h]quinoline-7(8H)-carboxylate as a white amorphous solid (1.18 g), used without further purification. LCMS m/z 510.9. 512.9 (M+H)⁺, HPLC t_R 1.08 min (method A).

Step F: tert-butyl 9a-((4-fluorophenyl)sulfonyl)-3-(perfluoropropan-2-yl)-6,6a,9,9a-tetrahydro-5H-pyrrolo[2,3-h]quinoline-7(8H)-carboxylate (racemic)

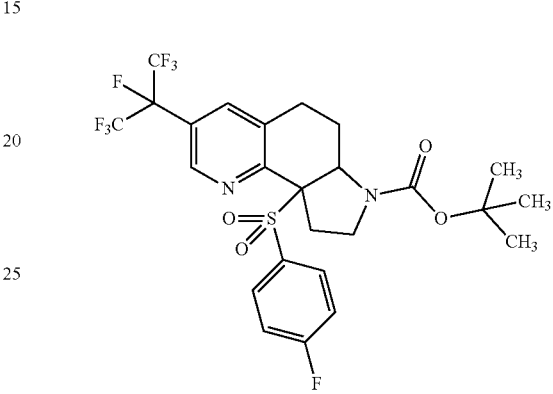

Activated copper was prepared by adding zinc dust (24.6 g, 376 mmol) portionwise with stirring to a solution of CuSO₄ pentahydrate (45.1 g, 283 mmol) in water (250 mL) over 10 min. The mixture was stirred 10 min longer, then the supernatant was decanted from the red precipitate. This was washed twice with water by decantation, then was stirred with 1 M aqueous HCl (400 mL) for 2.5 h. The supernatant was decanted and the precipitate was washed repeatedly by decantation after stirring with fresh water until the pH of the supernatant was about 7. The solid was stored under water and an inert atmosphere (nitrogen or argon). For use the solid was washed twice by decantation from MeOH, then twice by decantation from diethyl ether, and dried under vacuum.

Dried activated copper (1.68 g, 26.4 mmol) under nitrogen in a vial was treated with a solution of crude tert-butyl 3-bromo-9a-((4-fluorophenyl)sulfonyl)-6,6a,9,9a-tetrahydro-5H-pyrrolo[2,3-h]quinoline-7(8H)-carboxylate (0.900 g, 1.76 mmol) in dry DMF (11.7 mL), then with 1,1,1,2,3,3,3-heptafluoro-2-iodopropane (1.13 mL, 7.92 mmol). The vial was sealed under nitrogen and stirred on a heating block at 120° C. After 3 h, the mixture was cooled to rt, filtered through Celite, and the solids were washed with EtOAc. The combined filtrates were partitioned between EtOAc and saturated aqueous NaHCO₃. The organic phase was washed sequentially with 10% aqueous LiCl and brine, dried and concentrated to provide crude racemic tert-butyl 9a-((4-fluorophenyl)sulfonyl)-3-(perfluoropropan-2-yl)-6,6a,9,9a-tetrahydro-5H-pyrrolo[2,3-h]quinoline-7(8H)-carboxylate as a brown syrup (1.63 g), used without further purification. LCMS m/z 601.1 (M+H)⁺, HPLC t_R 1.17 min (method A).

Step G: 9a-((4-fluorophenyl)sulfonyl)-3-(perfluoropropan-2-yl)-6,6a,7,8,9,9a-hexahydro-5H-pyrrolo[2,3-h]quinoline dihydrochloride, Single Enantiomer

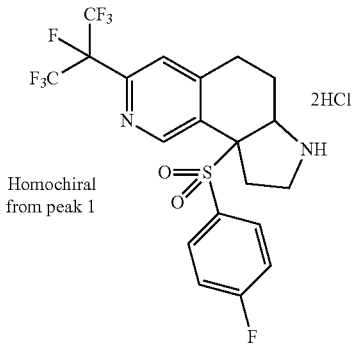 [SMILES: O=S(=O)(c1ccc(F)cc1)C12CCNC1CCc1cc(C(F)(C(F)(F)F)C(F)(F)F)ncc12]

Homochiral from peak 1

A sample of crude tert-butyl 9a-((4-fluorophenyl)sulfonyl)-3-(perfluoropropan-2-yl)-6,6a,9,9a-tetrahydro-5H-pyrrolo[2,3-h]quinoline-7(8H)-carboxylate (2.36 g) was separated by preparative SFC using the following conditions: column: (R,R)Whelk-O1 5×50 cm, 10 μm (Phenomenex Inc.); column temperature 35° C.; mobile phase: $CO_2$-IPA (90:10) with 0.1% $NH_4OH$; flow rate 300 mL/min; pressure 100 bar; sample injection: 0.8 mL, 75 mg/mL in DMF-IPA. The first-eluted peaks from all injections were combined and concentrated to provided a yellow solid. This was dissolved in DCM (13 mL) and THF (4 mL) and treated with HCl (4 M in dioxane; 1.92 mL, 7.66 mmol) and TFA (0.984 mL, 12.8 mmol). After 6 h, the mixture was partitioned between DCM and a mixture of 1.5 M aqueous $K_2HPO_4$ and 1 M aqueous NaOH. The organic phase was washed with brine, dried and concentrated. The residue was dissolved in DCM, treated with HCl (4 M in dioxane), and the solution was concentrated to provide a single enantiomer of 9a-((4-fluorophenyl)sulfonyl)-3-(perfluoropropan-2-yl)-6,6a,7,8,9,9a-hexahydro-5H-pyrrolo[2,3-h]quinoline dihydrochloride as a light yellow solid (0.49 g). LCMS m/z 501.1 (M+H)$^+$, HPLC $t_R$ 0.84 min (method A). $^1$H NMR (499 MHz, DMSO-$d_6$) δ 10.10-9.57 (m, 2H), 8.53 (d, J=1.7 Hz, 1H), 8.08 (s, 1H), 7.44-7.38 (m, 2H), 7.35-7.29 (m, 2H), 4.85 (dd, J=11.0, 6.8 Hz, 1H), 3.46 (dd, J=8.4, 5.6 Hz, 2H), 3.13-2.97 (m, 2H), 2.82 (dt, J=14.9, 8.5 Hz, 1H), 2.75-2.63 (m, 1H), 2.58-2.53 (m, 1H), 1.87-1.75 (m, 1H). The absolute configuration was not determined.

Intermediate 2

3-(benzyloxy)-9a-((4-fluorophenyl)sulfonyl)-6,6a,7,8,9,9a-hexahydro-5H-pyrrolo[2,3-h]isoquinoline (single enantiomer)

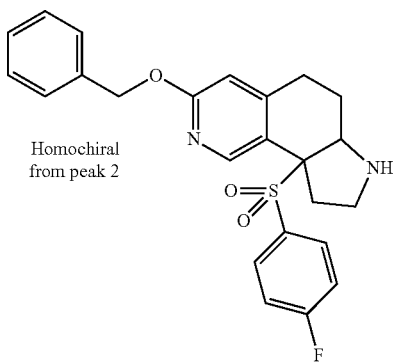 [SMILES: O=S(=O)(c1ccc(F)cc1)C12CCNC1CCc1cc(OCc3ccccc3)ncc12]

Homochiral from peak 2

Step A:
3-(benzyloxy)-6,7-dihydroisoquinolin-8(5H)-one

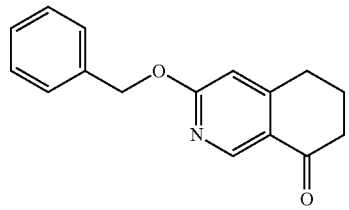 [SMILES: O=C1CCCc2cc(OCc3ccccc3)ncc21]

A mixture of 3-hydroxy-6,7-dihydroisoquinolin-8(5H)-one (1.94 g, 11.9 mmol), $Ag_2CO_3$ (3.28 g, 11.9 mmol) and benzyl bromide (2.55 mL, 21.4 mmol) in toluene (23.8 mL) was stirred at rt overnight. After 18 h, the mixture was filtered through Celite and the filtrate was concentrated. The residue was subjected to column chromatography on silica gel (40 g), eluting with EtOAc-hexanes (5-15%), to provide 3-(benzyloxy)-6,7-dihydro-isoquinolin-8(5H)-one as a white solid (2.93 g, 97% yield). LCMS m/z 254.1 (M+H)$^+$, HPLC $t_R$ 0.97 min (method A). $^1$H NMR (400 MHz, CDCl$_3$) δ 8.86 (s, 1H), 7.48-7.43 (m, 2H), 7.41-7.31 (m, 3H), 6.63 (d, J=0.4 Hz, 1H), 5.46 (s, 2H), 2.89 (t, J=6.2 Hz, 2H), 2.68-2.61 (m, 2H), 2.12 (quin, J=6.4 Hz, 2H).

Step B: 3-(benzyloxy)-5,6-dihydroisoquinolin-8-yl trifluoromethanesulfonate

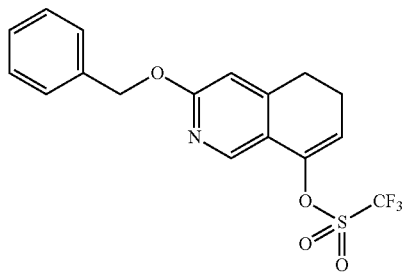 [SMILES: O=S(=O)(OC1=CCCc2cc(OCc3ccccc3)ncc21)C(F)(F)F]

A solution of 3-(benzyloxy)-6,7-dihydroisoquinolin-8(5H)-one (2.61 g, 10.3 mmol) and N,N-bis(trifluoromethylsulfonyl)aniline (4.79 g, 13.4 mmol) in THF (57.2 mL) was stirred at −78° C. and treated dropwise with a solution of potassium bis(trimethylsilyl)amide (1.0 M in THF; 13.9 mL, 13.9 mmol). After 1 h, the mixture was treated with water and warmed to rt. The mixture was treated with saturated aqueous NaHCO$_3$ and extracted with diethyl ether. The organic phase was washed with brine, dried and concentrated. The residue was subjected to column chromatography on silica gel (40 g), eluting with EtOAc-hexanes (0-5%), to provide 3-(benzyloxy)-5,6-dihydroisoquinolin-8-yl trifluoromethanesulfonate as a light yellow oil (4.12 g, quantitative yield). LCMS m/z 386.0 (M+H)$^+$, HPLC $t_R$ 1.19 min (method A). $^1$H NMR (499 MHz, CDCl$_3$) δ ppm 8.15 (s, 1H), 7.45-7.49 (m, 2H), 7.38-7.42 (m, 2H), 7.33-7.37 (m, 1H), 6.66 (d, J=0.6 Hz, 1H), 5.96 (t, J=4.8 Hz, 1H), 5.42 (s, 2H), 2.81-2.90 (m, 2H), 2.54 (td, J=8.0, 4.8 Hz, 2H).

Step C: 3-(benzyloxy)-8-((4-fluorophenyl)thio)-5,6-dihydroisoquinoline

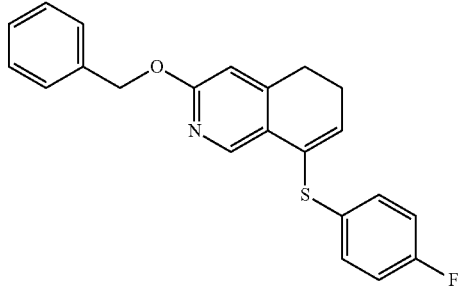 [SMILES: Fc1ccc(SC2=CCCc3cc(OCc4ccccc4)ncc32)cc1]

A mixture of 3-(benzyloxy)-5,6-dihydroisoquinolin-8-yl trifluoromethanesulfonate (2.89 g, 7.50 mmol), Xantphos (0.456 g, 0.787 mmol), $Pd_2(dba)_3$ (0.412 g, 0.450 mmol), 4-fluorobenzenethiol (2.00 mL, 18.8 mmol), and DIEA (2.62 mL, 15.0 mmol) in 1,4-dioxane (25 mL) was bubbled with nitrogen, then was heated in a sealed tube at 120° C. After 2 h the mixture was cooled to rt and filtered through Celite. The solids were washed with water and ether, and the combined filtrates were partitioned between saturated aqueous $NaHCO_3$ and ether. The organic phase was washed with brine, dried and concentrated. The residue was subjected to column chromatography on silica gel (120 g), eluting with EtOAc-hexanes (0-5%), to provide 3-(benzyloxy)-8-((4-fluorophenyl)thio)-5,6-dihydroisoquinoline as a colorless syrup (2.10 g, 77% yield). LCMS m/z 364.1 (M+H)$^+$, HPLC $t_R$ 1.21 min (method A). $^1$H NMR (499 MHz, $CDCl_3$) δ 8.30 (s, 1H), 7.43-7.47 (m, 2H), 7.37-7.41 (m, 2H), 7.29-7.35 (m, 3H), 6.99 (t, J=8.8 Hz, 2H), 6.62 (d, J=0.6 Hz, 1H), 6.37 (t, J=4.6 Hz, 1H), 5.37 (s, 2H), 2.80-2.87 (m, 2H), 2.45 (td, J=7.8, 4.7 Hz, 2H).

Step D: 3-(benzyloxy)-8-((4-fluorophenyl)sulfonyl)-5,6-dihydroisocuinoline

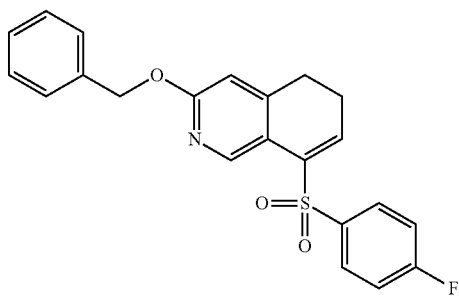 [SMILES: O=S(=O)(C1=CCCc2cc(OCc3ccccc3)ncc21)c1ccc(F)cc1]

A solution of 3-(benzyloxy)-8-((4-fluorophenyl)thio)-5,6-dihydroisoquinoline (2.10 g, 5.78 mmol) in DCM (108 mL) was cooled to 0° C. and treated with a solution of mCPBA (3.24 g, 14.4 mmol) in DCM (36 mL). After stirring for 3 h, the mixture was partitioned between DCM and saturated aqueous $NaHCO_3$. The organic phase was washed sequentially with aqueous $Na_2S_2O_3$ and brine, dried and concentrated to give 3-(benzyloxy)-8-((4-fluorophenyl)sulfonyl)-5,6-dihydroisoquinoline as a light pink amorphous solid (2.17 g, 95% yield). LCMS m/z 396.1 (M+H)$^+$, HPLC $t_R$ 1.06 min (method A).

Step E: 2-((3-(benzyloxy)-8-((4-fluorophenyl)sulfonyl)-5,6,7,8-tetrahydroisoquinolin-7-yl)amino)ethanol

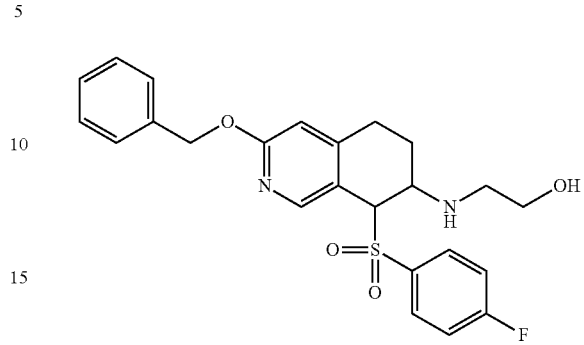

A solution of 3-(benzyloxy)-8-((4-fluorophenyl)sulfonyl)-5,6-dihydroisoquinoline (2.17 g, 5.05 mmol) in THF (50.5 mL) was stirred on an ice-water bath and treated with 2-aminoethanol (1.83 mL, 30.3 mmol). The mixture was stirred at rt for 3.5 h, then was partitioned between saturated aqueous $NaHCO_3$ and EtOAc. The organic phase was washed with brine, dried and concentrated to provide crude 2-((3-(benzyloxy)-8-((4-fluorophenyl)sulfonyl)-5,6,7,8-tetrahydroisoquinolin-7-yl)amino)ethanol as a dark yellow amorphous solid (2.24 g, estimated purity 70%), used without further purification. LCMS m/z 457.1 (M+H)$^+$, HPLC $t_R$ 0.77 min (method A).

Step F: 3-(benzyloxy)-9a-((4-fluorophenyl)sulfonyl)-6,6a,7,8,9,9a-hexahydro-5H-pyrrolo[2,3-h]isoquinoline (racemic)

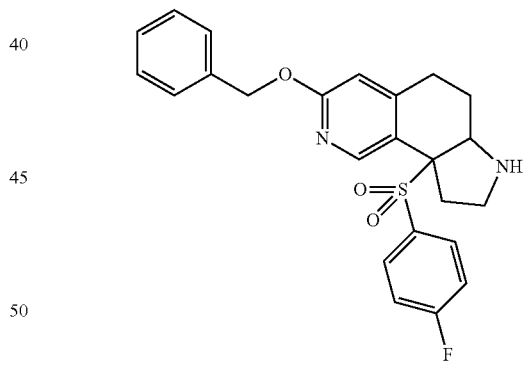

A solution of crude 2-((3-(benzyloxy)-8-((4-fluorophenyl)sulfonyl)-5,6,7,8-tetrahydroisoquinolin-7-yl)amino) ethanol (2.24 g) in DCM (114 mL), stirred on an ice-water bath, was treated sequentially with MsCl (0.308 mL, 3.95 mmol) and TEA (0.551 mL, 3.95 mmol). The mixture was stirred at 0° C. for 45 min, then was treated with additional MsCl (40 μL, 0.15 equiv.). After 2 h total, a solution of potassium tert-butoxide (1.93 g, 17.2 mmol) in THF (12 mL) was added slowly, stirred at 0° C. for 5 min, then warmed to rt. After 2 h, the mixture was diluted with aqueous $NaHCO_3$ and extracted with DCM (3 times). The organic phase was washed with brine, dried and concentrated. The residue was subjected to column chromatography on silica gel (40 g), eluting with EtOAc-hexanes (50-100%), then with 5%

MeOH-EtOAc, to provide racemic 3-(benzyloxy)-9a-((4-fluorophenyl)sulfonyl)-6,6a,7,8,9,9a-hexahydro-5H-pyrrolo[2,3-h]isoquinoline as brown amorphous solid (0.967 g, 64% yield). LCMS m/z 439.1 (M+H)$^+$, HPLC $t_R$ 0.79 min (method A).

Step G: 3-(benzyloxy)-9a-((4-fluorophenyl)sulfonyl)-6,6a,7,8,9,9a-hexahydro-5H-pyrrolo[2,3-h]isoquinoline (Single Enantiomer)

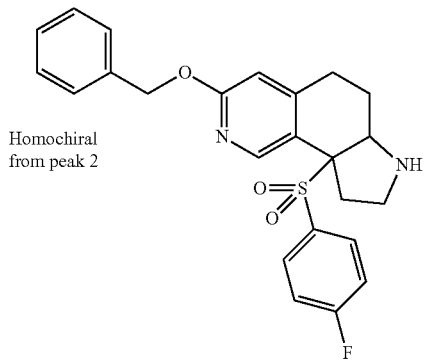 [SMILES: O=S(=O)(c1ccc(F)cc1)C12CCNC1CCc1cc(OCc3ccccc3)ncc12]

Homochiral from peak 2

A sample of racemic 3-(benzyloxy)-9a-((4-fluorophenyl)sulfonyl)-6,6a,7,8,9,9a-hexahydro-5H-pyrrolo[2,3-h]isoquinoline (0.96 g) was separated by preparative SFC using the following conditions: column: (R,R)Whelk-O1 3×25 cm, 10 μm (Phenomenex Inc.); column temperature 40° C.; mobile phase: CO$_2$-MeOH-water (60:38:2) with 2% DCM; flow rate 150 mL/min; pressure 100 bar; sample injection: 1 mL, 32 mg/mL in 2:1 MeOH-DCM. The second-eluted peaks from all injections were combined and concentrated to provide a single enantiomer of 3-(benzyloxy)-9a-((4-fluorophenyl)-sulfonyl)-6,6a,7,8,9,9a-hexahydro-5H-pyrrolo[2,3-h]isoquinoline as a yellow solid (0.368 g, 38% yield). LCMS m/z 439.1 (M+H)$^+$, HPLC $t_R$ 0.79 min (method A). The absolute configuration was not determined.

Intermediate 3

Mixture of 7-((2,6-dichlorobenzyl)oxy)-9b-((4-fluorophenyl)sulfonyl)-2,3,3a,4,5,9b-hexahydro-1H-pyrrolo[3,2-f]quinoline dihydrochloride (single enantiomer) and 9b-((4-fluorophenyl)sulfonyl)-2,3,3a,4,5,9b-hexahydro-1H-pyrrolo[3,2-f]quinolin-7-ol dihydrochloride (Single Enantiomer)

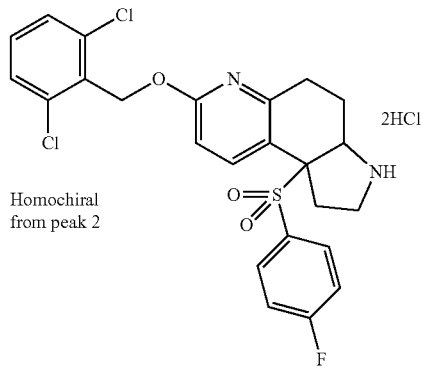

Homochiral from peak 2

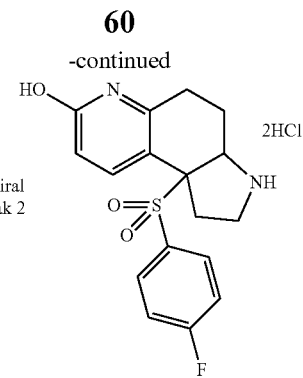

Homochiral from peak 2

Step A: 2-((2,6-dichlorobenzyl)oxy)-7,8-dihydroquinolin-5(6H)-one

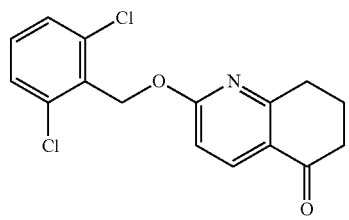 [SMILES: O=C1CCCc2nc(OCc3c(Cl)cccc3Cl)ccc21]

A solution of (2,6-dichlorophenyl)methanol (1.07 g, 6.06 mmol) in DMF (15 mL) was treated with NaH (60% in mineral oil; 661 mg, 16.5 mmol) and stirred at rt for 15 min. The mixture was treated with 2-chloro-7,8-dihydroquinolin-5(6H)-one (1.00 g, 5.51 mmol) and stirred at rt for 1.5 h. Chipped ice (5 g) was added and the mixture was extracted twice with EtOAc. The combine organic phases were washed with brine, dried and concentrated. The residue was subjected to column chromatography on silica gel, eluting with EtOAc-hexanes (0-40%), to provide 2-((2,6-dichlorobenzyl)oxy)-7,8-dihydroquinolin-5(6H)-one (1.35 g, 76% yield). LCMS m/z 321.8, 323.8, 325.8 (M+H)$^+$, HPLC $t_R$ 3.71 min (method B). $^1$H NMR (400 MHz, CDCl$_3$) δ 8.21 (d, J=8.58 Hz, 1H), 7.37-7.44 (m, 2H), 7.20-7.33 (m, 1H), 6.71 (d, J=8.58 Hz, 1H), 5.69 (s, 2H), 3.09 (t, J=6.16 Hz, 2H), 2.62-2.70 (m, 2H), 2.14-2.28 (m, 2H).

Alternative procedure: A mixture of 2-hydroxy-7,8-dihydroquinolin-5(6H)-one (8.65 g, 53.0 mmol), 2-(bromomethyl)-1,3-dichlorobenzene (15.26 g, 63.6 mmol), and Cs$_2$CO$_3$ (17.3 g, 53.0 mmol) in MeCN (200 mL) was stirred at rt. After 2 days, the mixture was filtered and the filtrates were concentrated. The residue was subjected to column chromatography on silica gel to provide 2-((2,6-dichlorobenzyl)oxy)-7,8-dihydroquinolin-5(6H)-one as a white solid (14.5 g, 85% yield).

Step B: 2-((2,6-dichlorobenzyl)oxy)-7,8-dihydroquinolin-5-yl trifluoromethanesulfonate

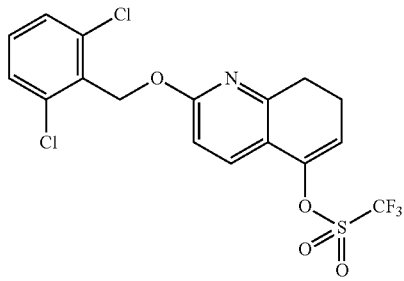 [SMILES: O=S(=O)(OC1=CCCc2nc(OCc3c(Cl)cccc3Cl)ccc21)C(F)(F)F]

A solution of 2-((2,6-dichlorobenzyl)oxy)-7,8-dihydroquinolin-5(6H)-one (1.34 g, 4.16 mmol) in DCM (25 mL) was treated with trifluoromethanesulfonic anhydride (1.29 g, 4.57 mmol) and 2-chloropyridine (0.519 g, 4.57 mmol). The mixture was stirred at rt for 2.5 h, then was diluted with DCM (50 mL), washed sequentially with saturated aqueous NaHCO$_3$ and brine, dried and concentrated. The residue was subjected to column chromatography on silica gel, eluting with EtOAc-hexanes (0-50%), to provide 2-((2,6-dichlorobenzyl)oxy)-7,8-dihydroquinolin-5-yl trifluoromethanesulfonate (1.36 g, 72% yield). LCMS m/z 453.7, 455.7, 457.7 (M+H)$^+$, HPLC t$_R$ 4.27 min (method B). $^1$H NMR (400 MHz, CDCl$_3$) δ 7.55 (d, J=8.6 Hz, 1H), 7.34-7.42 (m, 2H), 7.23-7.28 (m, 1H), 6.69 (d, J=8.6 Hz, 1H), 5.94 (t, J=4.7 Hz, 1H), 5.63 (s, 2H), 3.04 (t, J=8.6 Hz, 2H), 2.63 (td, J=8.6, 4.8 Hz, 2H).

Alternative procedure: Using the procedure of Intermediate 2, Step B, 2-((2,6-dichlorobenzyl)oxy)-7,8-dihydroquinolin-5(6H)-one was converted to 2-((2,6-dichlorobenzyl)oxy)-7,8-dihydroquinolin-5-yl trifluoromethanesulfonate in quantitative yield.

Step C: 2-((2,6-dichlorobenzyl)oxy)-5-((4-fluorophenyl)thio)-7,8-dihydroquinoline

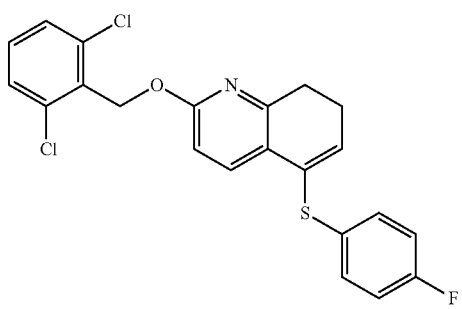 [SMILES: Fc1ccc(SC2=CCCc3nc(OCc4c(Cl)cccc4Cl)ccc32)cc1]

A solution of 4-fluorobenzenethiol (0.499 g, 3.89 mmol) in THF (15 mL) was treated with n-butyllithium (2.0 M in hexanes; 2.25 mL, 4.49 mmol). The mixture was stirred at rt for 10 min, then was added to a mixture of 2-((2,6-dichlorobenzyl)oxy)-7,8-dihydroquinolin-5-yl trifluoromethanesulfonate (1.36 g, 2.99 mmol), LiCl (0.279 g, 6.59 mmol) and tetrakis(triphenylphosphine)palladium (0.346 g, 0.299 mmol) in THF (5 mL) in a vial. The vial was sealed and heated at reflux. After 2.5 h, additional n-butyllithium solution (2.25 mL, 4.49 mmol) was added and heating was continued. After 4 h total, the mixture was cooled to rt and treated with water. The mixture was extracted 3 times with EtOAc. The combined organic phases were washed with brine, dried and concentrated. The residue was subjected to column chromatography on silica gel, eluting with EtOAc-hexanes (0-50%), to give 2-((2,6-dichlorobenzyl)oxy)-5-((4-fluorophenyl)thio)-7,8-dihydroquinoline (0.90 g, 95% pure, 66% yield). LCMS m/z 431.8, 433.7, 435.7 (M+H)$^+$, HPLC t$_R$ 4.39 min (method B).

Step D: tert-butyl 7-((2,6-dichlorobenzyl)oxy)-9b-((4-fluorophenyl)sulfonyl)-3a,4,5,9b-tetrahydro-1H-pyrrolo[3,2-f]quinoline-3(2H)-carboxylate (racemic)

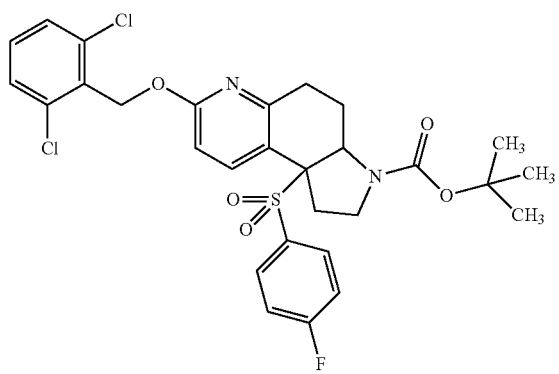 [SMILES: CC(C)(C)OC(=O)N1CCC2(S(=O)(=O)c3ccc(F)cc3)c3ccc(OCc4c(Cl)cccc4Cl)nc3CCC12]

Following the procedures of Intermediate 1, Steps B through E, 2-((2,6-dichlorobenzyl)oxy)-5-((4-fluorophenyl)thio)-7,8-dihydroquinoline (0.900 g, 2.08 mmol) was converted into racemic tert-butyl 7-((2,6-dichlorobenzyl)oxy)-9b-((4-fluorophenyl)sulfonyl)-3a,4,5,9b-tetrahydro-1H-pyrrolo[3,2-f]quinoline-3(2H)-carboxylate (330 mg). LCMS m/z 606.7, 608.7, 610.7 (M+H)$^+$, HPLC t$_R$ 4.00 min (method B).

Step E: Mixture of 7-((2,6-dichlorobenzyl)oxy)-9b-((4-fluorophenyl)sulfonyl)-2,3,3a,4,5,9b-hexahydro-1H-pyrrolo[3,2-f]quinoline dihydrochloride (single enantiomer) and 9b-((4-fluorophenyl)sulfonyl)-2,3,3a,4,5,9b-hexahydro-1H-pyrrolo[3,2-f]quinolin-7-ol (Single Enantiomer)

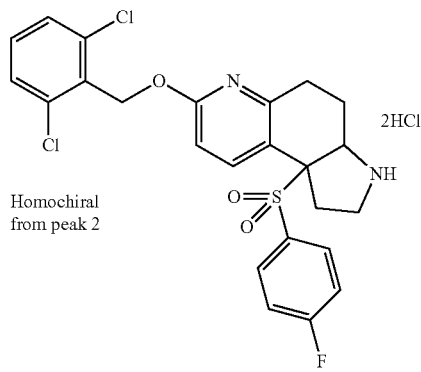

Homochiral from peak 2

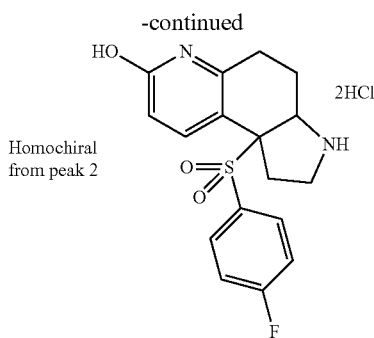

Homochiral from peak 2

A sample of racemic tert-butyl 7-((2,6-dichlorobenzyl)oxy)-9b-((4-fluorophenyl)sulfonyl)-3a,4,5,9b-tetrahydro-1H-pyrrolo[3,2-f]quinoline-3(2H)-carboxylate (330 mg) was separated by preparative SFC using the following conditions: column: Cellulose-4 3×25 cm, 5 μm; column temperature 35° C.; mobile phase: $CO_2$—MeOH (60:40); flow rate 200 mL/min; pressure 100 bar. The second-eluted peaks from all injections were combined and concentrated to provided a solid (150 mg). A sample of this material (105 mg, 0.173 mmol) was dissolved in DCM (1.7 mL), treated with HCl (4 M in dioxane; 0.34 mL, 1.38 mmol) and stirred at rt for 2.5 h. The solution was concentrated to provide a mixture of a single enantiomer of 7-((2,6-dichlorobenzyl)oxy)-9b-((4-fluorophenyl)sulfonyl)-2,3,3a,4,5,9b-hexahydro-1H-pyrrolo[3,2-J]quinoline dihydrochloride [LCMS m/z 507.0, 509.0, 511.7 (M+H)$^+$, HPLC $t_R$ 0.88 min (method A)] and the corresponding single enantiomer of 9b-((4-fluorophenyl)sulfonyl)-2,3,3a,4,5,9b-hexahydro-1H-pyrrolo[3,2-f]quinolin-7-ol dihydrochloride [LCMS m/z 349.0 (M+H)$^+$, HPLC $t_R$ 0.49 min (method A)], ratio by HPLC (220 nM) 38:62, as a light yellow solid (101 mg), which was used without further purification. The absolute configuration was not determined.

Intermediate 4

7-(perfluoropropan-2-yl)-9b-(phenylsulfonyl)-2,3,3a,4,5,9b-hexahydro-1H-pyrrolo[3,2-f]quinoline (Single Enantiomer)

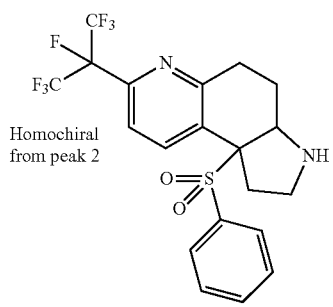 [SMILES: O=S(=O)(c1ccccc1)C12CCNC1CCc1nc(C(F)(C(F)(F)F)C(F)(F)F)ccc12]

Homochiral from peak 2

Step A: 2-((2,6-dichlorobenzyl)oxy)-5-(phenylthio)-78-dihydroquinoline

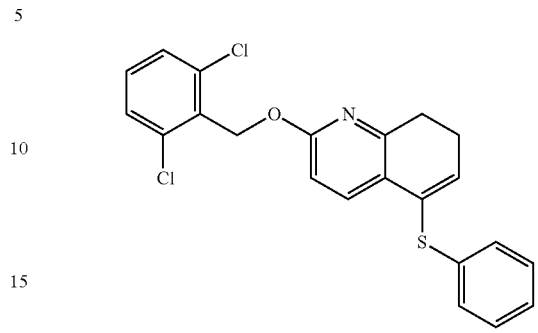

Following the procedure of Intermediate 2, Step C, 2-((2,6-dichlorobenzyl)oxy)-7,8-dihydroquinolin-5-yl trifluoromethanesulfonate (Intermediate 3, Step B) was converted to 2-((2,6-dichlorobenzyl)oxy)-5-(phenylthio)-7,8-dihydroquinoline as a yellow solid in 89% yield. LCMS m/z 414.0, 416.0 (M+H)+, HPLC $t_R$ 1.36 min (method A). $^1$H NMR (499 MHz, CDCl$_3$) δ 7.68 (d, J=8.5 Hz, 1H), 7.39-7.35 (m, 2H), 7.27-7.22 (m, 5H), 7.17-7.12 (m, 1H), 6.54-6.49 (m, 2H), 5.60 (s, 2H), 3.05 (t, J=8.4 Hz, 2H), 2.60 (td, J=8.4, 4.6 Hz, 2H).

Step B: 7-((2,6-dichlorobenzyl)ox)-9b-(phenylsulfonyl)-2,3,3a,4,5,9b-hexahydro-1H-pyrrolo[3,2-f]quinoline (racemic)

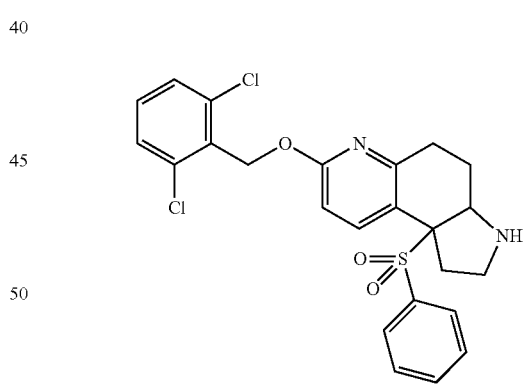

Following the procedures of Intermediate 1, Steps B through D, 2-((2,6-dichlorobenzyl)oxy)-5-(phenylthio)-7,8-dihydroquinoline was converted to racemic 7-((2,6-dichlorobenzyl)oxy)-9b-(phenylsulfonyl)-2,3,3a,4,5,9b-hexahydro-1H-pyrrolo[3,2-J]quinoline, used without further purification. LCMS m/z 489.1, 491.0, (M+H)$^+$, HPLC $t_R$ 0.83 min (method A).

Step C: 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one (racemic)

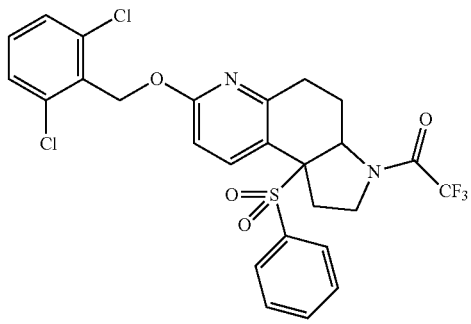 [SMILES: O=C(N1CCC2(S(=O)(=O)c3ccccc3)c3ccc(OCc4c(Cl)cccc4Cl)nc3CCC12)C(F)(F)F]

A solution of 7-((2,6-dichlorobenzyl)oxy)-9b-(phenylsulfonyl)-2,3,3a,4,5,9b-hexahydro-1H-pyrrolo[3,2-]quinoline (8.51 g, 17.4 mmol) in DCM (58.0 mL), cooled on an ice-water bath, was treated with pyridine (5.06 mL, 62.6 mmol), then with trifluoroacetic anhydride (3.87 mL, 27.8 mmol). The mixture was stirred at rt for 2 h, then was diluted with DCM, washed sequentially with saturated aqueous NaHCO$_3$ and brine, dried and concentrated. The residue was subjected to column chromatography on silica gel (120 g), eluting with EtOAc-hexanes (10-25%), to provide racemic 1-(7-((2,6-dichlorobenzyl)oxy)-9b-(phenylsulfonyl)-1,2,3a,4,5,9b-hexahydro-3H-pyrrolo[3,2-J]quinolin-3-yl)-2,2,2-trifluoroethan-1-one (7.02 g, 69% yield). LCMS m/z 585.1, 587.1 (M+H)+, HPLC $t_R$ 1.17 min (method A).

Step D: 1-(7-((2,6-dichlorobenzyl)oxy)-9b-(phenylsulfonyl)-1,2,3a,4,5,9b-hexahydro-3H-pyrrolo[32-f]quinolin-3-yl)-2,2,2-trifluoroethan-1-one (Single Enantiomer)

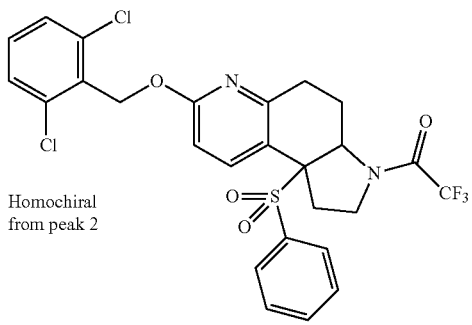 [SMILES: O=C(N1CCC2(S(=O)(=O)c3ccccc3)c3ccc(OCc4c(Cl)cccc4Cl)nc3CCC12)C(F)(F)F]

Homochiral from peak 2

A sample of racemic 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one (7.02 g) was separated by preparative SFC using the following conditions: column: Cellulose-4 3×25 cm, 5 μm; column temperature 35° C.; mobile phase: CO$_2$-MeOH (60:40); flow rate 200 mL/min; pressure 100 bar. The second-eluted peaks from all injections were combined and concentrated to provided a single enantiomer of 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one as a white solid (2.70 g, 39% yield). LCMS m/z 585.3, 587.3 (M+H)+, HPLC $t_R$ 2.593 min (method C). $^1$H NMR (500 MHz, DMSO-d$_6$) δ 7.91 (d, J=8.5 Hz, 1H), 7.80-7.71 (m, 1H), 7.60-7.44 (m, 5H), 7.40 (br d, J=7.6 Hz, 2H), 6.86 (d, J=8.9 Hz, 1H), 5.45 (s, 2H), 4.74 (br dd, J=11.6, 4.6 Hz, 1H), 3.95-3.76 (m, 2H), 3.42-3.34 (m, 2H), 2.72 (dt, J=14.6, 9.0 Hz, 1H), 2.34-2.21 (m, 1H), 1.98 (br t, J=13.6 Hz, 1H), 1.64-1.49 (m, 1H). The first-eluted peaks from all injections were combined and concentrated to provide the other enantiomer of 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one as a white solid (2.59 g, 37% yield). LCMS m/z 585.2, 587.2 (M+H)+, HPLC $t_R$ 2.54 min (method C). The absolute configurations of the enantiomers were not determined.

Step E: 2,2,2-trifluoro-1-(7-hydroxy-9b-(phenylsulfonyl)-1,2,3a,4,5,9b-hexahydro-3H-pyrrolo 3,2-fl quinolin-3-yl)ethan-1-one (Single Enantiomer)

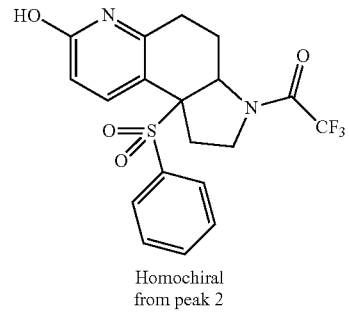 [SMILES: O=C(N1CCC2(S(=O)(=O)c3ccccc3)c3ccc(O)nc3CCC12)C(F)(F)F]

Homochiral from peak 2

A mixture of a single enantiomer of 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one (2.59 g, 4.42 mmol) and 5% Pd on carbon (0.471 g, 0.221 mmol) in MeOH-EtOAc (1:1, 101 mL) was stirred under a hydrogen atmosphere (balloon pressure) for 20 h. The mixture was filtered and the filtrates were concentrated to provide a single enantiomer of 2,2,2-trifluoro-1-(7-hydroxy-9b-(phenylsulfonyl)-1,2,3a,4,5,9b-hexahydro-3H-pyrrolo[3,2-f]quinolin-3-yl)ethan-1-one as an off-white solid in quantitive yield. LCMS m/z 427.1 (M+H)+, HPLC $t_R$ 0.74 min (method A).

Step F: 1-(7-bromo-9b-(phenylsulfonyl)-1,2,3a,4,5,9b-hexahydro-3H-pyrrolo[3,2-f]quinolin-3-yl)-2,2,2-trifluoroethan-1-one (Single Enantiomer)

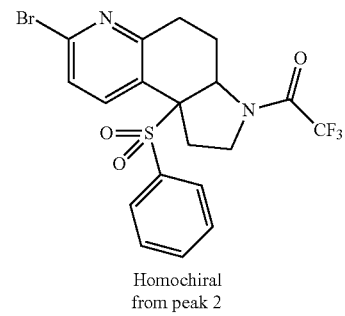 [SMILES: O=C(N1CCC2(S(=O)(=O)c3ccccc3)c3ccc(Br)nc3CCC12)C(F)(F)F]

Homochiral from peak 2

A suspension of a single enantiomer of 2,2,2-trifluoro-1-(7-hydroxy-9b-(phenylsulfonyl)-1,2,3a,4,5,9b-hexahydro-3H-pyrrolo[3,2-f]quinolin-3-yl)ethan-1-one (2.08 g, 4.39 mmol, 90% pure) in MeCN (16.3 mL) was treated with a solution of phosphorus oxybromide (3.27 g, 11.4 mmol) in anisole (8.13 mL). The resulting solution was heated at 90° C., gradually forming a suspension. After 5 h the mixture was cooled to rt, then poured on ice and neutralized with 1 M aqueous NaOH (35 mL, 35 mmol), followed by saturated aqueous $NaHCO_3$. The mixture was extracted with ether, and the organic phase was washed with brine, dried and concentrated. The residue was subjected to column chromatography on silica gel (80 g), eluting with EtOAc-hexanes (5-50%), to provide a single enantiomer of 1-(7-bromo-9b-(phenylsulfonyl)-1,2,3a,4,5,9b-hexahydro-3H-pyrrolo[3,2-J]quinolin-3-yl)-2,2,2-trifluoroethan-1-one (1.73 g, 81% yield). LCMS m/z 489.0, 491.0 $(M+H)^+$, HPLC $t_R$ 0.96 min (method A).

Step G: 2,2,2-trifluoro-1-(7-(perfluoropropan-2-yl)-9b-(phenylsulfonyl)-1,2,3a,4,5,9b-hexahydro-3H-pyrrolo[3,2-f]quinolin-3-yl)ethan-1-one (Single Enantiomer)

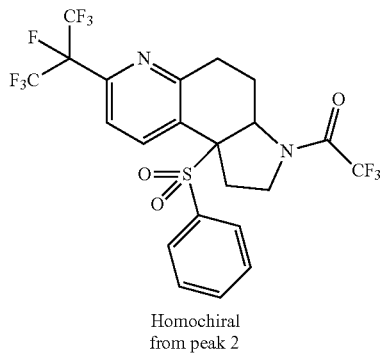 [SMILES: O=C(N1CCC2(S(=O)(=O)c3ccccc3)c3ccc(C(F)(C(F)(F)F)C(F)(F)F)nc3CCC12)C(F)(F)F]

Homochiral from peak 2

Following the procedure used to prepare Intermediate 1, Step F, a single enantiomer of 1-(7-bromo-9b-(phenylsulfonyl)-1,2,3a,4,5,9b-hexahydro-3H-pyrrolo[3,2-J]quinolin-3-yl)-2,2,2-trifluoroethan-1-one was converted to a single enantiomer of 2,2,2-trifluoro-1-(7-(perfluoropropan-2-yl)-9b-(phenylsulfonyl)-1,2,3a,4,5,9b-hexahydro-3H-pyrrolo[3,2-f]quinolin-3-yl)ethan-1-one as a light yellow sticky solid in quantitve yield, purity about 85%, which was used without further purification. LCMS m/z 579.2 $(M+H)^+$, HPLC $t_R$ 1.13 min (method A).

Step H: 7-(perfluoropropan-2-yl)-9b-(phenylsulfonyl)-2,3,3a,4,5,9b-hexahydro-1H-pyrrolo[3,2-f]quinoline (Single Enantiomer)

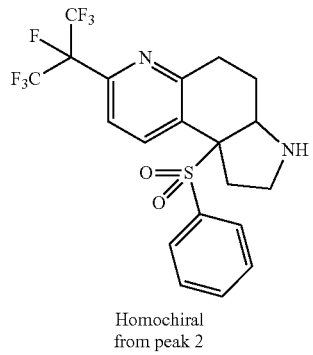 [SMILES: O=S(=O)(c1ccccc1)C12CCNC1CCc1nc(C(F)(C(F)(F)F)C(F)(F)F)ccc12]

Homochiral from peak 2

A solution of a single enantiomer of 2,2,2-trifluoro-1-(7-(perfluoropropan-2-yl)-9b-(phenylsulfonyl)-1,2,3a,4,5,9b-hexahydro-3H-pyrrolo[3,2-f]quinolin-3-yl)ethan-1-one (2.41 g, 3.54 mmol, 85% pure) in THF (23.6 mL) was treated with LiOH hydrate (1.19 g, 28.3 mmol) and water (11.8 mL). The mixture was heated at 85° C. for 3.5 h, then was cooled to rt. The mixture was diluted with EtOAc, washed sequentially with water and brine, dried and concentrated to provide a single enantiomer of 7-(perfluoropropan-2-yl)-9b-(phenylsulfonyl)-2,3,3a,4,5,9b-hexahydro-1H-pyrrolo[3,2-J]quinoline as a light yellow solid (1.64 g, 96% yield). LCMS m/z 483.2 $(M+H)^+$, HPLC $t_R$ 0.81 min (method A).

The following intermediates were prepared according to the procedures used to prepare Intermediate 4 or similar procedures.

TABLE 1

| Intermediate | Structure | LCMS m/z observed | HPLC $t_R$ (min) | HPLC method |
|---|---|---|---|---|
| 5 | CF₃, F, F₃C, N, O=S=O, NH, F (Homochiral from peak 2) | 501.1 $(M + H)^+$ | 0.83 | A |

TABLE 1-continued

| Intermediate | Structure | LCMS m/z observed | HPLC $t_R$ (min) | HPLC method |
|---|---|---|---|---|
| 6 | Homochiral from peak 1 | 501.1 (M + H)⁺ | 0.87 | A |
| 7 | Homochiral from peak 2 | 501.1 (M + H)⁺ | 0.87 | A |
| 8 | Homochiral from peak 2 | 501.0 (M + H)⁺ | 0.84 | A |
| 9 | Homochiral from peak 2 | 501.1 (M + H)⁺ | 0.83 | A |

Intermediate 10

(S)-1-(4-fluorobenzyl)-5-oxopyrrolidine-2-carboxylic acid

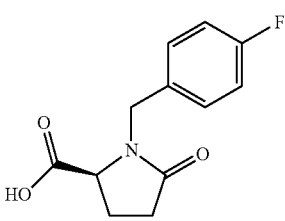 [SMILES: O=C(O)[C@@H]1CCC(=O)N1Cc1ccc(F)cc1]

A suspension of NaH (60% in mineral oil; 0.336 g, 8.40 mmol) in THF (11 mL) was treated with (S)-ethyl 5-oxopyrrolidine-2-carboxylate (0.88 g, 5.60 mmol). The mixture was stirred at rt for 15 min, then 1-(bromomethyl)-4-fluorobenzene (0.837 mL, 6.72 mmol) was added and the mixture was stirred at rt overnight. The mixture was concentrated to give crude methyl (S)-1-(4-fluorobenzyl)-5-oxopyrrolidine-2-carboxylate, used without purification. This was dissolved in THF-MeOH-water (3:1:1, 112 mL) and treated with LiOH monohydrate (0.267 g, 11.2 mmol). The mixture was stirred at rt for 20 h, then was partially concentrated. The aqueous residue was diluted with water and washed twice with EtOAc. The aqueous phase was acidified with 1 M aqueous HCl to about pH 2, and then was extracted with EtOAc. The organic phase was washed with brine, dried and concentrated to provide (S)-1-(4-fluorobenzyl)-5-oxopyrrolidine-2-carboxylic acid as a yellow syrup (0.54 g, 41% yield). LCMS m/z 238.3 (M+H)⁺, HPLC $t_R$ 0.92 min (method A). ¹H NMR (400 MHz, DMSO-$d_6$) δ 12.90 (br. s., 1H), 7.28-7.21 (m, 2H), 7.19-7.11 (m, 2H), 4.79 (d, J=15.0 Hz, 1H), 3.97-3.89 (m, 2H), 2.41-2.20 (m, 3H), 1.98-1.91 (m, 1H).

Intermediate 11

(S)-1-(2-cyanoethyl)-5-oxopyrrolidine-2-carboxylic acid

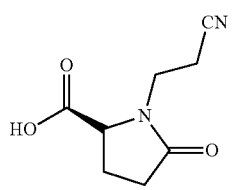

A solution of NaOH (2.72 g, 68.0 mmol) in water (11.3 mL), cooled to rt, was stirred and treated with L-glutamic acid (5.00 g, 34.0 mmol), gradually forming a solution. Acrylonitrile (2.68 mL, 40.8 mmol) was added and the mixture was heated at 50° C. overnight. After 20 h, the mixture was cooled in an ice-water bath and treated slowly with concentrated aqueous HCl (5.17 mL, 64.6 mmol). The solution was concentrated and the residue was suspended in acetone (40 mL) and heated at reflux overnight. After 20 h the mixture was cooled to rt. A white precipitate was removed by filtration and the filtrate was concentrated to afford a colorless oil (8.19 g). This material was purified by preparative SFC using the following conditions: column: Princeton Cyano 3×25 cm, 5 µm; column temperature 40° C.; mobile phase: CO$_2$-MeOH (80:20); flow rate 160 mL/min; pressure 100 bar; injection: 2.5 mL, 109.2 mg/mL in MeOH. (S)-1-(2-cyanoethyl)-5-oxopyrrolidine-2-carboxylic acid was isolated as a white solid (3.72 g, 60% yield). LCMS m/z 183.1 (M+H)$^+$, HPLC $t_R$ 0.39 min (method A). $^1$H NMR (499 MHz, DMSO-d$_6$) δ 13.06 (br. s., 1H), 4.35-4.29 (m, 1H), 3.75 (dt, J=14.0, 7.0 Hz, 1H), 3.21-3.13 (m, 1H), 2.73 (t, J=6.8 Hz, 2H), 2.35-2.22 (m, 3H), 2.02-1.96 (m, 1H).

Intermediate 12

(2S,4R)-4-fluoro-1-(methyl-d$_3$)-5-oxopyrrolidine-2-carboxylic acid

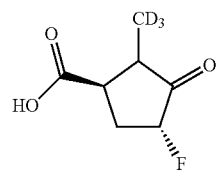 [SMILES: [2H]C([2H])([2H])C1C(=O)[C@H](F)C[C@H]1C(=O)O]

Step A: 1-(tert-butyl) 2-methyl (2S,4R)-4-fluoropyrrolidine-1,2-dicarboxylate

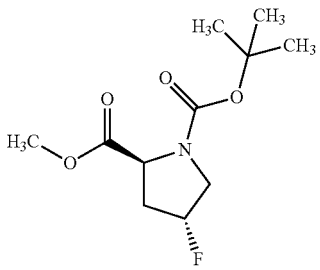 [SMILES: COC(=O)[C@@H]1C[C@@H](F)CN1C(=O)OC(C)(C)C]

A solution of (2S,4S)-1-tert-butyl 2-methyl 4-hydroxypyrrolidine-1,2-dicarboxylate (10.0 g, 40.8 mmol) in DCM (204 mL) was cooled in an ice-water bath and treated slowly with DAST (6.46 mL, 48.9 mmol). The mixture was stirred at rt for 5.5 h, then was partitioned between water and additional DCM. The organic phase was washed with bine, dried and concentrated to afford 1-(tert-butyl) 2-methyl (2S,4R)-4-fluoropyrrolidine-1,2-dicarboxylate as a light yellow syrup (10.6 g, 94% yield, 90% estimated purity). LCMS m/z 270.2 (M+Na)$^+$, HPLC $t_R$ 0.80 min (method A).

Step B: 1-(tert-butyl) 2-methyl (2S,4R)-4-fluoro-5-oxopyrrolidine-1,2-dicarboxylate

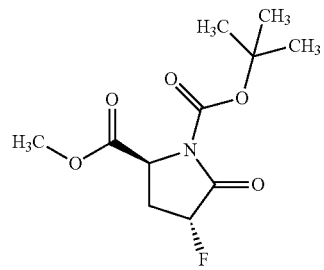 [SMILES: COC(=O)[C@@H]1C[C@@H](F)C(=O)N1C(=O)OC(C)(C)C]

A solution of sodium periodate (44.6 g, 209 mmol) in water (435 mL) was treated with RuCl$_3$ hydrate (7.84 g, 34.8 mmol), forming a dark red solution. This was treated slowly with a solution of crude (2S,4R)-1-tert-butyl 2-methyl 4-fluoropyrrolidine-1,2-dicarboxylate (9.55 g, 34.8 mmol) in EtOAc (145 mL). The mixture was stirred at rt for 17 h, then was treated with IPA (80 mL) and stirred at rt for 3 h. The mixture was filtered through Celite and the solids were washed with water and EtOAc. The combined filtrates were diluted with additional EtOAc and water. The organic phase was separated, washed with brine, dried and concentrated. The residue was purified by column chromatography on silica gel (120 g), eluting with EtOAc-hexanes (10-50%), to provide 1-(tert-butyl) 2-methyl (2S,4R)-4-fluoro-5-oxopyrrolidine-1,2-dicarboxylate as a light yellow oil (67% yield). LCMS m/z 284.0 (M+Na)$^+$, HPLC $t_R$ 0.76 min (method A). $^1$H NMR (400 MHz, CDCl$_3$): δ 5.30-5.11 (m, 1H), 4.68 (dd, J=9.5, 2.0 Hz, 1H), 3.81 (s, 3H), 2.61-2.40 (m, 2H), 1.53 (s, 9H).

Step C: methyl (2S,4R)-4-fluoro-5-oxopyrrolidine-2-carboxylate

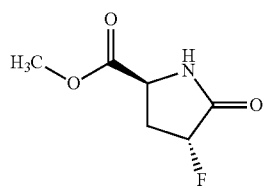

A solution of (2S,4R)-1-tert-butyl 2-methyl 4-fluoro-5-oxopyrrolidine-1,2-dicarboxylate (7.75 g, 25.8 mmol) in DCM (32 mL) was cooled in an ice-water bath and treated with TFA (12 mL). The mixture was stirred at rt for 2 h, then was concentrated and the residue was partitioned between water and EtOAc. The organic phase was washed sequentially with 1.5 M aqueous K$_2$HPO$_4$ and brine, dried and concentrated. The aqueous phase was extracted with chloroform-IPA (3:1) to provide additional product. The two portions were combined to provide methyl (2S,4R)-4-fluoro-5-oxopyrrolidine-2-carboxylate as a dark yellow syrup (3.38 g, 81% yield). LCMS m/z 162.0 (M+H)+, HPLC $t_R$ 0.41 min (method A). $^1$H NMR (400 MHz, CDCl$_3$) δ 6.86 (br. s., 1H), 5.23-5.03 (m, 1H), 4.47-4.34 (m, 1H), 3.82-3.78 (m, 3H), 2.69-2.58 (m, 2H).

Step D: methyl (2S,4R)-4-fluoro-1-(methyl-d₃)-5-oxopyrrolidine-2-carboxylate

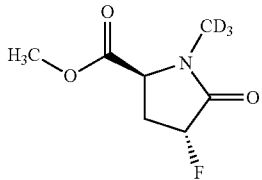

A mixture of (2S,4R)-methyl 4-fluoro-5-oxopyrrolidine-2-carboxylate (0.48 g, 2.98 mmol) and Cs₂CO₃ (2.43 g, 7.45 mmol) in MeCN (16.6 mL) was treated with iodomethane-d₃ (0.927 mL, 14.9 mmol) and heated at 45° C. overnight in a sealed vial. After 18 h, the mixture was cooled to rt, filtered and concentrated to provide methyl (2S,4R)-4-fluoro-1-(methyl-d₃)-5-oxopyrrolidine-2-carboxylate as a light yellow solid (0.53 g, quantitative yield). LCMS m/z 179.1 (M+H)⁺, HPLC $t_R$ 0.46 min (method A).

Step E: (2S,4R)-4-fluoro-1-(methyl-d₃)-5-oxopyrrolidine-2-carboxylic Acid

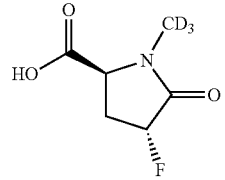 [SMILES: [2H]C([2H])([2H])N1C(=O)[C@H](F)C[C@H]1C(=O)O]

A mixture of methyl (2S,4R)-4-fluoro-1-(methyl-d₃)-5-oxopyrrolidine-2-carboxylate (0.53 g, 2.97 mmol) and LiOH monohydrate (0.221 g, 9.22 mmol) in THF-MeOH-water (3:1:1) (29.7 mL) was stirred at rt for 18 h. The mixture was concentrated, the residue was treated with HCl (4 M in 1,4-dioxane; 2.38 mL, 9.52 mmol), and the mixture was concentrated again to dryness. The crude mixture containing (2S,4R)-4-fluoro-1-(methyl-d₃)-5-oxopyrrolidine-2-carboxylic acid and LiCl was used without further purification. LCMS m/z 165.0 (M+H)⁺, HPLC $t_R$ 0.35 min (method A).

Intermediate 13

(2S,4R)-4-fluoro-5-oxopyrrolidine-2-carboxylic acid

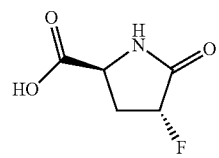

A solution of methyl (2S,4R)-4-fluoro-5-oxopyrrolidine-2-carboxylate (Intermediate 12, Step C; 1.01 g, 6.27 mmol) in THF (30 mL) and MeOH (10 mL) was treated with a solution of LiOH monohydrate (0.407 g, 9.70 mmol) in water (10 mL). The mixture was stirred at rt for 2 h, then was acidified with 1 M aqueous HCl (9.8 mL) and concentrated under vacuum to remove the organic solvents. The aqueous residue was frozen at −78° C. and lyophilized to provide (2S,4R)-4-fluoro-5-oxopyrrolidine-2-carboxylic acid as a sticky yellow-tan amorphous solid (1.545 g) containing LiCl and residual water (estimated purity 60%) which was used without further purification. LCMS m/z 189.4 (M+H+MeCN)⁺, HPLC $t_R$ 0.29 min (method A).

Intermediate 14

(1S,2S,5R)-3-(tert-butoxycarbonyl)-4-oxo-3-azabicyclo[3.1.0]hexane-2-carboxylic acid

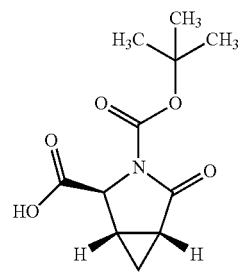 [SMILES: CC(C)(C)OC(=O)N1C(=O)[C@@H]2C[C@@H]2[C@H]1C(=O)O]

(1S,2S,5R)-3-(tert-butoxycarbonyl)-4-oxo-3-azabicyclo[3.1.0]hexane-2-carboxylic acid was prepared using the procedures of PCT Int. Appl. 2008/150364, Example 4, and PCT Int. Appl. 2014/141132, Example 5.

Intermediate 15

(2S,4R)-1-(2-((tert-butyldimethylsilyl)oxy)ethyl)-4-fluoro-5-oxopyrrolidine-2-carboxylic acid, lithium salt

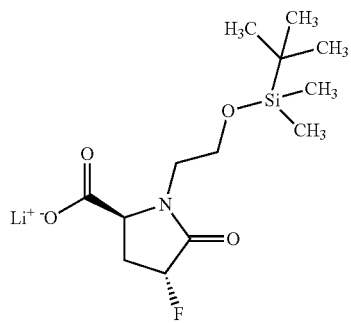

Step A: methyl (2S,4R)-1-(2-((tert-butyldimethylsilyl)oxy)ethyl)-4-fluoro-5-oxopyrrolidine-2-carboxylate

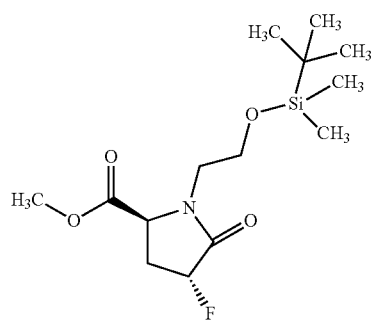 [SMILES: COC(=O)[C@@H]1C[C@@H](F)C(=O)N1CCO[Si](C)(C)C(C)(C)C]

A mixture of (2S,4R)-methyl 4-fluoro-5-oxopyrrolidine-2-carboxylate (Intermediate 12, Step C; 0.37 g, 2.30 mmol) and Cs$_2$CO$_3$ (1.35 g, 4.13 mmol) in MeCN (15.3 mL) was treated with (2-bromoethoxy)(tert-butyl)dimethylsilane (2.20 g, 9.19 mmol) and the resulting mixture was heated at 50° C. overnight in a sealed vial. After 17 h, the mixture was cooled to rt and partitioned between EtOAc and water. The organic phase was washed with brine, dried and concentrated. The residue was subjected to column chromatography on silica gel (40 g), eluting with EtOAc-hexanes (10-20%), to provide (2S,4R)-methyl 1-(2-((tert-butyldimethylsilyl)oxy)ethyl)-4-fluoro-5-oxopyrrolidine-2-carboxylate as a light brown oil (0.398 g, 54% yield). LCMS m/z 320.1 (M+H)$^+$, HPLC $t_R$ 1.03 min (method A).

Step B: (2S,4R)-1-(2-((tert-butyldimethylsilyl)oxy)ethyl)-4-fluoro-5-oxopyrrolidine-2-carboxylic acid, Lithium Salt

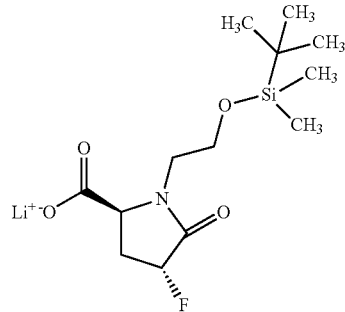

A mixture of (2S,4R)-methyl 1-(2-((tert-butyldimethylsilyl)oxy)ethyl)-4-fluoro-5-oxopyrrolidine-2-carboxylate (0.398 g, 1.25 mmol) and LiOH monohydrate (0.06 g, 2.49 mmol) in THF-MeOH-water (3:1:1, 7.33 mL) was stirred at rt overnight. After 17 h, the mixture was concentrated to afford (2S,4R)-1-(2-((tert-butyldimethylsilyl)oxy)ethyl)-4-fluoro-5-oxopyrrolidine-2-carboxylic acid, lithium salt, mixed with residual LiOH, as a white solid (0.36 g) which was used without further purification. LCMS m/z 306.1 (M+H)$^+$, HPLC $t_R$ 0.89 min (method A).

Intermediate 16

(2S,4R)-1-(3-((tert-butyldimethylsilyl)oxy)-2,2-dimethylpropyl)-4-fluoro-5-oxopyrrolidine-2-carboxylic acid, lithium salt

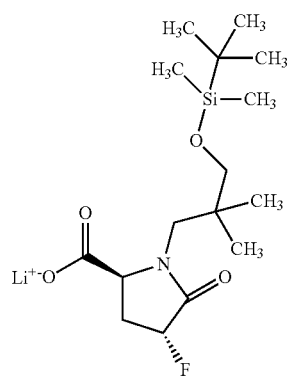

Step A: mixture of methyl and ethyl esters of (2S,4R)-2-amino-4-fluoropentanedioic acid hydrochloride

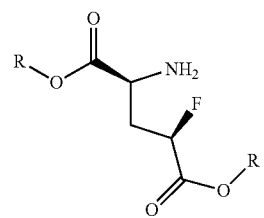

R = CH$_3$, CH$_2$CH$_3$

A mixture of methyl (2S,4R)-4-fluoro-5-oxopyrrolidine-2-carboxylate (Intermediate 12, Step C; 1.00 g, 6.21 mmol) and concentrated HCl (10.3 mL, 62.1 mmol) was heated at reflux. After 6 h the mixture was cooled to rt, treated with MeOH (3 mL) and heated again at reflux. After 6 h more the mixture was concentrated. The residue was dissolved in ethanol and again concentrated to provide a mixture of methyl and ethyl esters of (2S,4R)-2-amino-4-fluoropentanedioic acid hydrochloride as an off-white solid (1.42 g, quantitative yield), which was used without further purification. LCMS m/z 194.4 (M+H)$^+$ for bis-methyl ester, 208.4 (M+H)$^+$ for methyl-ethyl ester, and 222.4 (M+H)$^+$ for bis-ethyl ester, HPLC $t_R$ 0.50-0.55 min (method A).

Step B: methyl (2S,4R)-1-(3-((tert-butyldimethylsilyl)oxy)-2,2-dimethylpropyl)-4-fluoro-5-oxopyrrolidine-2-carboxylate

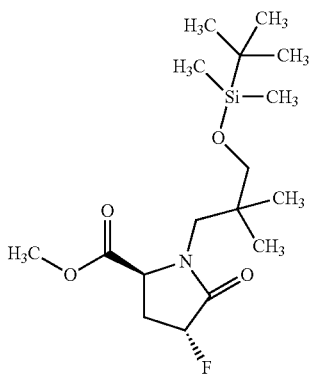 [SMILES: COC(=O)[C@@H]1C[C@@H](F)C(=O)N1CC(C)(C)CO[Si](C)(C)C(C)(C)C]

A solution of a mixture of methyl and ethyl esters of (2S,4R)-2-amino-4-fluoropentanedioic acid hydrochloride (1.39 g, 6.05 mmol) and DIEA (2.11 mL, 12.1 mmol) in DCE (50 mL) was treated with $Na_2SO_4$ (8.60 g, 60.5 mmol). The mixture was stirred at rt for 5 min, then treated with 3-((tert-butyldimethylsilyl)oxy)-2,2-dimethylpropanal (1.44 g, 6.66 mmol) and acetic acid (0.866 mL, 15.13 mmol). After 3 h, sodium triacetoxyborohydride (3.85 g, 18.2 mmol) was added. After stirring at rt overnight, the mixture was diluted with EtOAc (30 mL), and washed sequentially with saturated aqueous $NaHCO_3$ (20 mL) and brine (20 mL), dried and concentrated. The residue was subjected to column chromatography on silica gel, eluting with ethyl acetate-hexanes (gradient from 0-100%), to provide methyl (2S, 4R)-1-(3-((tert-butyldimethylsilyl)oxy)-2,2-dimethylpropyl)-4-fluoro-5-oxopyrrolidine-2-carboxylate as a colorless oil (840 mg, 38% yield). LCMS m/z 362.6 (M+H)$^+$, HPLC $t_R$ 1.18 min (method A). $^1$H NMR (400 MHz, CDCl$_3$) δ 5.39-5.04 (m, 1H), 4.49 (dd, J=9.0, 1.3 Hz, 1H), 3.78 (s, 3H), 3.56 (d, J=14.1 Hz, 1H), 3.37-3.19 (m, 2H), 2.81 (d, J=13.9 Hz, 1H), 2.65-2.54 (m, 1H), 2.53-2.34 (m, 1H), 0.95-0.88 (m, 15H), 0.07 (d, J=1.5 Hz, 6H).

Step C: (2S,4R)-1-(3-((tert-butyldimethylsilyl)oxy)-2,2-dimethylpropyl)-4-fluoro-5-oxopyrrolidine-2-carboxylic acid, Lithium Salt

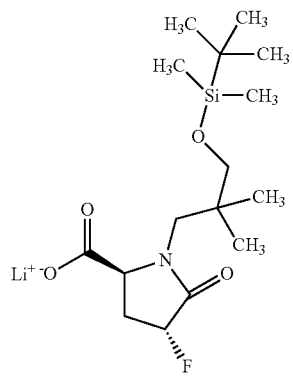

A mixture of methyl (2S,4R)-1-(3-((tert-butyldimethylsilyl)oxy)-2,2-dimethylpropyl)-4-fluoro-5-oxopyrrolidine-2-carboxylate (810 mg, 2.24 mmol), THF (0.5 mL), water (0.1 mL) and LiOH hydrate (104 mg, 2.47 mmol) was stirred at rt for 5 h. The mixture was concentrated to give crude (2S,4R)-1-(3-((tert-butyldimethylsilyl)oxy)-2,2-dimethylpropyl)-4-fluoro-5-oxopyrrolidine-2-carboxylic acid lithium salt as a white solid (770 mg, 99% yield), used without purification. LCMS m/z 348.5 (M+H)$^+$, HPLC $t_R$ 1.07 min (method A).

Intermediate 17

(1r,4r)-4-carbamoylcyclohexanecarboxylic acid, Lithium Salt

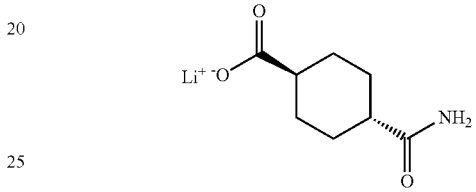

A mixture of trans-1,4-cyclohexanedicarboxylic acid monomethyl ester (0.15 g, 0.806 mmol), aqueous $NH_4OH$ (0.125 mL, 3.22 mmol), and HATU (0.613 g, 1.61 mmol) in THF (10 mL) was stirred at rt. After 18 h the mixture was partitioned between 1 M aqueous HCl and EtOAc. The organic phase was washed sequentially with saturated $NaHCO_3$ and bine, dried and concentrated. The residue was subjected to column chromatography on silica gel (12 g), eluting with EtOAc-hexanes (50-70%), to provide (1r,4r)-methyl 4-carbamoylcyclohexanecarboxylate as a white solid (78 mg). LCMS m/z 186.1 (M+H)$^+$, HPLC $t_R$ 0.52 min (method A). This was dissolved in THF-MeOH-water (3:1:1, 2 mL) and treated with LiOH monohydrate (0.031 g, 1.29 mmol). The mixture was stirred at rt overnight. After 16 h, it was concentrated to afford (1r,4r)-4-carbamoylcyclohexanecarboxylic acid, lithium salt, mixed with residual LiOH, as a white solid (113 mg) which was used without further purification. LCMS m/z 172.0 (M+H)$^+$, HPLC $t_R$ 0.38 min (method A).

Intermediate 18

4-carbamoylbicyclo[2.2.2]octane-1-carboxyic acid, Lithium Salt

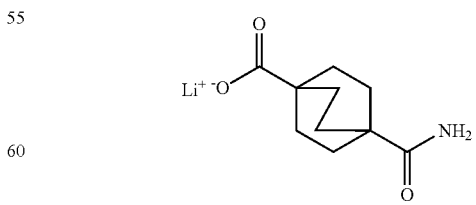

Following the procedure used to prepare Intermediate 17, 4-(methoxycarbonyl)-bicyclo[2.2.2]octane-1-carboxylic acid was converted into 4-carbamoylbicyclo[2.2.2]-octane-1-carboxylic acid, lithium salt, mixed with residual LiOH, which was used without further purification. LCMS m/z 198.1 (M+H)+, HPLC t$_R$ 0.43 min (method A).

Intermediate 19

(1R,2S,4R)-4-(methoxycarbonyl)-2-methylcyclohexane-1-carboxylic acid

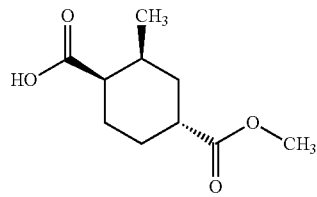

Step A: tert-butyl 2-acetyl-5-oxohexanoate

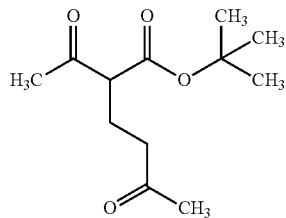

A mixture of methyl vinyl ketone (116 mL, 1.43 mol), tert-butyl acetoacetate (248 mL, 1.50 mol), and TEA (0.994 mL, 7.13 mmol) was cooled to 12° C. in an acetone-dry ice bath. LiClO$_4$ (15.18 g, 143 mmol) was added portionwise over 30 min, then the mixture was warmed to 25° C. and stirred for 22 h. Diethyl ether (5 L) and added and the resulting mixture was washed sequentially with water (75 mL) and brine (75 mL), dried and concentrated. The residue, a cloudy oil (331.83 g), was redissolved in ether, filtered, and the filtrate was concentrated to give tert-butyl 2-acetyl-5-oxohexanoate as a colorless oil (330.54 g, quantitative yield). $^1$H NMR (400 MHz, CDCl$_3$) δ 3.40-3.40 (m, 1H), 2.54-2.45 (m, 2H), 2.25-2.21 (m, 3H), 2.15 (s, 3H), 2.12-2.01 (m, 2H), 1.48-1.45 (m, 9H).

Step B: tert-butyl (R)-2-methyl-4-oxocyclohex-2-ene-1-carboxylate

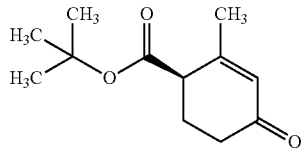

A mixture of tert-butyl 2-acetyl-5-oxohexanoate (57.5 g, 252 mmol), THF (331 mL), acetic acid (13.70 mL, 239 mmol) and piperidine (19.95 mL, 202 mmol) was heated to 60° C. and stirred for 44 h. EtOAc (670 mL) was added, followed by 1 N aqueous HCl (200 mL). The mixture was stirred for 10 minutes, then the layers were separated. The organic phase was washed sequentially with saturated aqueous NaHCO$_3$ (2×200 mL) and brine (200 mL), dried and concentrated. The residue, an orange oil (46.0 g), was subjected to column chromatography, and the resulting racemic product was separated by preparative SFC to give tert-butyl (R)-2-methyl-4-oxocyclohex-2-ene-1-carboxylate (18.02 g, 34% yield). $^1$H NMR (499 MHz, CDCl$_3$) δ 6.09-5.75 (m, 1H), 3.36-3.05 (m, 1H), 2.68-2.47 (m, 1H), 2.41-2.27 (m, 2H), 2.26-2.13 (m, 1H), 2.09-2.00 (m, 3H), 1.50 (s, 9H).

Step C: tert-butyl (1R, 2S)-2-methyl-4-oxocyclohexane-1-carboxylate

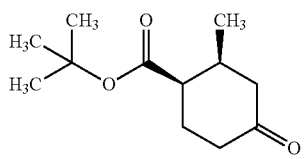

A solution of tert-butyl (R)-2-methyl-4-oxocyclohex-2-enecarboxylate (20.5 g, 97 mmol) in THF (195 mL) was bubbled with N$_2$ for several minutes. Wet 10% Pd on carbon (2 g, 1.879 mmol) was added and the mixture was stirred under a hydrogen atmosphere (balloon pressure) for 14 h. The mixture was filtered through Celite and the solids were rinsed with THF (500 mL). The combined filtrates were concentrated to give tert-butyl (1R, 2S)-2-methyl-4-oxocyclohexanecarboxylate (22.9 g, quantitative yield). $^1$H NMR (400 MHz, CDCl$_3$) δ 2.85-2.69 (m, 1H), 2.61-2.38 (m, 4H), 2.36-1.93 (m, 3H), 1.54-1.42 (m, 9H), 1.04-0.92 (m, 3H).

Step D: tert-butyl (1R, 6S)-6-methyl-4-(((trifluoromethyl)sulfonyl)oxy)cyclohex-3-ene-1-carboxylate

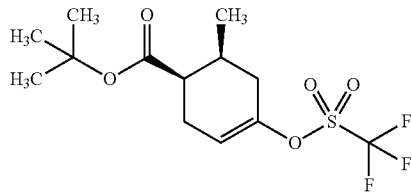 [SMILES: C[C@H]1CC(OS(=O)(=O)C(F)(F)F)=CC[C@H]1C(=O)OC(C)(C)C]

A mixture of N,N-bis(trifluoromethylsulfolfonyl)aniline (50.1 g, 140 mmol) and tert-butyl (1R,2S)-2-methyl-4-oxocyclohexanecarboxylate (22.9 g, 108 mmol) in anhydrous THF (330 mL) was cooled to −70° C. on an acetone-dry ice bath. Potassium bis(trimethylsilyl)amide (1.0 M in THF, 140 mL, 140 mmol) was added dropwise with stirring over 1 h. After 1 h more, the reaction mixture was treated with water (500 mL) and warmed to 0° C. The mixture was extracted with EtOAc (500 mL), and the organic phase was washed sequentially with water (500 mL) and brine (500 mL), and dried and concentrated. The residue (41 g) was subjected to column chromatography to give tert-butyl (1R, 2S)-2-methyl-4-(((trifluoromethyl)sulfonyl)oxy)cyclohex-3-enecarboxylate (30.24 g, 81% yield). $^1$H NMR (499 MHz, CDCl$_3$) δ 5.76 (td, J=5.4, 1.9 Hz, 1H), 2.99-2.09 (m, 5H), 2.02-1.86 (m, 1H), 1.48 (d, J=3.5 Hz, 9H), 1.05-0.99 (m, 3H).

Step E: 4-(tert-butyl) 1-methyl (4R, 5S)-5-methyl-cyclohex-1-ene-1,4-dicarboxylate

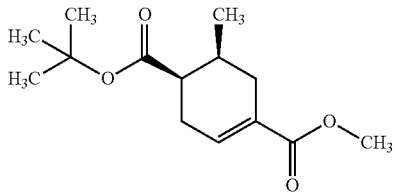 [SMILES: COC(=O)C1=CC[C@@H](C(=O)OC(C)(C)C)[C@@H](C)C1]

A solution of tert-butyl (1R, 6S)-6-methyl-4-(((trifluoromethyl)sulfonyl)oxy)cyclohex-3-enecarboxylate (29.58 g, 86 mmol) in anhydrous DMF (215 mL) and MeOH (215 mL) was bubbled with $N_2$ for 5 min. Palladium acetate (1.929 g, 8.59 mmol), 1,1'-bis(diphenylphosphino)ferrocene (4.76 g, 8.59 mmol) and TEA (35.9 mL, 258 mmol) were added. The mixture was then bubbled with carbon monoxide for 10 min, stirred under a carbon monoxide atmosphere (balloon pressure) for 18 h. The mixture was diluted with EtOAc (500 mL), washed sequentially with 10% aqueous LiCl (3×500 mL) and brine (500 mL), dried and concentrated. The residue (22.4 g) was subjected to column chromatography to give 4-tert-butyl 1-methyl (4R,5S)-5-methylcyclohex-1-ene-1,4-dicarboxylate (14.11 g, 65% yield). $^1$H NMR (499 MHz, $CDCl_3$) δ 6.97-6.89 (m, 1H), 3.74 (s, 3H), 2.88-1.75 (m, 6H), 1.47 (d, J=3.8 Hz, 9H), 1.01 (d, J=7.2 Hz, 2H), 0.92 (d, J=6.8 Hz, 1H).

Step F: 1-(tert-butyl) 4-methyl (1R, 2S, 4R)-2-methylcyclohexane-1,4-dicarboxylate

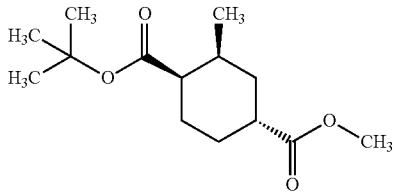 [SMILES: COC(=O)[C@@H]1CC[C@@H](C(=O)OC(C)(C)C)[C@@H](C)C1]

A solution of 4-tert-butyl 1-methyl (4R, 5S)-5-methylcyclohex-1-ene-1,4-dicarboxylate (14.09 g, 55.4 mmol) in DCM (554 mL) was bubbled with $N_2$ for 10 min. (1,5-cyclooctadiene)-pyridine(tricyclohexylphosphine)iridium(i) hexafluorophosphate (Crabtree's catalyst; 1.115 g, 1.385 mmol) was added and the mixture was evacuated and purged 3 times with hydrogen. The mixture was then stirred under a hydrogen atmosphere (balloon pressure) for 17 h. The solution was concentrated and the residue (14.7 g) was subjected to column chromatography to give 1-tert-butyl 4-methyl (1R,2S,4R)-2-methylcyclohexane-1,4-dicarboxylate as a colorless oil (14.11 g, 99% yield). $^1$H NMR (400 MHz, $CDCl_3$) δ 3.66 (s, 3H), 2.54-2.34 (m, 3H), 2.00 (ddd, J=13.2, 3.7, 1.7 Hz, 1H), 1.89-1.80 (m, 1H), 1.78-1.56 (m, 3H), 1.46-1.38 (m, 10H), 0.92 (d, J=7.1 Hz, 3H).

Step G: (1R, 2S, 4R)-4-(methoxycarbonyl)-2-methylcyclohexane-1-carboxylic acid

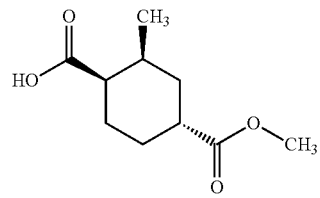

A solution of 1-tert-butyl 4-methyl (1R,2S,4R)-2-methylcyclohexane-1,4-dicarboxylate (27.5 g, 107 mmol) in DCM (37.2 mL) was treated with TFA (37.2 mL, 483 mmol) and stirred at rt. After 9 h, the mixture was concentrated, and the residue was treated with heptane (100 mL) and concentrated again. The residue was treated with heptane (20 mL) twice more and concentrated under high vacuum. The residue was crystallized from 5% tert-butyl methyl ether-heptane to give (1R,2S,4R)-4-(methoxycarbonyl)-2-methylcyclohexanecarboxylic acid as a white solid (17.25 g, 80% yield). $^1$H NMR (499 MHz, $CDCl_3$) δ 3.68 (s, 3H), 2.57-2.46 (m, 3H), 2.04 (dqd, J=13.3, 3.8, 1.8 Hz, 1H), 1.93-1.87 (m, 1H), 1.83 (dq, J=14.0, 3.9 Hz, 1H), 1.78-1.63 (m, 2H), 1.52-1.39 (m, 1H), 0.98 (d, J=7.0 Hz, 3H). $^{13}$C NMR (126 MHz, $CDCl_3$) δ 179.7, 176.3, 51.7, 45.1, 37.0, 34.8, 29.5, 27.6, 21.1, 13.9.

Intermediate 20

2-(3-hydroxy-1,1-dioxidotetrahydrothiophen-3-yl)acetic acid (racemic)

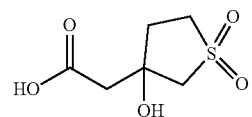

Step A: tert-butyl 2-(3-hydroxytetrahydrothiophen-3-yl)acetate (racemic)

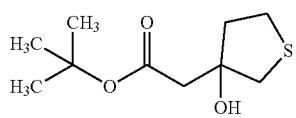

A solution of tert-butyl acetate (3.14 mL, 23.4 mmol) in THF (50 mL) at −78° C. was treated slowly with lithium bis(trimethylsilyl)amide, 1.0 M in THF (22.2 mL, 22.2 mmol). The mixture was stirred for 45 min, then was treated slowly with a solution of tetrahydrothiophen-3-one (2.00 mL, 23.4 mmol) in THF (5 mL). The mixture was stirred at −78° C. for 20 min, then was treated slowly with 2 M aqueous HCl (12.3 mL, 24.6 mmol). The cooling bath was removed and the mixture was warmed to rt, then was extracted twice with EtOAc. The combined organic phases were washed sequentially with 1.5 M aqueous $K_2HPO_4$ and brine, dried and concentrated to provide crude racemic tert-butyl 2-(3-hydroxytetrahydrothiophen-3-yl)acetate as a colorless oil, used without purification. LCMS m/z 163.0 (M+H-tBu)+, HPLC t$_R$ 0.81 min (method A).

Step B: tert-butyl 2-(3-hydroxy-1,1-dioxidotetrahydrothiophen-3-yl)acetate

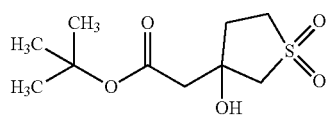 [SMILES: CC(C)(C)OC(=O)CC1(O)CCS(=O)(=O)C1]

A solution of crude racemic tert-butyl 2-(3-hydroxytetrahydrothiophen-3-yl)acetate (4.80 g, 22.0 mmol) in DCM (75 mL) at 0° C. was treated portionwise with mCPBA (70%, 17.3 g, 77.0 mmol). After 50 min, additional mCPBA (3.79 g) was added. After a total of 2 h, the mixture was filtered through Celite and the solids were washed with DCM. The combined filtrates were washed sequentially with saturated aqueous NaHCO$_3$ and brine, dried and concentrated to provide racemic tert-butyl 2-(3-hydroxy-1,1-dioxidotetrahydrothiophen-3-yl)acetate as a white solid (5.55 g, quantitative yield). $^1$H NMR (499 MHz, DMSO-d$_6$) δ 5.48 (s, 1H), 3.26-3.12 (m, 4H), 2.67-2.54 (m, 2H), 2.31-2.12 (m, 2H), 1.41 (s, 9H).

Step C: 2-(3-hydroxy-1,1-dioxidotetrahydrothiophen-3-yl)acetic acid (racemic)

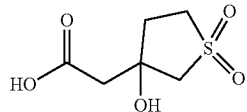

A solution of racemic tert-butyl 2-(3-hydroxy-1,1-dioxidotetrahydrothiophen-3-yl)acetate (5.55 g, 22.2 mmol) in DCM (60 mL) at rt was treated with TFA (12 mL, 156 mmol). After 2 h the solution was concentrated and dried in vacuo to provide racemic 2-(3-hydroxy-1,1-dioxidotetrahydrothiophen-3-yl)acetic acid as a white solid (4.21 g, 98% yield), used without further purification. $^1$H NMR (499 MHz, DMSO-d$_6$) δ 3.30-3.13 (m, 4H), 2.70-2.57 (m, 2H), 2.31-2.15 (m, 2H).

Example 1

3-((2S)-2-(9a-((4-fluorophenyl)sulfonyl)-3-(perfluoropropan-2-yl)-6,6a7,8,9,9a-hexahydro-5H-pyrrolo[2,3-h]quinoline-7-carbonyl)-5-oxopyrrolidin-1-yl) propanenitrile (Single Enantiomer)

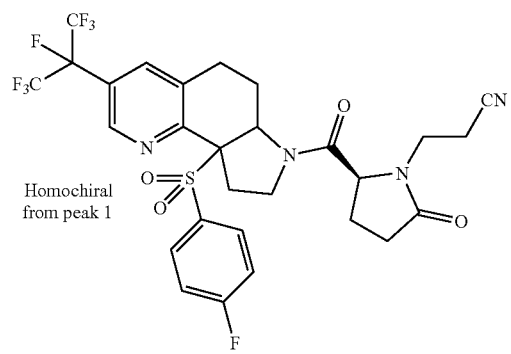 [SMILES: N#CCCN1C(=O)CC[C@H]1C(=O)N1CCC2(S(=O)(=O)c3ccc(F)cc3)c3ncc(C(F)(C(F)(F)F)C(F)(F)F)cc3CCC12]

Homochiral from peak 1

A mixture of a single enantiomer of 9a-((4-fluorophenyl)sulfonyl)-3-(perfluoropropan-2-yl)-6,6a,7,8,9,9a-hexahydro-5H-pyrrolo[2,3-h]quinoline dihydrochloride (Intermediate 1; 30 mg, 0.060 mmol), (S)-1-(2-cyanoethyl)-5-oxopyrrolidine-2-carboxylic acid (Intermediate 11; 24.8 mg, 0.120 mmol), EDC (23.0 mg, 0.120 mmol), HOBT (16.5 mg, 0.108 mmol), and DIEA (42 μL, 0.240 mmol) in DMF (1.0 mL) was stirred at rt. After 17 h, the mixture was filtered and purified by preparative HPLC (method D, gradient 30-100% B, 20 min) to provide a single enantiomer of 3-((2S)-2-(9a-((4-fluorophenyl)sulfonyl)-3-(perfluoro-propan-2-yl)-6,6a,7,8,9,9a-hexahydro-5H-pyrrolo[2,3-h]quinoline-7-carbonyl)-5-oxopyrrolidin-1-yl)propanenitrile (22 mg, 55% yield). LCMS m/z 665.2 (M+H)+, HPLC t$_R$ 1.95 min (method C). $^1$H NMR (500 MHz, DMSO-d$_6$) δ 8.65 (br. s., 1H), 7.95 (br. s., 1H), 7.51 (d, J=4.9 Hz, 2H), 7.38-7.23 (m, 2H), 5.10-4.63 (m, 2H), 4.05-3.31 (m, 4H), 3.19-2.95 (m, 2H), 2.90-2.67 (m, 4H), 2.46 (br. s., 1H), 2.35-2.16 (m, 3H), 1.94-1.42 (m, 2H).

The Examples in Table 2 were prepared by following procedures used to prepare Example 1 or similar procedures, from appropriate acid and amine intermediates.

TABLE 2

| Ex. # | Structure | LCMS m/z observed | HPLC t$_R$ (min) | HPLC method |
|---|---|---|---|---|
| 2 | <br>•TFA<br>Homochiral from peak 1 | 647.1 (M + H)+ | 2.04 | C |

TABLE 2-continued

| Ex. # | Structure | LCMS m/z observed | HPLC $t_R$ (min) | HPLC method |
|---|---|---|---|---|
| 3 | Homochiral from peak 1 | 720.4 (M + H)+ | 2.17 | C |
| 4 | Homochiral from peak 1 | 655.3 (M + H)+ | 2.01 | C |
| 5 | Homochiral from peak 1 | 654.3 (M + H)+ | 1.79 | C |
| 6 | ·HCl  Homochiral from peak 1 | 681.0 (M + H)+ | 2.11 | C |

TABLE 2-continued

| Ex. # | Structure | LCMS m/z observed | HPLC t$_R$ (min) | HPLC method |
|---|---|---|---|---|
| 7 | Homochiral from peak 1 | 680.3 (M + H)$^+$ | 1.97 | C |
| 8 | Homochiral from peak 1 | 660.8 (M + H)$^+$ | 1.92 | C |
| 9 | From peak 1 | 667.2 (M + H)$^+$ | 2.02 | C |
| 10 | From peak 2 | 677.2 (M + H)$^+$ | 1.95 | C |

TABLE 2-continued

| Ex. # | Structure | LCMS m/z observed | HPLC t_R (min) | HPLC method |
|---|---|---|---|---|
| 11 | From peak 2 | 659.1 (M + H)+ | 2.04 | C |
| 12 | From peak 2 | 643.3 (M + H)+ | 2.00 | C |
| 13 | From peak 2 | 661.3 (M + H)+ | 2.01 | C |
| 14 | From peak 1 | 665.3 (M + H)+ | 1.98 | C |

TABLE 2-continued
| Ex. # | Structure | LCMS m/z observed | HPLC $t_R$ (min) | HPLC method |
|---|---|---|---|---|
| 15 | 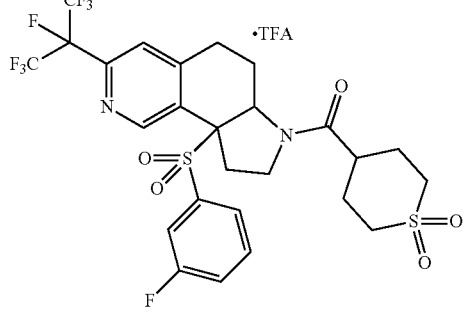<br>From peak 1 | 661.3 (M + H)$^+$ | 2.00 | C |
| 16 | 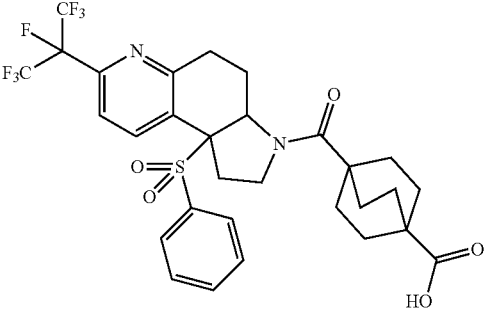<br>From peak 2 | 663.1 (M + H)$^+$ | 2.24 | C |
| 17 | 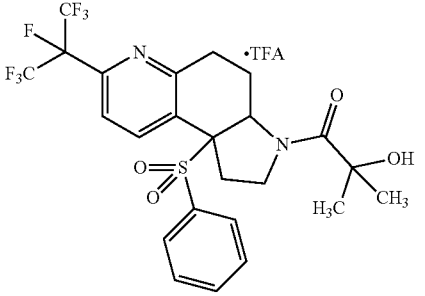<br>From peak 2 | 569.1 (M + H)$^+$ | 2.15 | C |
| 18 | 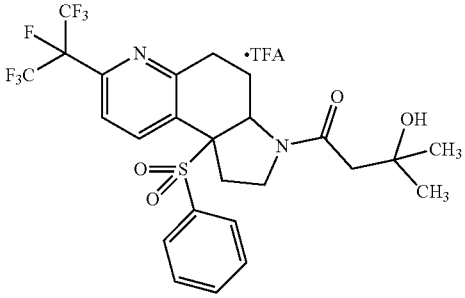<br>From peak 2 | 583.1 (M + H)$^+$ | 2.19 | C |

TABLE 2-continued

| Ex. # | Structure | LCMS m/z observed | HPLC $t_R$ (min) | HPLC method |
|---|---|---|---|---|
| 19 | From peak 2 | 647.3 (M + H)⁺ | 1.98 | C |
| 20 | From peak 2 | 661.3 (M + H)⁺ | 2.05 | C |
| 21 | From peak 2 | 665.3 (M + H)⁺ | 2.02 | C |
| 22 | From peak 2 | 661.0 (M + H)⁺ | 2.05 | C |

Example 23

(1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxylic acid trifluoroacetate (Single Enantiomer)

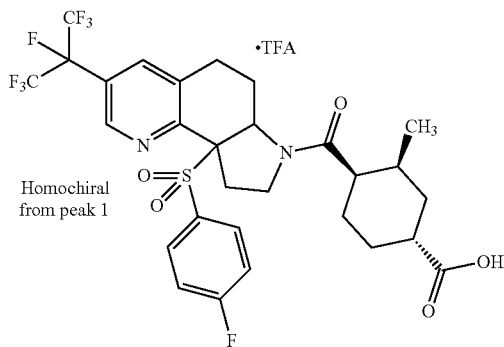 [SMILES: C[C@H]1C[C@H](C(=O)O)CC[C@H]1C(=O)N1CCC2(S(=O)(=O)c3ccc(F)cc3)c3ncc(C(F)(C(F)(F)F)C(F)(F)F)cc3CCC12]

Homochiral from peak 1

A mixture of 9a-((4-fluorophenyl)sulfonyl)-3-(perfluoropropan-2-yl)-6,6a,7,8,9,9a-hexahydro-5H-pyrrolo[2,3-h]quinoline dihydrochloride (Intermediate 1; 40 mg, 0.070 mmol), (1R,2S,4R)-4-(methoxycarbonyl)-2-methylcyclohexanecarboxylic acid (Intermediate 18; 21.0 mg, 0.105 mmol), HATU (47.8 mg, 0.126 mmol) and DIEA (61 μL, 0.349 mmol) in DMF (1.40 mL) was stirred at rt. After 3 days the mixture was purified by preparative HPLC (method E) to provide a single enantiomer of methyl (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxylate as a yellow solid (42 mg). LCMS m/z 683.2 (M+H)$^+$, HPLC $t_R$ 1.09 min (method A). This material was dissolved in THF (6 mL), MeOH (1 mL) and water (1 mL) and treated with LiOH monohydrate (35 mg, 0.84 mmol). The mixture was stirred at rt overnight, then was concentrated to provide a white solid (110 mg). A portion of this (30 mg) was purified by preparative HPLC (method F, gradient 40-80% B, 20 min) to provide a single enantiomer of (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxylic acid trifluoroacetate (4.4 mg, 9.4% yield). LCMS m/z 669.4 (M+H)$^+$, HPLC $t_R$ 2.00 min (method C). $^1$H NMR (500 MHz, DMSO-$d_6$) δ 8.61 (s, 1H), 7.91 (s, 1H), 7.49-7.41 (m, 2H), 7.29 (t, J=8.5 Hz, 2H), 4.95 (dd, J=11.6, 5.2 Hz, 1H), 3.92-3.01 (m, 4H), 2.84-2.73 (m, 2H), 2.61 (d, J=11.3 Hz, 1H), 2.40 (t, J=13.3 Hz, 2H), 2.28 (br. s., 1H), 1.91-1.59 (m, 4H), 1.47-1.27 (m, 3H), 0.90 (d, J=7.0 Hz, 3H).

The Examples in Table 3 were prepared by following procedures used to prepare Example 23 or similar procedures, from appropriate acid and amine intermediates.

TABLE 3

| Ex. # | Structure | LCMS m/z observed | HPLC $t_R$ (min) | HPLC method |
|---|---|---|---|---|
| 24 | (structure shown) Homochiral from peak 2 | 655.1 (M + H)$^+$ | 2.24 | C |
| 25 | (structure shown) Homochiral from peak 2 | 669.1 (M + H)$^+$ | 2.30 | C |

TABLE 3-continued

| Ex. # | Structure | LCMS m/z observed | HPLC $t_R$ (min) | HPLC method |
|---|---|---|---|---|
| 26 | Homochiral from peak 1 | 655.1 (M + H)⁺ | 2.02 | C |
| 27 | Homochiral from peak 1 | 669.1 (M + H)⁺ | 2.10 | C |
| 28 | Homochiral from peak 2 | 637.1 (M + H)⁺ | 2.14 | C |
| 29 | Homochiral from peak 2 | 651.3 (M + H)⁺ | 2.21 | C |

TABLE 3-continued
| Ex. # | Structure | LCMS m/z observed | HPLC $t_R$ (min) | HPLC method |
|---|---|---|---|---|
| 30 | 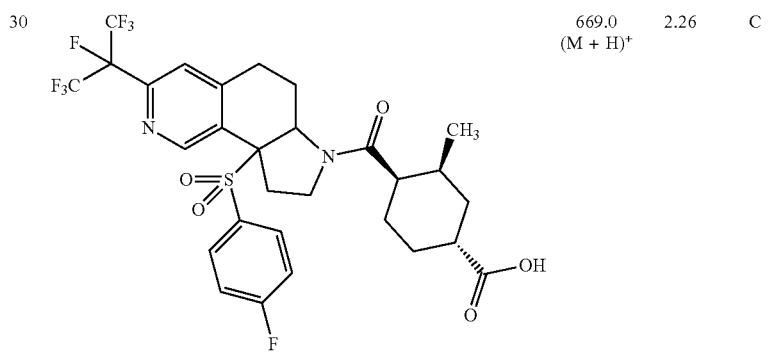  Homochiral from peak 2 | 669.0 (M + H)+ | 2.26 | C |
| 31 | 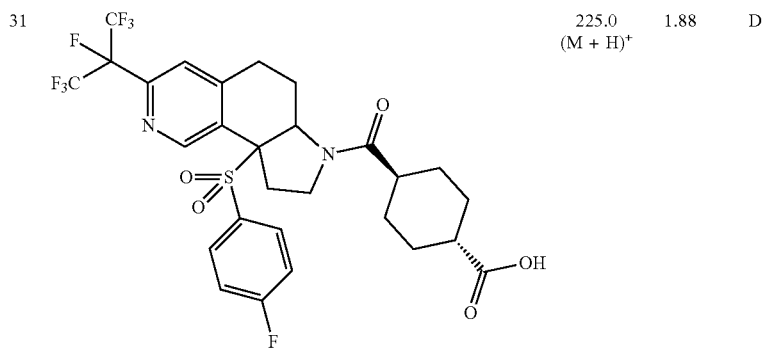  Homochiral from peak 2 | 225.0 (M + H)+ | 1.88 | D |
| 32 | 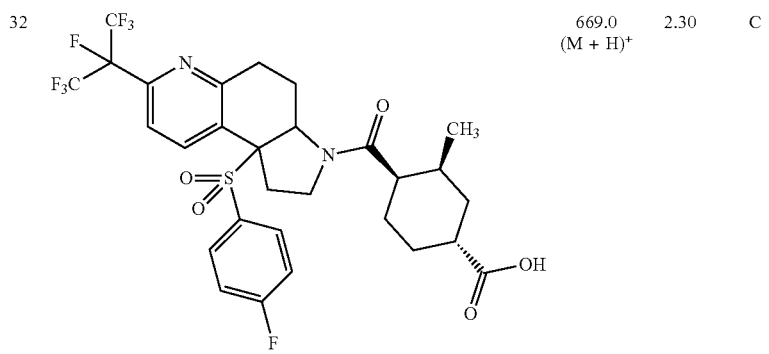  Homochiral from peak 2 | 669.0 (M + H)+ | 2.30 | C |

TABLE 3-continued

| Ex. # | Structure | LCMS m/z observed | HPLC $t_R$ (min) | HPLC method |
|---|---|---|---|---|
| 33 | Homochiral from peak 2 | 655.0 (M + H)+ | 2.24 | C |

Example 34
(1R,4S,5S)-4-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-3-azabicyclo[3.1.0]hexan-2-one trifluoroacetate (single enantiomer)

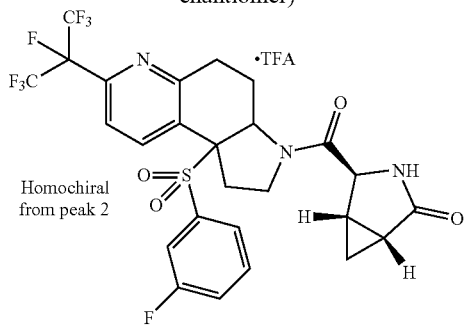

Homochiral from peak 2

A mixture of (3aR,9bR)-9b-((3-fluorophenyl)sulfonyl)-7-(perfluoropropan-2-yl)-2,3,3a,4,5,9b-hexahydro-1H-pyrrolo[3,2-f]quinoline (Intermediate 9; 20.0 mg, 0.040 mmol), (1S,2S,5R)-3-(tert-butoxycarbonyl)-4-oxo-3-azabicyclo[3.1.0]hexane-2-carboxylic acid (Intermediate 14; 11.6 mg, 0.048 mmol), TEA (0.022 mL, 0.160 mmol) and DMF (0.3 mL) was treated with HATU (18.2 mg, 0.048 mmol) and stirred at rt overnight. The mixture was treated with saturated aqueous NaHCO$_3$ (3 mL) and extracted with EtOAc (3×1 mL). The combined organic phases were dried and concentrated. The residue was subjected to column chromatography on silica gel (4 g), eluting with DCM-methanol (gradient from 0-10%), to provide tert-butyl (1S,2S,5R)-2-((3aR,9bR)-9b-((3-fluorophenyl)sulfonyl)-7-(perfluoropropan-2-yl)-2,3,3a,4,5,9b-hexahydro-1H-pyrrolo[3,2-J]quinoline-3-carbonyl)-4-oxo-3-azabicyclo[3.1.0]hexane-3-carboxylate. This material was dissolved in DCE (5 mL) and treated with TFA (0.5 mL). After 25 min the mixture was concentrated and the residue was treated with saturated aqueous NaHCO$_3$ (1 mL) and solid K$_2$CO$_3$. The mixture was extracted with EtOAc, dried and concentrated. A portion of the residue was purified via preparative HPLC (method F, gradient 30-70% B, 20 min) to provide a single enantiomer of (1R,4S,5S)-4-((3aR,9bR)-9b-((3-fluorophenyl)sulfonyl)-7-(perfluoropropan-2-yl)-2,3,3a,4,5,9b-hexahydro-1H-pyrrolo[3,2-J]quinoline-3-carbonyl)-3-azabicyclo[3.1.0]hexan-2-one trifluoroacetate. LCMS m/z 624.2 (M+H)+, HPLC $t_R$ 1.91 min (method C). $^1$H NMR (500 MHz, DMSO-d$_6$) δ 8.45-8.24 (m, 1H), 7.98-7.82 (m, 1H), 7.65-7.51 (m, 2H), 7.36-7.21 (m, 1H), 6.84-6.69 (m, 1H), 4.88-4.19 (m, 2H), 4.00-3.84 (m, 1H), 3.65-3.36 (m, 1H), 2.92-2.71 (m, 1H), 2.67-2.56 (m, 1H), 2.46-2.33 (m, 1H), 2.30-1.84 (m, 3H), 1.79-1.61 (m, 1H), 1.56-1.17 (m, 1H), 1.16-0.51 (m, 2H)

The Example in Table 4 was prepared by following procedures used to prepare Example 34 or similar procedures, from appropriate acid and amine intermediates.

TABLE 4

| Ex. # | Structure | LCMS m/z observed | HPLC $t_R$ (min) | HPLC method |
|---|---|---|---|---|
| 35 | Homochiral from peak 2 | 624.2 (M + H)+ | 1.90 | C |

Example 36

(3R,5S)-3-fluoro-5-(9a-((4-fluorophenyl)sulfon)-3-(perfluoropropan-2-yl)-6,6a,7,8,9,9a-hexahydro-5H-pyrrolo[2,3-h]quinoline-7-carbonyl)-1-(2-hydroxyethyl)pyrrolidin-2-one (Single Enantiomer)

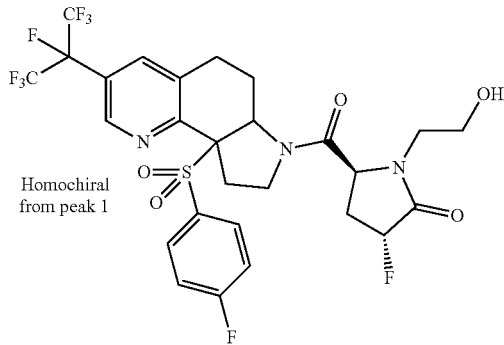 [SMILES: O=C([C@@H]1C[C@@H](F)C(=O)N1CCO)N1CCC2(S(=O)(=O)c3ccc(F)cc3)c3ncc(C(F)(C(F)(F)F)C(F)(F)F)cc3CCC12]

Homochiral from peak 1

A mixture of a single enantiomer of 9a-((4-fluorophenyl)sulfonyl)-3-(perfluoropropan-2-yl)-6,6a,7,8,9,9a-hexahydro-5H-pyrrolo[2,3-h]quinoline dihydrochloride (Intermediate 1; 30.0 mg, 0.056 mmol), crude (2S,4S)-1-(2-((tert-butyldimethylsilyl)oxy)ethyl)-4-fluoro-5-oxopyrrolidine-2-carboxylic acid, lithium salt (Intermediate 15; 26.2 mg, 0.084 mmol), HATU (34.0 mg, 0.089 mmol) and TEA (47 μL, 0.335 mmol) in DMF (800 μL) was stirred at rt overnight. The mixture was filtered and purified by preparative HPLC (method D, gradient 25-100% B, 10 min). The residue from concentration of the appropriate fractions was dissolved in DCM (1.0 mL) and treated with HCl (4 M in 1,4-dioxane; 0.5 mL). The mixture was stirred at rt for 4 h, concentrated, dissolved in DMF, filtered and purified by preparative HPLC (method D, gradient 20-60% B, 20 min) to afford a single enantiomer of (3S,5S)-3-fluoro-5-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-1-(2-hydroxyethyl)pyrrolidin-2-one (10.4 mg, 28% yield). LCMS m/z 674.4 (M+H)⁺, HPLC $t_R$ 1.81 min (method C). ¹H NMR (500 MHz, DMSO-d₆) δ 8.69-8.60 (m, 1H), 7.98-7.87 (m, 1H), 7.59-7.45 (m, 2H), 7.35-7.21 (m, 2H), 5.35-4.77 (m, 3H), 4.03-3.41 (m, 6H), 3.18-3.01 (m, 1H), 2.87-2.55 (m, 5H), 2.48-2.26 (m, 2H), 1.74-1.40 (m, 1H).

The Example in Table 5 was prepared by following procedures used to prepare Example 36 or similar procedures, from appropriate acid and amine intermediates.

Example 38

3-((2S)-2-(3-(benzyloxy)-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile (single enantiomer)

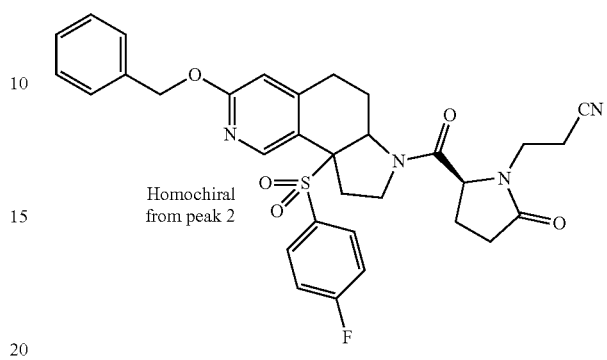

Homochiral from peak 2

A solution of a single enantiomer of 3-(benzyloxy)-9a-((4-fluorophenyl)sulfonyl)-6,6a,7,8,9,9a-hexahydro-5H-pyrrolo[2,3-h]isoquinoline (Intermediate 2; 0.349 g, 0.796 mmol), (S)-1-(2-cyanoethyl)-5-oxopyrrolidine-2-carboxylic acid (Intermediate 11; 0.261 g, 1.43 mmol), HATU (0.545 g, 1.43 mmol) and TEA (0.666 mL, 4.78 mmol) in DMF (13.3 ml) was stirred at rt. After 16 h, the mixture was partitioned between EtOAc and saturated aqueous NaHCO₃. The organic phase was washed sequentially with 10% aqueous LiCl and brine, dried and concentrated. The residue was subjected to column chromatography on silica gel (24 g), eluting with EtOAc-hexanes (60-100%), then with MeOH-EtOAc (5:95), to afford a single enantiomer of 3-((2R)-2-(3-(benzyloxy)-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile as a white foamy solid (0.396 g, 83% yield). LCMS m/z 603.2 (M+H)+, HPLC $t_R$ 0.93 min (method A). ¹H NMR (500 MHz, DMSO-d₆) δ 8.38-8.13 (m, 1H), 7.55-7.22 (m, 9H), 6.70-6.48 (m, 1H), 5.38 (s, 2H), 4.94-4.37 (m, 2H), 3.93-3.49 (m, 4H), 3.43-2.60 (m, 5H), 2.41-2.09 (m, 4H), 1.97-1.68 (m, 2H), 1.53-1.19 (m, 1H).

The Examples in Table 6 were prepared by following procedures used to prepare Example 38 or similar procedures, from appropriate acid and amine intermediates.

TABLE 5

| Ex. # | Structure | LCMS m/z observed | HPLC $t_R$ (min) | HPLC method |
|---|---|---|---|---|
| 37 | ![structure] Homochiral from peak 2 | 716.3 (M + H)⁺ | 2.15 | C |

TABLE 6

| Ex. # | Structure | LCMS m/z observed | HPLC $t_R$ (min) | HPLC method |
|---|---|---|---|---|
| 39 | Homochiral from peak 2 | 671.1 (M + H)+ | 2.14 | C |
| 40 | TFA; Homochiral from peak 2 | 661.0 (M + H)+ | 2.21 | C |

Example 41

3-((2S)-2-(9a-((4-fluorophenyl)sulfon)-3-(perfluoropropan-2-yl)-66a7,8,9,9a-hexahydro-5H-pyrrolo[2,3-h]isoquinoline-7-carbonyl)-5-oxopyrrolidin-1-yl)propanenitrile (Single Enantiomer)

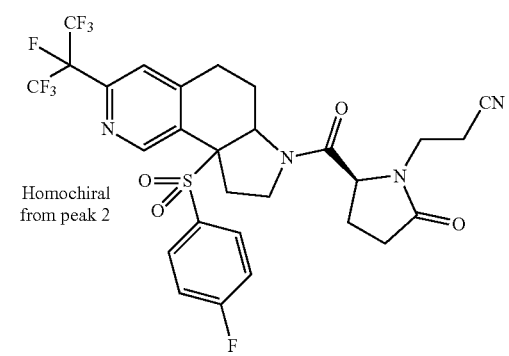 [SMILES: N#CCCN1C(=O)CC[C@H]1C(=O)N1CCC2(S(=O)(=O)c3ccc(F)cc3)c3cnc(C(F)(C(F)(F)F)C(F)(F)F)cc3CCC12]

Homochiral from peak 2

Step A: 3-((2S)-2-(9a-((4-fluorophenyl)sulfonyl)-3-hydroxy-6,6a,7,8,9,9a-hexahydro-5H-pyrrolo[2,3-h]isoquinoline-7-carbonyl)-5-oxopyrrolidin-1-yl)propanenitrile (single enantiomer)

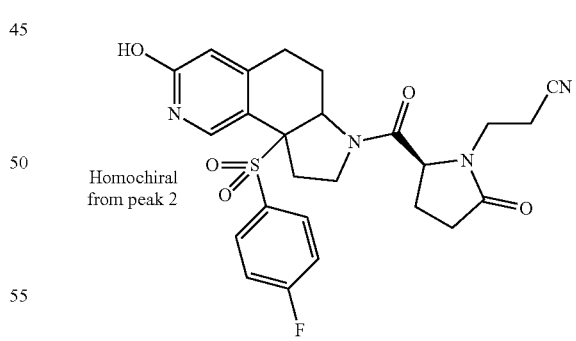

Homochiral from peak 2

A solution of a single enantiomer of 3-((2S)-2-(3-(benzyloxy)-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile (Example 38; 0.350 g, 0.581 mmol) in 1:1 MeOH-EtOAc (19.4 mL) was treated with palladium on carbon (0.093 g). The mixture was stirred under a hydrogen atmosphere (balloon pressure) at rt. After 16 h, additional palladium on carbon (0.093 g) was added and the mixture was stirred again under a hydrogen atmosphere overnight. The mixture was filtered through Celite, the solids were rinsed with EtOAc and the combined filtrates were concentrated to afford a single enantiomer of 3-((2S)-2-(9a-((4-fluorophenyl)sulfonyl)-3-hydroxy-6,6a,7,8,9,9a-hexahydro-5H-pyrrolo[2,3-h]isoquinoline-7-carbonyl)-5-oxopyrrolidin-1-yl)propanenitrile as a white solid (0.281 g, 94% yield). LCMS m/z 513.2 (M+H)+, HPLC $t_R$ 0.56 min (method A).

Step B: 3-((2S)-2-(3-bromo-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile trifluoroacetate (Single Enantiomer)

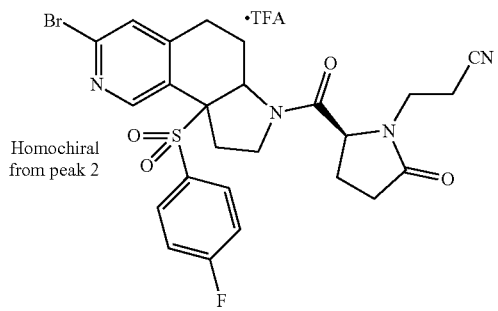 [SMILES: N#CCCN1C(=O)CC[C@H]1C(=O)N1CCC2(S(=O)(=O)c3ccc(F)cc3)c3cnc(Br)cc3CCC12]

A solution of a single enantiomer of 3-((2S)-2-(9a-((4-fluorophenyl)sulfonyl)-3-hydroxy-6,6a,7,8,9,9a-hexahydro-5H-pyrrolo[2,3-h]isoquinoline-7-carbonyl)-5-oxopyrrolidin-1-yl)propanenitrile (114 mg, 0.222 mmol) in DMF (3 mL) was treated with a solution of phosphorus oxybromide (191 mg, 0.667 mmol) in toluene (1.5 mL) and the resulting mixture was heated at 90° C. After 5.5 h, the mixture was cooled to rt and treated with MeOH and a few drops of water, then was concentrated. The residue was dissolved in DMF-MeOH and purified by preparative HPLC (method E, gradient 10-100% B, 10 min) to provide a single enantiomer of 3-((2S)-2-(3-bromo-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile trifluoroacetate as brown solid (39 mg, 25% yield). LCMS m/z 575.1, 577.1 (M+H)+, HPLC $t_R$ 0.80 min (method A).

Step C: 3-((2S)-2-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-5-oxopyrrolidin-1-yl)propanenitrile (Single Enantiomer)

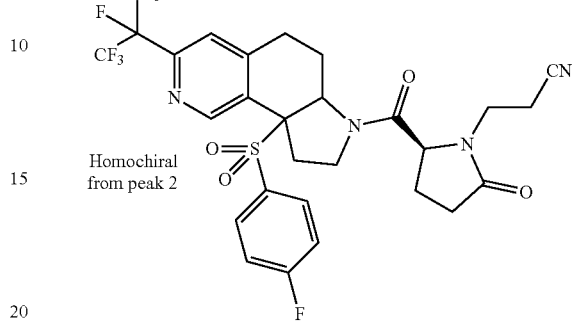

Following the procedure of Intermediate 1, Step F, a single enantiomer of 3-((2S)-2-(3-bromo-9a-((4-fluorophenyl)sulfonyl)-6,6a,7,8,9,9a-hexahydro-5H-pyrrolo[2,3-h]isoquinoline-7-carbonyl)-5-oxopyrrolidin-1-yl)propanenitrile trifluoroacetate (33 mg) was converted into a single enantiomer of 3-((2S)-2-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-5-oxopyrrolidin-1-yl)propanenitrile trifluoroacetate after purification by preparative HPLC (method E, gradient from 10-100% B, 10 min). This material was partitioned between saturated aqueous NaHCO$_3$ and EtOAc, and the organic phase was dried and concentrated to provide the free base (9 mg, 22% yield). LCMS m/z 665.2 (M+H)+, HPLC $t_R$ 0.98 min (method A). $^1$H NMR (499 MHz, MeOH-d$_4$) δ 9.00 (s, 1H), 7.52 (d, J=2.6 Hz, 1H), 7.48-7.39 (m, 2H), 7.18 (t, J=8.7 Hz, 2H), 4.95 (dd, J=12.0, 5.0 Hz, 1H), 4.83 (dd, J=8.4, 3.2 Hz, 1H), 4.13 (q, J=8.9 Hz, 1H), 3.92-3.83 (m, 2H), 3.68 (ddd, J=14.7, 8.1, 3.0 Hz, 1H), 2.90-2.69 (m, 4H), 2.57-2.41 (m, 4H), 2.14-2.00 (m, 2H), 1.43 (qd, J=12.7, 3.2 Hz, 1H).

The Example in Table 7 was prepared by following procedures used to prepare Example 41 or similar procedures, from the appropriate starting material.

TABLE 7

| Ex. # | Structure | LCMS m/z observed | HPLC $t_R$ (min) | HPLC method |
|---|---|---|---|---|
| 42 | CF$_3$, F, CF$_3$, •TFA (structure), Homochiral from peak 2 | 665.2 (M + H)+ | 0.99 | A |

Examples 43 and 44

(3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer) and (3R,5R)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (Single Enantiomer)

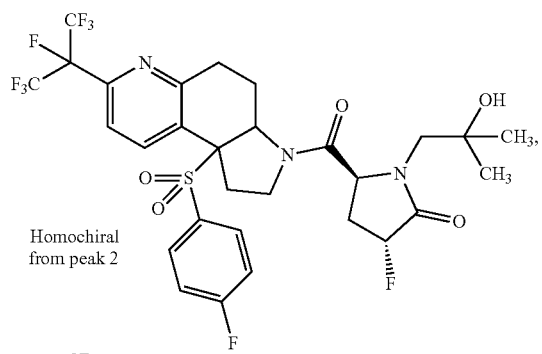

Homochiral from peak 2

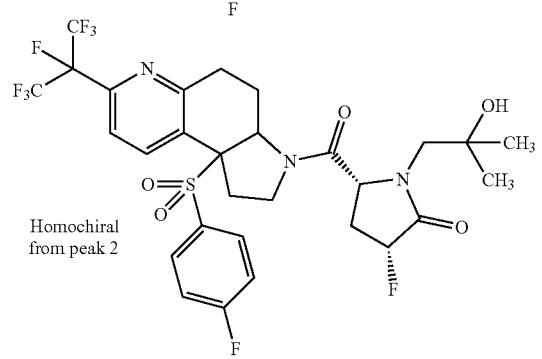

Homochiral from peak 2

Step A: (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)pyrrolidin-2-one trifluoroacetate (Single Enantiomer)

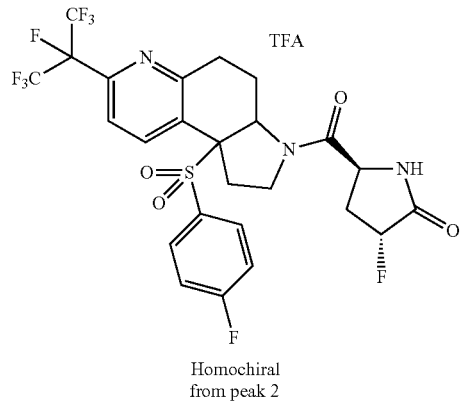 [SMILES: O=C1N[C@H](C(=O)N2CCC3(S(=O)(=O)c4ccc(F)cc4)c4ccc(C(F)(C(F)(F)F)C(F)(F)F)nc4CCC23)C[C@H]1F]

Homochiral from peak 2

A mixture of a single enantiomer of 9b-((4-fluorophenyl)sulfonyl)-7-(perfluoropropan-2-yl)-2,3,3a,4,5,9b-hexahydro-1H-pyrrolo[3,2-f]quinoline (Intermediate 8, 35.0 mg, 0.070 mmol), HATU (53.2 mg, 0.140 mmol), DIEA (48.9 µL. 0.280 mmol), and (2S,4R)-4-fluoro-5-oxopyrrolidine-2-carboxylic acid (Intermediate 12, 41.2 mg, 0.140 mmol) in DMF (874 µL) was stirred at rt. After 20 h the mixture was partitioned between EtOAc and saturated aqueous NaHCO$_3$. The organic phase was washed sequentially with 10% aqueous LiCl and brine, dried and concentrated. The residue was purified by preparative HPLC (method E) to provide a single enantiomer of (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)pyrrolidin-2-one trifluoroacetate as a light yellow solid (18 mg, 41% yield). LCMS m/z 630.1 (M+H)$^+$, HPLC t$_R$ 0.98 min (method A).

Step B: (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer) and (3R,5R)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (Single Enantiomer)

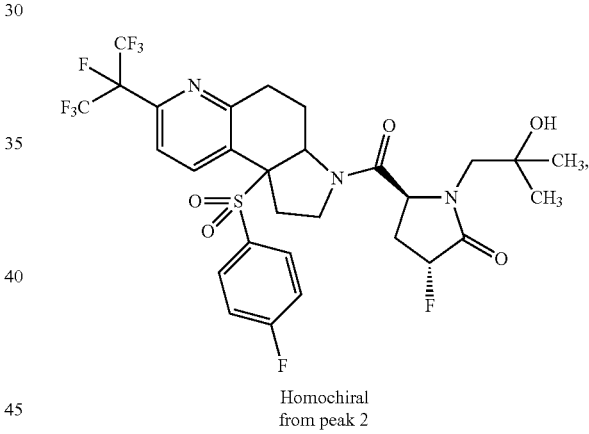

Homochiral from peak 2

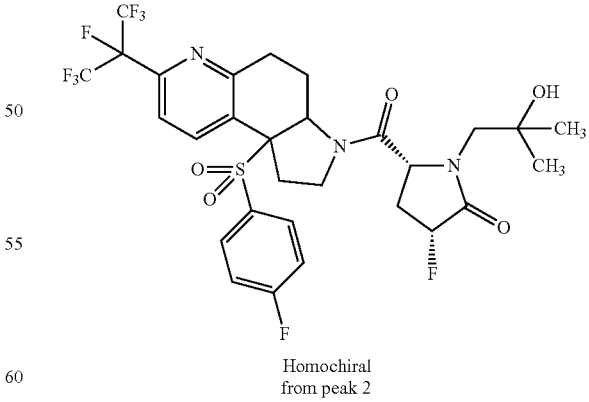

Homochiral from peak 2

A mixture of a single enantiomer of (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-J]quinoline-3-carbonyl)pyrrolidin-2-one trifluoroacetate (18.0 mg, 0.029 mmol) and K$_2$CO$_3$ (5.93 mg, 0.043 mmol) in IPA (357 µL) was treated with 2,2-dimethyloxirane (39.7 μL, 0.458 mmol) and heated at 100° C. overnight. The mixture was cooled to rt and purified by preparative HPLC (method D, gradient 36-76% B, 25 min) to provide a single enantiomer of (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-]quinoline-3-carbonyl)-1-(2-hydroxy-2-methylpropyl)pyrrolidin-2-one (6.7 mg, 33% yield). LCMS m/z 702.2 (M+H)$^+$, HPLC $t_R$ 2.18 min (method C). $^1$H NMR (500 MHz, DMSO-d$_6$) δ 8.31 (br d, J=8.3 Hz, 1H), 7.86 (br d, J=8.2 Hz, 1H), 7.44-7.34 (m, 2H), 7.34-7.16 (m, 2H), 5.34-5.09 (m, 1H), 4.83-4.69 (m, 2H), 3.86-3.78 (m, 1H), 3.77-3.68 (m, 1H), 3.61 (br d, J=14.1 Hz, 1H), 3.49-3.25 (m, 4H), 2.87-2.77 (m, 1H), 2.67 (br d, J=14.4 Hz, 2H), 2.22-2.11 (m, 1H), 1.88-1.72 (m, 1H), 1.60-1.46 (m, 1H), 1.10 (s, 3H), 1.01 (s, 3H). Also isolated was a single enantiomer of (3R,5R)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (2.2 mg, 10% yield). LCMS m/z 702.3 (M+H)$^+$, HPLC $t_R$ 2.09 min (method C).

The Examples in Table 8 were prepared by following procedures used to prepare Examples 43 and 44 or similar procedures, from the appropriate starting materials.

TABLE 8

| Ex. # | Structure | LCMS m/z observed | HPLC $t_R$ (min) | HPLC method |
|---|---|---|---|---|
| 45 | Homochiral from peak 2 | 702.0 (M + H)$^+$ | 2.17 | C |
| 46 | Homochiral from peak 2 | 702.2 (M + H)$^+$ | 2.02 | C |
| 47 | Homochiral from peak 2 | 702.2 (M + H)$^+$ | 2.23 | C |

TABLE 8-continued

| Ex. # | Structure | LCMS m/z observed | HPLC t_R (min) | HPLC method |
|---|---|---|---|---|
| 48 | (structure; Homochiral from peak 2) | 702.2 (M + H)+ | 2.19 | C |
| 49 | (structure; ·TFA; Homochiral from peak 2) | 696.3 (M + H)+ | 2.00 | C |
| 50 | (structure; ·TFA; Homochiral from peak 1) | 702.3 (M + H)+ | 2.03 | C |
| 51 | (structure; Homochiral from peak 1) | 696.1 (M + H)+ | 1.94 | C |

TABLE 8-continued

| Ex. # | Structure | LCMS m/z observed | HPLC $t_R$ (min) | HPLC method |
|---|---|---|---|---|
| 52 | (Homochiral from peak 2) | 696.3 (M + H)⁺ | 1.97 | C |
| 53 | (Homochiral from peak 2) | 683.9 (M + H)⁺ | 2.13 | C |

Example 54

1-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-2-(2-hydroxy-2-methylpropyl)pyrazolidin-3-one (Single Enantiomer)

Step A: 1-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)pyrazolidin-3-one (Single Enantiomer)

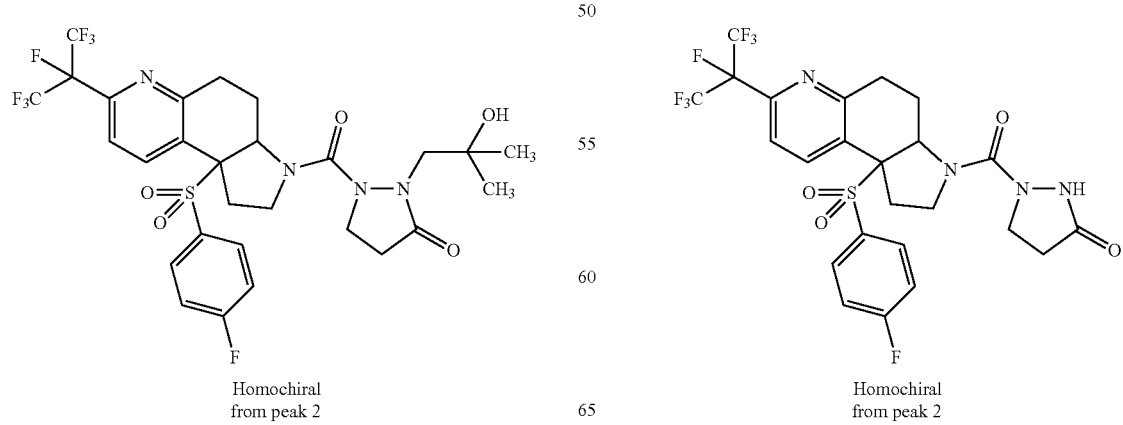

Homochiral from peak 2

Homochiral from peak 2

A solution of 9b-((4-fluorophenyl)sulfonyl)-7-(perfluoropropan-2-yl)-2,3,3a,4,5,9b-hexahydro-1H-pyrrolo[3,2-J]quinoline (Intermediate 8; 35 mg, 0.070 mmol) in DCM (874 μL) was cooled in a dry ice-acetone bath and treated dropwise with 20% phosgene in toluene (92 μL, 0.175 mmol), then was treated dropwise with DIEA (49 μL, 0.280 mmol). The mixture was stirred for 20 min, then the cooling bath was removed and the mixture was stirred for 40 min while warming to rt. The solution was concentrated to give a white solid, which was dissolved in DCE (0.9 mL) and treated with pyrazolidin-3-one hydrochloride (17.1 mg, 0.140 mmol) and DIEA (49 μL, 0.280 mmol). The mixture was heated at 60° C. for 6 h. After cooling to rt, the mixture was partitioned between DCM and saturated aqueous NaHCO₃. The organic phase was washed with brine, dried and concentrated to provide a single enantiomer of 1-(9b-((4-fluorophenyl)sulfonyl)-7-(perfluoropropan-2-yl)-2,3,3a,4,5,9b-hexahydro-1H-pyrrolo[3,2-]quinoline-3-carbonyl)pyrazolidin-3-one as light yellow solid (32 mg, 75% yield), used without further purification. LCMS m/z 613.1 (M+H)⁺, HPLC $t_R$ 0.96 min (method A).

Step B: 1-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-2-(2-hydroxy-2-methylpropyl)pyrazolidin-3-one (Single Enantiomer)

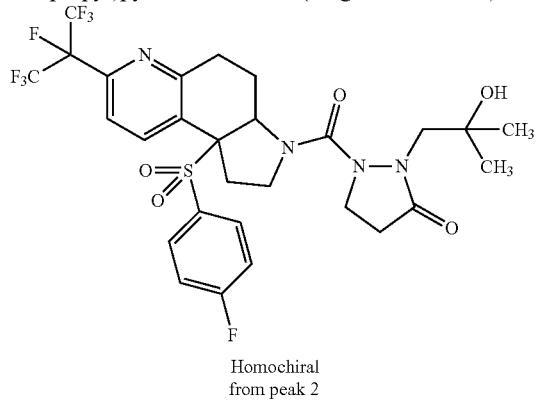

Homochiral from peak 2

Following the procedure of Example 43, Step B, a single enantiomer of 1-(9b-((4-fluorophenyl)sulfonyl)-7-(perfluoropropan-2-yl)-2,3,3a,4,5,9b-hexahydro-1H-pyrrolo[3,2-J]quinoline-3-carbonyl)pyrazolidin-3-one was converted to a single enantiomer of 1-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-2-(2-hydroxy-2-methylpropyl)pyrazolidin-3-one in 27% yield. LCMS m/z 685.1 (M+H)⁺, HPLC $t_R$ 2.19 min (method C).

The Examples in Table 9 were prepared by following procedures used to prepare Example 54 or similar procedures, from the appropriate starting materials.

TABLE 9

| Ex. # | Structure | LCMS m/z observed | HPLC $t_R$ (min) | HPLC method |
|---|---|---|---|---|
| 55 | 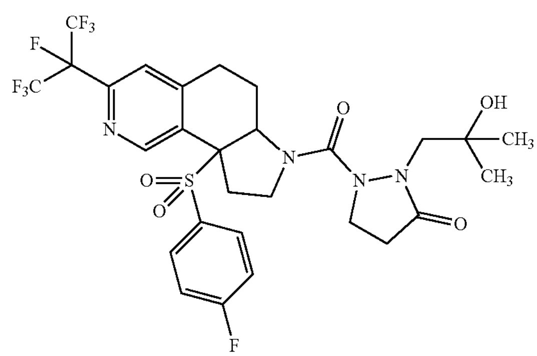 | 685.1 (M + H)⁺ | 2.15 | C |
| 56 | 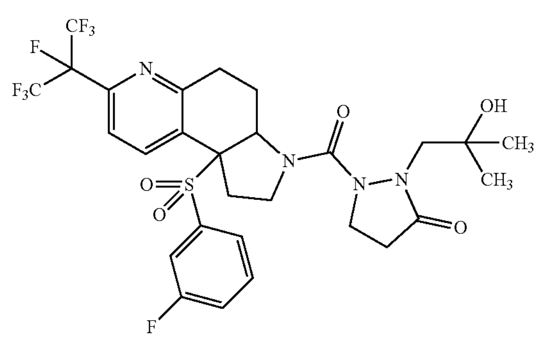 | 685.1 (M + H)⁺ | 2.18 | C |

Homochiral from peak 2

Homochiral from peak 2

TABLE 9-continued

| Ex. # | Structure | LCMS m/z observed | HPLC $t_R$ (min) | HPLC method |
|---|---|---|---|---|
| 57 | 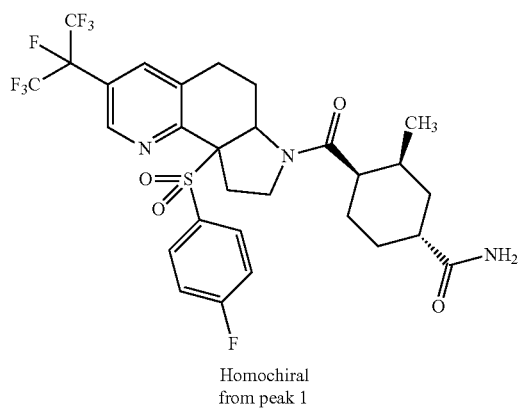 [SMILES: C[C@H]1C[C@H](C(N)=O)CC[C@H]1C(=O)N1CCC2(S(=O)(=O)c3ccc(F)cc3)c3ncc(C(F)(C(F)(F)F)C(F)(F)F)cc3CCC12] Homochiral from peak 1 | 685.1 (M + H)+ | 1.95 | C |
| 58 | Homochiral from peak 2 | 667.4 (M + H)+ | 1/98 | C |

Example 59

(1R,3S,4R)-4-(9a-((4-fluorophenyl)sulfon)-3-(perfluoropropan-2-yl)-666a,7,8,9,9a-hexahydro-5H-pyrrolo[2,3-h]quinoline-7-carbonyl)-3-methylcyclohexane-1-carboxamide (Single Enantiomer)

Homochiral from peak 1

A mixture of a single enantiomer of impure (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxylic acid (Example 23, 80 mg, 0.048 mmol, about 40% pure), NH$_4$OH (19 μL, 0.479 mmol) and HATU (45.5 mg, 0.120 mmol) in DMF (957 μL) was stirred at rt overnight. The mixture was purified by preparative HPLC (method D, gradient 30-70% B, 20 min) to provide a single enantiomer of (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxamide (5.2 mg, 16% yield). LCMS m/z 668.4 (M+H)+, HPLC $t_R$ 1.861 min (method C). $^1$H NMR (500 MHz, DMSO-d$_6$) δ 8.31 (br d, J=8.3 Hz, 1H), 7.86 (br d, J=8.2 Hz, 1H), 7.44-7.34 (m, 2H), 7.34-7.1-8.61 (s, 1H), 7.91 (br. s., 1H), 7.49-7.39 (m, 2H), 7.33-7.20 (m, 3H), 6.63 (br. s., 1H), 4.95 (dd, J=11.6, 5.2 Hz, 1H), 3.94-3.83 (m, 1H), 3.73-2.56 (m, 4H), 2.44-2.23 (m, 3H), 1.91-1.19 (m, 8H), 0.91 (d, J=7.0 Hz, 3H).

Example 60

2,2,2-trifluoro-1-(9a-((3-fluorophenyl)sulfonyl)-3-(perfluoropropan-2-yl)-5,6,6a,8,9,9a-hexahydro-7H-pyrrolo[2,3-h]isoquinolin-7-yl)ethan-1-one (Single Enantiomer)

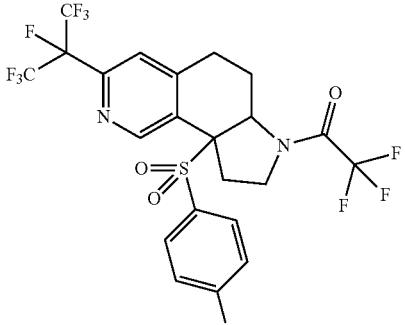

Homochiral from peak 1

Following the procedures of Intermediate 4, Steps A through G, 3-(benzyloxy)-6,7-dihydroisoquinolin-8(5H)-one (Intermediate 2, Step A) was converted into a single enantiomer of 2,2,2-trifluoro-1-(9a-((3-fluorophenyl)sulfonyl)-3-(perfluoropropan-2-yl)-5,6,6a,8,9,9a-hexahydro-7H-pyrrolo[2,3-h]isoquinolin-7-yl)ethan-1-one. LCMS m/z 597.2 (M+H)$^+$, HPLC $t_R$ 1.12 min (method A). $^1$H NMR (499 MHz, CDCl$_3$) δ 9.06 (s, 1H), 7.41-7.35 (m, 1H), 7.35-7.30 (m, 2H), 7.20 (d, J=7.7 Hz, 1H), 6.99 (dt, J=7.7, 2.0 Hz, 1H), 4.93 (dd, J=11.9, 4.9 Hz, 1H), 4.25-4.17 (m, 1H), 4.02-3.94 (m, 1H), 3.72 (ddd, J=14.5, 8.0, 2.8 Hz, 1H), 2.74-2.60 (m, 3H), 2.08-1.99 (m, 1H), 1.33 (qd, J=12.6, 3.1 Hz, 1H).

The Examples in Table 10 were prepared by following procedures used to prepare Example 60 or similar procedures, from the appropriate starting materials.

TABLE 10

| Ex. # | Structure | LCMS m/z observed | HPLC $t_R$ (min) | HPLC method |
|---|---|---|---|---|
| 61 | Homochiral from peak 2 | 585.3 (M + H)$^+$ | 2.59 | C |
| 62 | Homochiral from peak 1 | 585.2 (M + H)$^+$ | 2.54 | C |

The Examples in Table 11 were prepared by following procedures used to prepare Example 1 or similar procedures, from the appropriate starting materials.

TABLE 11

| Ex. # | Structure | LCMS m/z observed | HPLC $t_R$ (min) | HPLC method |
|---|---|---|---|---|
| 63 | •TFA Homochiral from peak 2 | 647.4 (M + H)$^+$ | 2.05 | C |

TABLE 11-continued

| Ex. # | Structure | LCMS m/z observed | HPLC $t_R$ (min) | HPLC method |
|---|---|---|---|---|
| 64 | 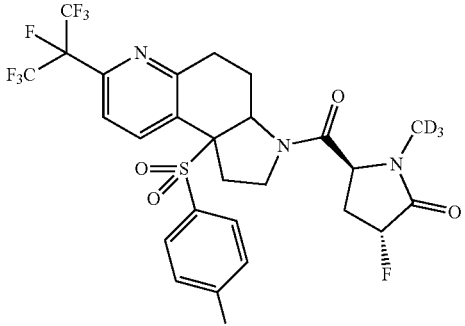<br>Homochiral from peak 2 | 647.1 (M + H)+ | 2.15 | C |
| 65 | 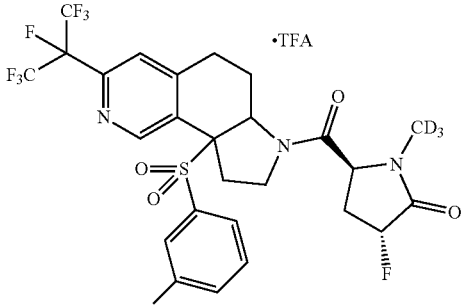<br>Homochiral from peak 1 | 647.1 (M + H)+ | 1.99 | C |
| 66 | 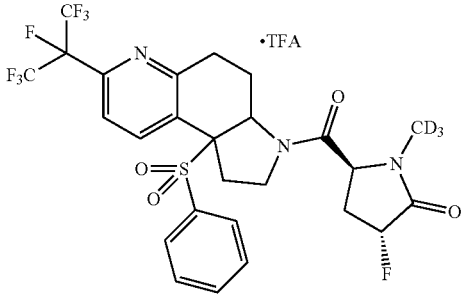<br>Homochiral from peak 2 | 629.1 (M + H)+ | 2.11 | C |

General RORγ Gal4 Reporter Assay Inverse agonist activity of potential ligands to RORγ was measured by inhibition of luminescence in a Gal4-luciferase reporter assay in Jurkat cells.

Jurkat cells stably over-expressing the RORγ receptor, Jurkat pEx/Gal/hRORγ CLBD/HYG pG5luc/blast, were plated at a concentration of 10,000 cells/well in a 384-well solid white cell culture plate (Perkin Elmer #6007899) in assay buffer RPMI 1640 (Gibco 11875-085 1 L) containing 0.1% BSA, 100×HEPES (Gibco 15360-080), 100 mM sodium pyruvate (Gibco 11360-040), 50 mg/mL Hygromycin B (Invitrogen 10687-010) and 10 mg/mL blasticidin (Invitrogen R210-01). 100 nL of test compound in a 3-fold serial dilution, with final concentrations ranging from 40 μM to 0.67 nM, were added to the cells which were then incubated overnight.

The following day, cells were lysed with 10 μL of Steady-Glo Luciferase Assay System (Promega Cat. No. EZ550), and analyzed immediately. $IC_{50}$ values were determined. The $IC_{50}$ value is defined as the concentration of test compound needed to reduce luciferase activity by 50% and is calculated using the four parameter logistic equation to fit the normalized data.

$IC_{50}$ values for compounds of the invention in the RORγ Gal4 reporter assay are provided below.

| Ex. No. | RORγ Gal4 $IC_{50}$, μM |
|---|---|
| 1 | 0.093 |
| 2 | 0.069 |
| 3 | 0.061 |
| 4 | 0.161 |
| 5 | 0.078 |
| 6 | 0.054 |
| 7 | 0.083 |
| 8 | 0.091 |

-continued

| Ex. No. | RORγ Gal4 IC$_{50}$, μM |
|---|---|
| 9 | 0.087 |
| 10 | 0.033 |
| 11 | 0.021 |
| 12 | 0.009 |
| 13 | 0.019 |
| 14 | 0.004 |
| 15 | 0.008 |
| 16 | 0.006 |
| 17 | 0.045 |
| 18 | 0.030 |
| 19 | 0.013 |
| 20 | 0.006 |
| 21 | 0.011 |
| 22 | 0.009 |
| 23 | 0.318 |
| 24 | 0.015 |
| 25 | 0.012 |
| 26 | 0.013 |
| 27 | 0.021 |
| 28 | 0.008 |
| 29 | 0.013 |
| 30 | 0.051 |
| 31 | 0.017 |
| 32 | 0.005 |
| 33 | 0.008 |
| 34 | 0.062 |
| 35 | 3.305 |
| 36 | 0.110 |
| 37 | 0.009 |
| 38 | 4.25 |
| 39 | 0.015 |
| 40 | 0.012 |
| 41 | 0.034 |
| 42 | 0.043 |
| 43 | 0.031 |
| 44 | 0.168 |
| 45 | 0.528 |
| 46 | 0.410 |
| 47 | 0.029 |
| 48 | 0.026 |
| 49 | 0.018 |
| 50 | 0.014 |
| 51 | 0.022 |
| 52 | 1.810 |
| 53 | 0.018 |
| 54 | 0.016 |
| 55 | 0.031 |
| 56 | 0.028 |
| 57 | 0.021 |
| 58 | 0.012 |
| 59 | 0.594 |
| 60 | 0.082 |
| 61 | 0.802 |
| 62 | 2.440 |
| 63 | 0.013 |
| 64 | 0.024 |
| 65 | 0.091 |
| 66 | 0.031 |

What is claimed is:

1. The compound of the Formula (I)

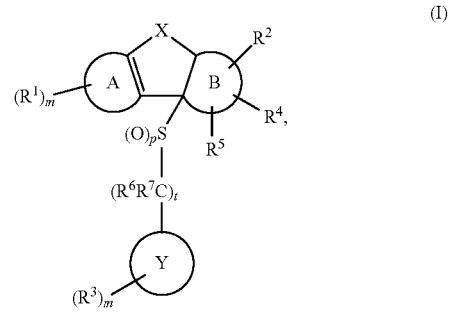

or a stereoisomer or pharmaceutically acceptable salt thereof, wherein

X is —CR$^4$R$^5$—, —(CR$^4$R$^5$)$_2$—, —OCR$^6$R$^7$—, —S(O)$_p$CR$^6$R$^7$—, —S(O)(NR$^g$)CR$^6$R$^7$— or —NR$^6$CR$^6$R$^7$—;

A is a monocyclic 5- or 6-membered heteroaromatic ring;

B is a monocyclic 5- or 6-membered heterocyclic ring;

Y is a 5 or 6-membered aromatic or heteroaromatic ring;

R$^1$ is, independently at each occurrence, selected from hydrogen, CD$_3$, halo, OCF$_3$, CN, S(O)$_p$(C$_1$-C$_6$)alkyl, S(O)(NR$^g$)(C$_1$-C$_6$)alkyl, —S(O)$_p$(C$_1$-C$_6$)alkyl-OH, S(O)(NR$^g$)(C$_1$-C$_6$)alkyl-OH, -thioalkoxyalkoxy, NR$^{11}$R$^{11}$, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—R$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^2$ is selected from hydrogen, CN, —(CR$^{2e}$R$^{2f}$)$_r$—C(O)R$^{2d}$, —(CR$^{2e}$R$^{2f}$)$_r$—C(O)OR$^{2b}$, —(CR$^{2e}$R$^{2f}$)$_r$—C(O)NR$^{11}$R$^{11}$, —(CR$^{2e}$R$^{2f}$)$_r$—S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)$_r$-3-10 membered carbocycle substituted with 0-4 R$^a$, and —(CR$^{2e}$R$^{2f}$)$_r$-4-7 membered heterocycle comprising carbon atoms, and 1-4 heteroatoms selected from N, O, P(O), S(O)$_p$ and S(O)(NR$^g$), substituted with 0-4 R$^a$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)

$OR^b$, $-(CR^{2e}R^{2f})_r-OC(O)R^b$, $-(CR^{2e}R^{2f})_r-OC(O)NR^{11}R^{11}$, $-(CR^{2e}R^{2f})_r-OC(O)OR^c$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r-3-14$ membered carbocycle substituted with 0-3 $R^a$, or $-(CR^{2e}R^{2f})_r-4-7$ membered heterocycle comprising carbon atoms, and 1-4 heteroatoms selected from N, O, $S(O)_p$ and $S(O)(NR^g)$, substituted with 0-4 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})_qS(O)(NR^g)R^b$, $-(CR^{2e}R^{2f})_r-C(O)R^c$, $-(CR^{2e}R^{2f})_r-C(O)OR^b$, $-(CR^{2e}R^{2f})_qOC(O)R^b$, $-(CR^{2e}R^{2f})_qNR^{11}R^{11}$, $-(CR^{2e}R^{2f})_r-C(O)NR^{11}R^{11}$, $-(CR^{2e}R^{2f})_q NR^bC(O)R^c$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-2 $R^a$, $C_{1-6}$ haloalkyl, $-(CR^{2e}R^{2f})_r-3-14$ membered carbocycle substituted with 0-3 $R^a$, or $-(CR^{2e}R^{2f})_r-5-7$ membered heterocycle comprising carbon atoms and 1-4 heteroatoms selected from N, O, $S(O)_p$ and $S(O)(NR^g)$, substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})_r-5-10$ membered heterocycle containing 1-4 heteroatoms selected from N, O, $S(O)_p$ and $S(O)(NR^g)$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $-(CR^{2e}R^{2f})_r-C_{3-10}$ cycloalkyl substituted with 0-3 $R^d$, where the cycloalkyl ring may be fused, bridged or spirocyclic, $-(CR^{2e}R^{2f})_r$-phenyl substituted with 0-2 $R^a$, or a $-(CR^{2e}R^{2f})_r-4-10$ membered heterocycle where the heterocycle may be fused, bridged or spirocyclic, containing 1-4 heteroatoms selected from N, O, $S(O)_p$ and $S(O)(NR^g)$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, $-(CR^{1b}R^{1c})_r-OR^{3b}$, $-(CR^{1b}R^{1c})_r-NR^{11}R^{11}$, $C_{1-6}$ alkyl substituted with 0-3 $R^{3a}$, $C_{3-10}$ cycloalkyl substituted with 0-3 $R^{3a}$ and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, $S(O)_p$ and $S(O)(NR^g)$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $-(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{1b}R^{1c})_r-3-14$ membered carbocycle substituted with 0-3 $R^a$, or $-(CR^{1b}R^{1c})_r-5-10$ membered heterocycle comprising carbon atoms and 1-4 heteroatoms selected from N, O, $S(O)_p$ and $S(O)(NR^g)$, substituted with 0-3 $R^a$;

$R^{3b}$ is, independently at each occurrence, hydrogen, $CF_3$, $-(CR^{1b}R^{1c})_qOR^b$, $-(CR^{1b}R^{1c})_qS(O)_pR^b$, $-(CR^{1b}R^{1c})_qS(O)(NR^g)R^b$, $-(CR^{1b}R^{1c})_r-C(O)R^{3d}$, $-(CR^{1b}R^{1c})_r-C(O)OR^b$, $-(CR^{1b}R^{1c})_qOC(O)R^b$, $-(CR^{1b}R^{1c})_qNR^{11}R^{11}$, $-(CR^{1b}R^{1c})_r-C(O)NR^{11}R^{11}$, $-(CR^{1b}R^{1c})_qNR^bC(O)R^{3c}$, $-(CR^{1b}R^{1c})_qNR^bC(O)OR^c$, $-(CR^{1b}R^{1c})_qNR^bC(O)NR^{11}R^{11}$, $-(CR^{1b}R^{1c})_qS(O)_2NR^{11}R^{11}$, $-(CR^{1b}R^{1c})_qNR^bS(O)_2R^c$, $C_{1-6}$ alkyl substituted with 0-3 $R^a$, $C_{1-6}$ haloalkyl, $-(CR^{1b}R^{1c})_r-3-14$ membered carbocycle substituted with 0-3 $R^a$, or $-(CR^{1b}R^{1c})_r-5-7$ membered heterocycle comprising carbon atoms and 1-4 heteroatoms selected from N, O, $S(O)_p$ and $S(O)(NR^g)$, substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C(=O)C_{1-4}$ alkyl, $C(=O)OC_{1-4}$ alkyl, $C_{1-6}$ alkyl or $C_{1-6}$ haloalkyl; or $R^6$ and $R^7$ taken together are =O;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $-(CR^{1b}R^{1c})_r$-phenyl substituted with 0-3 $R^d$, or $-(CR^{1b}R^{1c})_r-5-7$ membered heterocycle comprising carbon atoms and 1-4 heteroatoms selected from N, O, $S(O)_p$ and $S(O)(NR^g)$, substituted with 0-4 $R^d$;

or one $R^{11}$ and a second $R^{11}$, both attached to the same nitrogen atom, combine to form a heterocycle comprising carbon atoms and 1-4 heteroatoms selected from N, O, $S(O)_p$ and $S(O)(NR^g)$, substituted with 0-4 $R^d$;

$R^a$ is, independently at each occurrence, hydrogen, =O, halo, $OCF_3$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $-(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, $-(CR^{1b}R^{1c})_r-3-14$ membered carbocycle, or $-(CR^{1b}R^{1c})_r-5-7$ membered heterocycle comprising carbon atoms and 1-4 heteroatoms selected from N, O, $S(O)_p$ and $S(O)(NR^g)$, substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, $-(CR^{1b}R^{1c})_r-5-7$ membered heterocycle comprising carbon atoms and 1-4 heteroatoms selected from N, O, $S(O)_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^c$, —(CR$^{1b}$R$^{1c}$)$_r$—C(O)R$^c$, —NR$^e$R$^e$, —NR$^e$C(O)OR$^c$, C(O)NR$^e$R$^e$, —NRC(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C1-6 alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;
p and q are, independently at each occurrence, 0, 1, or 2;
r is 0, 1, 2, 3, or 4; and
t is 0 or 1.

2. A compound according to claim 1 of the formula

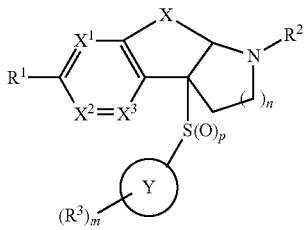

wherein
X is —CR$^4$R$^5$—, —(CR$^4$R$^5$)$_2$—, —OCR$^6$R$^7$—, —S(O)$_p$CR$^6$R$^7$—, —S(O)(NR$^g$)CR$^6$R$^7$— or —NR$^6$CR$^6$R$^7$—;
X$^1$, X$^2$, and X$^3$ are, independently, selected from N or CR$^{1d}$, wherein at least of X$^1$, X$^2$, and X$^3$ is N;
Y is a 5 or 6-membered aromatic or heteroaromatic ring;
R$^1$ is selected from hydrogen, CD$_3$, halo, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is selected from hydrogen, CN, —(CR$^{2e}$R$^{2f}$)$_r$—C(O)R$^{2d}$, —(CR$^{2e}$R$^{2f}$)$_r$—C(O)OR$^{2b}$, —(CR$^{2e}$R$^{2f}$)$_r$—C(O)NR$^{11}$R$^{11}$, —(CR$^{2e}$R$^{2f}$)$_r$—S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)$_r$-3-10 membered carbocycle substituted with 0-4 R$^a$, and —(CR$^{2e}$R$^{2f}$)$_r$-4-7 membered heterocycle comprising carbon atoms, and 1-4 heteroatoms selected from N, O, P(O), S(O)$_p$ and S(O)(NR$^g$), substituted with 0-4 R$^a$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-

10 membered heterocycle containing 1-4 heteroatoms selected from N, O, S(O)$_p$ and S(O)(NR$^g$), substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)$_r$—C$_{3-10}$ cycloalkyl substituted with 0-3 R$^d$, where the cycloalkyl ring may be fused, bridged or spirocyclic, —(CR$^{2e}$R$^{2f}$)$_r$-phenyl substituted with 0-2 R$^a$, or a —(CR$^{2e}$R$^{2f}$)$_r$-4-10 membered heterocycle where the heterocycle may be fused, bridged or spirocyclic, containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_q$—C(O)R$^{3d}$, —(CR$^{1b}$R$^{1c}$)$_q$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^e$, C(O)NR$^e$R$^e$, —NR$^e$C(O)R$^e$, CO$_2$H, CO$_2$R$^e$, —NR$^e$SO$_2$R$^e$, SO$_2$R$^e$, SO(NR$^g$)R$^e$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C1-6 alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;

n is 0, 1 or 2;
p and q are, independently at each occurrence, 0, 1, or 2; and
r is 0, 1, 2, 3, or 4;
or a stereoisomer or pharmaceutically-acceptable salt thereof.

3. A compound according to claim 2 of the formula

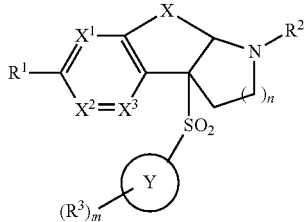

wherein
X is —CR$^4$R$^5$—, —(CR$^4$R$^5$)$_2$—, —OCR$^6$R$^7$—, —S(O)$_p$CR$^6$R$^7$—, —S(O)(NR$^g$)CR$^6$R$^7$— or —NR$^6$CR$^6$R$^7$—;
X$^1$, X$^2$, and X$^3$ are, independently, selected from N or CR$^{1d}$, wherein at least of X$^1$, X$^2$, and X$^3$ is N;
Y is a 5 or 6-membered aromatic or heteroaromatic ring;
R$^1$ is selected from halo, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;
R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;
R$^{1b}$ and R$^{1c}$ are, independently at each occurrence, hydrogen, halogen or C$_{1-6}$ alkyl;
R$^{1d}$ is, independently at each occurrence, hydrogen, CD$_3$, halo, CF$_3$, and C$_1$-C$_4$ alkyl;
R$^2$ is selected from hydrogen, CN, —(CR$^{2e}$R$^{21}$)$_r$—C(O)R$^{2d}$, —(CR$^{2e}$R$^{2f}$)$_r$—C(O)OR$^{2b}$, —(CR$^{2e}$R$^{2f}$)$_r$—C(O)NR$^{11}$R$^{11}$, —(CR$^{2e}$R$^{2f}$)$_r$—S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)$_r$-3-10 membered carbocycle substituted with 0-4 R$^a$, and —(CR$^{2e}$R$^{2f}$)$_r$-4-7 membered heterocycle comprising carbon atoms, and 1-4 heteroatoms selected from N, O, P(O), S(O)$_p$ and S(O)(NR$^g$), substituted with 0-4 R$^a$;
R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;
R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;
R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;
R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)$_r$—C$_{3-10}$ cycloalkyl substituted with 0-3 R$^d$, where the cycloalkyl ring may be fused, bridged or spirocyclic, —(CR$^{2e}$R$^{2f}$)$_r$-phenyl substituted with 0-2 R$^a$, or a —(CR$^{2e}$R$^{2f}$)$_r$-4-10 membered heterocycle where the heterocycle may be fused, bridged or spirocyclic, containing 1-4 heteroatoms selected from N, O, S(O)$_p$ and S(O)(NR$^g$), substituted with 0-4 R$^a$;
R$^{2e}$ and R$^{2f}$ are, independently at each occurrence, hydrogen, halogen or C$_{1-6}$ alkyl;
R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;
R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_q$—C(O)R$^{3d}$, —(CR$^{1b}$R$^{1c}$)$_q$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^3$c, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^1$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^c$, —(CR$^{1b}$R$^{1c}$)$_r$—C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^1$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;

n is 0, 1 or 2;

p and q are, independently at each occurrence, 0, 1, or 2; and r is 0, 1, 2, 3, or 4;

or a stereoisomer or pharmaceutically-acceptable salt thereof.

4. A compound according to claim 3 of the formula

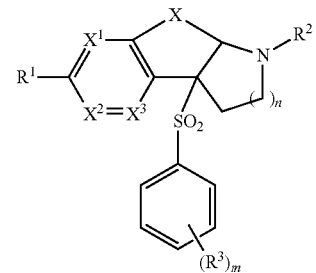

wherein

X is —CR$^4$R$^5$—, —(CR$^4$R$^5$)$_2$—, —OCR$^6$R$^7$—, —S(O)$_p$CR$^6$R$^7$—, —S(O)(NR$^g$)CR$^6$R$^7$— or —NR$^6$CR$^6$R$^7$—;

X$^1$, X$^2$, and X$^3$ are, independently, selected from N or CR$^{1d}$, wherein at least of X$^1$, X$^2$, and X$^3$ is N;

R$^1$ is selected from halo, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is selected from hydrogen, CN, —(CR$^{2e}$R$^{2f}$)$_r$—C(O)R$^{2d}$, —(CR$^{2e}$R$^{2f}$)$_r$—C(O)OR$^{2b}$, —(CR$^{2e}$R$^{2f}$)$_r$—C(O)NR$^{11}$R$^{11}$, —(CR$^{2e}$R$^{21}$)$_r$—S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)$_r$-3-10 membered carbocycle substituted with 0-4 R$^a$, and —(CR$^{2e}$R$^{2f}$)$_r$-4-7 membered heterocycle comprising carbon atoms, and 1-4 heteroatoms selected from N, O, P(O), S(O)$_p$ and S(O)(NR$^g$), substituted with 0-4 R$^a$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)$_r$—C$_{3-10}$ cycloalkyl substituted with 0-3 R$^d$, where the cycloalkyl ring may be fused, bridged or spirocyclic, —(CR$^{2e}$R$^{2f}$)$_r$-phenyl substituted with 0-2 R$^a$, or a —(CR$^{2e}$R$^{2f}$)$_r$-4-10 membered heterocycle where the heterocycle may be fused, bridged or spirocyclic, containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C (O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^c$, —(CR$^{1b}$R$^{1c}$)$_r$—C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^c$)$_r$—C(O)R$^b$, —(CR$^{1b}$R$^{1c}$)$_r$—C(O)OR$^b$, —(CR$^{1b}$R$^c$)$_r$—C(O)NR$^{11}$R$^{11}$, —(CR$^{1b}$R$^{1c}$)$_r$-3-14 membered carbocycle, or —(CR$^{1b}$R$^c$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;

n is 0, 1 or 2;

p and q are, independently at each occurrence, 0, 1, or 2; and r is 0, 1, 2, 3, or 4;

or a stereoisomer or pharmaceutically-acceptable salt thereof.

5. A compound according to claim 4 of the formula

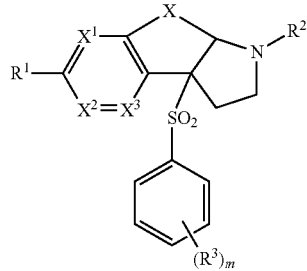

or a stereoisomer or pharmaceutically-acceptable salt thereof.

6. A compound according to claim 5 of the formula

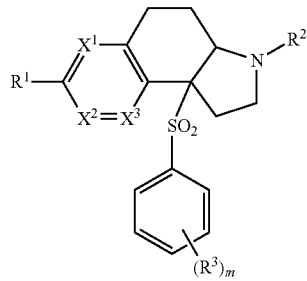

or a stereoisomer or pharmaceutically-acceptable salt thereof.

7. A compound according to claim 5 of the formula

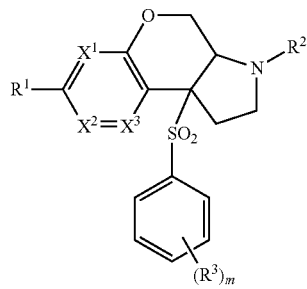

or a stereoisomer or pharmaceutically-acceptable salt thereof.

8. A compound according to claim 5 of the formula

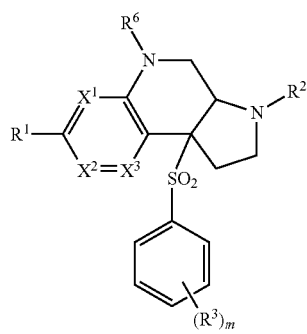

or a stereoisomer or pharmaceutically-acceptable salt thereof.

9. A compound according to claim 6 wherein
$X^1$, $X^2$ and $X^3$ are, independently, selected from N or CH;
$R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;
$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;
$R^{1b}$ and $R^{1c}$ are, independently at each occurrence, hydrogen, halogen or $C_{1-6}$ alkyl;
$R^{1d}$ is, independently at each occurrence, hydrogen, $CD_3$, halo, $CF_3$, and $C_1$-$C_4$ alkyl;
$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;
$R^{2a}$ is, independently at each occurrence, hydrogen or $C_{1-6}$ alkyl substituted with 0-3 $R^a$;
$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;
$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;
$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;
$R^3$ is, independently at each occurrence, hydrogen, halo, $N_3$, CN, $OR^{3b}$, —$NH_2$, —$NH(C_{1-6}$ alkyl), $N(C_{1-6}$ alkyl)$_2$, $C_{1-6}$ alkyl substituted with 0-3 $R^{3a}$, or $C_{3-10}$ cycloalkyl substituted with 0-3 $R^{3a}$;
$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, $NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and
$R^{3b}$ is, independently at each occurrence, hydrogen, $C_{1-6}$ alkyl substituted with 0-3 $R^a$ or phenyl substituted with 0-3 $R^a$;
or a stereoisomer or pharmaceutically-acceptable salt thereof.

10. A compound according to claim 7 wherein
$X^1$, $X^2$ and $X^3$ are, independently, selected from N or CH;
$R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;
$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;
$R^{1b}$ and $R^{1c}$ are, independently at each occurrence, hydrogen, halogen or $C_{1-6}$ alkyl;
$R^{1d}$ is, independently at each occurrence, hydrogen, $CD_3$, halo, $CF_3$, and $C_1$-$C_4$ alkyl;
$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;
$R^{2a}$ is, independently at each occurrence, hydrogen or $C_{1-6}$ alkyl substituted with 0-3 $R^a$;
$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;
$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;
$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;
$R^3$ is, independently at each occurrence, hydrogen, halo, $N_3$, CN, $OR^{3b}$, —$NH_2$, —$NH(C_{1-6}$ alkyl), $N(C_{1-6}$ alkyl)$_2$, $C_{1-6}$ alkyl substituted with 0-3 $R^{3a}$, or $C_{3-10}$ cycloalkyl substituted with 0-3 $R^{3a}$;
$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and
$R^{3b}$ is, independently at each occurrence, hydrogen, $C_{1-6}$ alkyl substituted with 0-3 $R^a$ or phenyl substituted with 0-3 $R^a$;
or a stereoisomer or pharmaceutically-acceptable salt thereof.

11. A compound according to claim 9 wherein
one of $X^1$, $X^2$ and $X^3$ is N, and the other two of $X^1$, $X^2$ and $X^3$ are CH;
$R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2d}$, —$C(O)NR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2d}$ is hydrogen, $C_{1-6}$ alkyl substituted with 0-2 $R^d$, $C_{1-6}$ haloalkyl, $C(O)NR^{11}R^{11}$, $C_{3-10}$ cycloalkyl substituted with 0-2 $R^d$, —$(CR^{2e}R^{2f})_r$-phenyl substituted with 0-2 $R^a$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl$)_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, $NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

12. A compound according to claim 10 wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$ or O—$C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —$C(O)OR^{2b}$, —$C(O)R^{2d}$, —$C(O)NR^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

13. A compound according to claim 11 wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —$C(O)OR^{2b}$, —$C(O)R^{2d}$, —$C(O)NR^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

14. A compound according to claim 12 wherein
one of $X^1$, $X^2$ and $X^3$ is N, and the other two of $X^1$, $X^2$ and $X^3$ are CH;

$R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^2$ is $C_{1-6}$ alkyl substituted with 0-3 $R^{2a}$, —$C(O)OR^{2b}$, —$C(O)R^{2d}$, —$C(O)NR^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2d}$ is $C_{3-10}$ cycloalkyl substituted with 0-2 $R^d$, or a 4-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, cyclopropyl or $C_{1-6}$ alkyl;

or a stereoisomer or pharmaceutically acceptable salt thereof.

15. A compound according to claim 13 wherein $R^2$ is
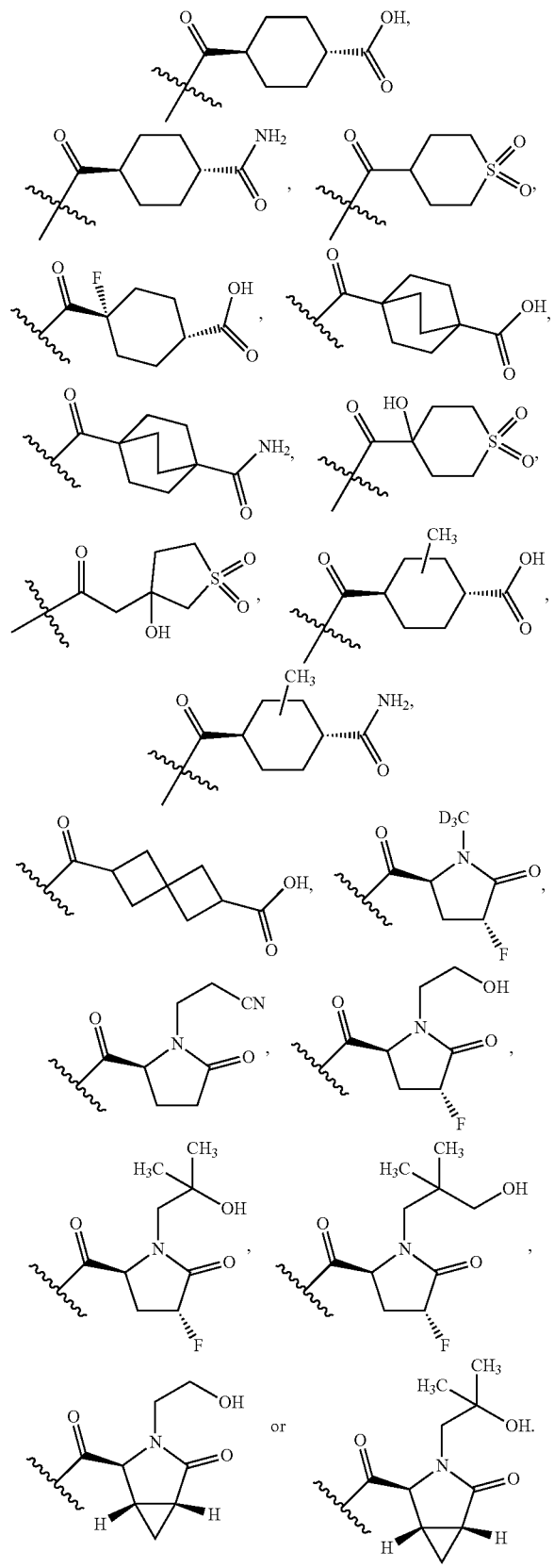
16. A compound according to claim 14 wherein $R^2$ is
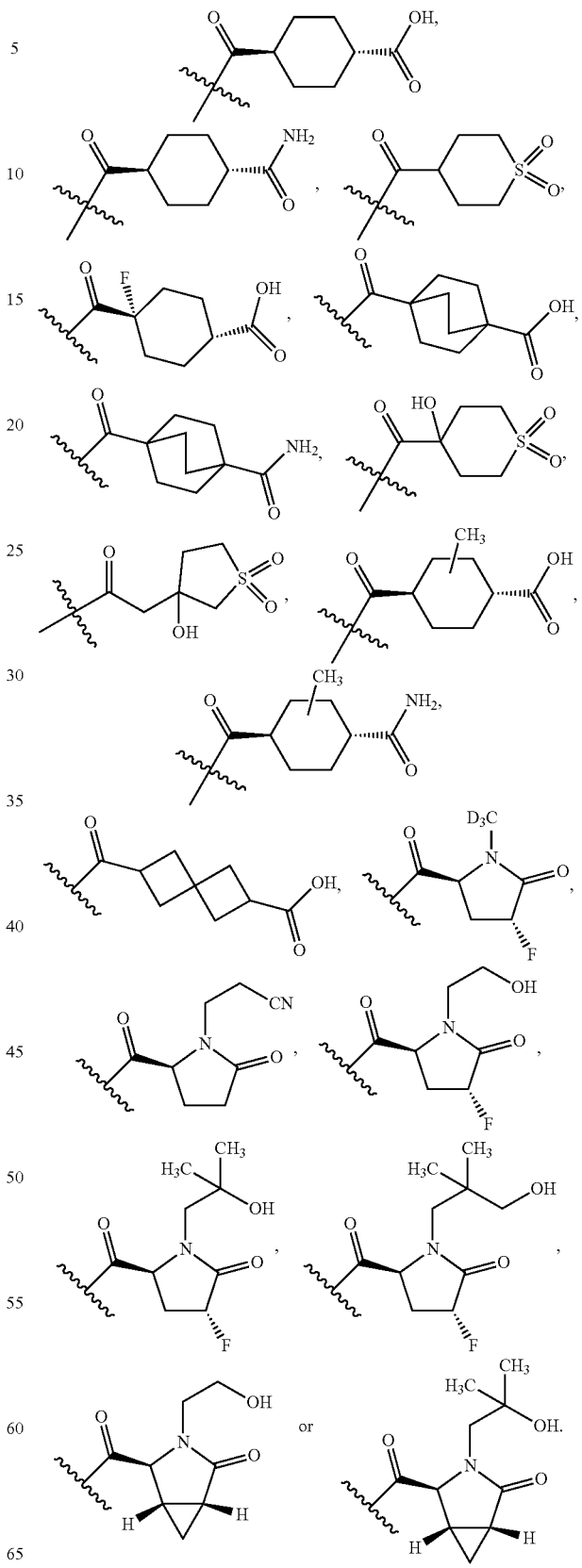

17. A compound selected from the following 3-((2S)-2-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-5-oxopyrrolidin-1-yl)propanenitrile (single enantiomer), (3R,5S)-3-fluoro-5-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-1-(methyl-d3)pyrrolidin-2-one trifluoroacetate (single enantiomer), (3R,5S)-3-fluoro-5-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-1-(methyl-d3)pyrrolidin-2-one (single enantiomer), (1r,4r)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)cyclohexane-1-carboxylic acid (single enantiomer), (1r,4r)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)cyclohexane-1-carboxamide (single enantiomer), 4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)bicyclo[2.2.2]octane-1-carboxylic acid hydrochloride (single enantiomer), 4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)bicyclo[2.2.2]octane-1-carboxamide (single enantiomer), (1,1-dioxidotetrahydro-2H-thiopyran-4-yl)(9a-((4-fluorophenyl)sulfonyl)-3-(perfluoropropan-2-yl)-5,6,6a,8,9,9a-hexahydro-7H-pyrrolo[2,3-h]quinolin-7-yl)methanone (single enantiomer), 6-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)spiro[3.3]heptane-2-carboxylic acid (mixture of two diastereomers), 1-(9b-((4-fluorophenyl)sulfonyl)-7-(perfluoropropan-2-yl)-1,2,3a,4,5,9b-hexahydro-3H-pyrrolo[3,2-f]quinolin-3-yl)-2-(3-hydroxy-1,1-dioxidotetrahydrothiophen-3-yl)ethan-1-one (mixture of two diastereomers), 2-(3-hydroxy-1,1-dioxidotetrahydrothiophen-3-yl)-1-(7-(perfluoropropan-2-yl)-9b-(phenylsulfonyl)-1,2,3a,4,5,9b-hexahydro-3H-pyrrolo[3,2-f]quinolin-3-yl)ethan-1-one trifluoroacetate (mixture of two diastereomers), (1,1-dioxidotetrahydro-2H-thiopyran-4-yl)(7-(perfluoropropan-2-yl)-9b-(phenylsulfonyl)-1,2,3a,4,5,9b-hexahydro-3H-pyrrolo[3,2-f]quinolin-3-yl)methanone (single enantiomer), (1,1-dioxidotetrahydro-2H-thiopyran-4-yl)(9a-((4-fluorophenyl)sulfonyl)-3-(perfluoropropan-2-yl)-5,6,6a,8,9,9a-hexahydro-7H-pyrrolo[2,3-h]isoquinolin-7-yl)methanone trifluoroacetate (single enantiomer), 3-((2S)-2-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)-5-oxopyrrolidin-1-yl)propanenitrile trifluoroacetate (single enantiomer), (1,1-dioxidotetrahydro-2H-thiopyran-4-yl)(9a-((3-fluorophenyl)sulfonyl)-3-(perfluoropropan-2-yl)-5,6,6a,8,9,9a-hexahydro-7H-pyrrolo[2,3-h]isoquinolin-7-yl)methanone trifluoroacetate (single enantiomer), 4-(7-(perfluoropropan-2-yl)-9b-(phenylsulfonyl)-2,3,3a,4,5,9b-hexahydro-1H-pyrrolo[3,2-f]quinoline-3-carbonyl)bicyclo[2.2.2]octane-1-carboxylic acid (single enantiomer), 2-hydroxy-2-methyl-1-(7-(perfluoropropan-2-yl)-9b-(phenylsulfonyl)-1,2,3a,4,5,9b-hexahydro-3H-pyrrolo[3,2-f]quinolin-3-yl)propan-1-one trifluoroacetate (single enantiomer), 3-hydroxy-3-methyl-1-(7-(perfluoropropan-2-yl)-9b-(phenylsulfonyl)-1,2,3a,4,5,9b-hexahydro-3H-pyrrolo[3,2-f]quinolin-3-yl)butan-1-one trifluoroacetate (single enantiomer), 3-((5S)-2-oxo-5-(7-(perfluoropropan-2-yl)-9b-(phenylsulfonyl)-2,3,3a,4,5,9b-hexahydro-1H-pyrrolo[3,2-f]quinoline-3-carbonyl)pyrrolidin-1-yl)propanenitrile trifluoroacetate (single enantiomer), (1,1-dioxidotetrahydro-2H-thiopyran-4-yl)(9b-((4-fluorophenyl)sulfonyl)-7-(perfluoropropan-2-yl)-1,2,3a,4,5,9b-hexahydro-3H-pyrrolo[3,2-f]quinolin-3-yl)methanone trifluoroacetate (single enantiomer), 3-((2S)-2-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-5-oxopyrrolidin-1-yl)propanenitrile trifluoroacetate (single enantiomer), (1,1-dioxidotetrahydro-2H-thiopyran-4-yl)(9b-((3-fluorophenyl)sulfonyl)-7-(perfluoropropan-2-yl)-1,2,3a,4,5,9b-hexahydro-3H-pyrrolo[3,2-f]quinolin-3-yl)methanone trifluoroacetate (single enantiomer), (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxylic acid trifluoroacetate (single enantiomer), (1r,4r)-4-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)cyclohexane-1-carboxylic acid (single enantiomer), (1R,3S,4R)-4-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-3-methylcyclohexane-1-carboxylic acid (single enantiomer), (1r,4r)-4-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)cyclohexane-1-carboxylic acid (single enantiomer), (1R,3S,4R)-4-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)-3-methylcyclohexane-1-carboxylic acid (single enantiomer), (1r,4r)-4-(7-(perfluoropropan-2-yl)-9b-(phenylsulfonyl)-2,3,3a,4,5,9b-hexahydro-1H-pyrrolo[3,2-f]quinoline-3-carbonyl)cyclohexane-1-carboxylic acid (single enantiomer), (1R,3S,4R)-3-methyl-4-(7-(perfluoropropan-2-yl)-9b-(phenylsulfonyl)-2,3,3a,4,5,9b-hexahydro-1H-pyrrolo[3,2-f]quinoline-3-carbonyl)cyclohexane-1-carboxylic acid (single enantiomer), (1R,3S,4R)-4-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-3-methylcyclohexane-1-carboxylic acid (single enantiomer), (1r,4r)-4-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)cyclohexane-1-carboxylic acid (single enantiomer), (1R,3S,4R)-4-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-3-methylcyclohexane-1-carboxylic acid (single enantiomer), (1r,4r)-4-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)cyclohexane-1-carboxylic acid (single enantiomer), (1R,4S,5S)-4-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-3-azabicyclo[3.1.0]hexan-2-one trifluoroacetate (single enantiomer), (3R,5S)-3-fluoro-5-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-1-(2-hydroxyethyl)pyrrolidin-2-one (single enantiomer), (3R,5S)-3-fluoro-5-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-1-(3-hydroxy-2,2-dimethylpropyl)pyrrolidin-2-one (single enantiomer), 3-((2S)-2-(7-((2,6-dichlorobenzyl)oxy)-9b-((4-fluorophenyl)sulfonyl)-2,3,3a,4,5,9b-hexahydro-1H-pyrrolo[3,2-f]quinoline-3-carbonyl)-5-oxopyrrolidin-1-yl)propanenitrile (single enantiomer), (1r,4r)-4-(7-((2,6-dichlorobenzyl)oxy)-9b-((4-fluorophenyl)sulfonyl)-2,3,3a,4,5,9b-hexahydro-1H-pyrrolo[3,2-f]quinoline-3-carbonyl)cyclohexane-1-carboxylic acid (single enantiomer), 3-((2S)-2-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-5-oxopyrrolidin-1-yl)propanenitrile (single enantiomer), 3-((2S)-2-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-5-oxopyrrolidin-1-yl)propanenitrile (single enantiomer), (3R,5S)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer), (3R,5R)-3-fluoro-5-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer), (3R,5R)-3-fluoro-5-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-1-(2-hydroxy-2-methylpropyl)pyrrolidin-2-one (single enantiomer), (3R,5R)-3-fluoro-5-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer), (3R,5S)-3-fluoro-5-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-1-(2-hydroxy-2-methylpropyl)pyrrolidin-2-one (single enantiomer), (3R,5S)-3-fluoro-5-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-1-(2-hydroxy-2-methylpropyl)pyrrolidin-2-one (single enantiomer), (1R,4S,5S)-4-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-3-(2-hydroxy-2-methylpropyl)-3-azabicyclo[3.1.0]hexan-2-one trifluoroacetate (single enantiomer), (3R,5S)-3-fluoro-5-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)-1-(2-hydroxy-2-methylpropyl)pyrrolidin-2-one trifluoroacetate (single enantiomer), (1R,4S,5S)-4-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)-3-(2-hydroxy-2-methylpropyl)-3-azabicyclo[3.1.0]hexan-2-one (single enantiomer), (3R,5S)-3-fluoro-1-(2-hydroxy-2-methylpropyl)-5-(7-(perfluoropropan-2-yl)-9b-(phenylsulfonyl)-2,3,3a,4,5,9b-hexahydro-1H-pyrrolo[3,2-f]quinoline-3-carbonyl)pyrrolidin-2-one (single enantiomer), 1-(9b-((4-fluorophenyl)sulfonyl)-7-(perfluoropropan-2-yl)-2,3,3a,4,5,9b-hexahydro-1H-pyrrolo[3,2-f]quinoline-3-carbonyl)-2-(2-hydroxy-2-methylpropyl)pyrazolidin-3-one (single enantiomer), 1-(9a-((4-fluorophenyl)sulfonyl)-3-(perfluoropropan-2-yl)-6,6a,7,8,9,9a-hexahydro-5H-pyrrolo[2,3-h]isoquinoline-7-carbonyl)-2-(2-hydroxy-2-methylpropyl)pyrazolidin-3-one (single enantiomer), 1-(9b-((3-fluorophenyl)sulfonyl)-7-(perfluoropropan-2-yl)-2,3,3a,4,5,9b-hexahydro-1H-pyrrolo[3,2-f]quinoline-3-carbonyl)-2-(2-hydroxy-2-methylpropyl)pyrazolidin-3-one (single enantiomer), 1-(9a-((3-fluorophenyl)sulfonyl)-3-(perfluoropropan-2-yl)-6,6a,7,8,9,9a-hexahydro-5H-pyrrolo[2,3-h]isoquinoline-7-carbonyl)-2-(2-hydroxy-2-methylpropyl)pyrazolidin-3-one (single enantiomer), 2-(2-hydroxy-2-methylpropyl)-1-(7-(perfluoropropan-2-yl)-9b-(phenylsulfonyl)-2,3,3a,4,5,9b-hexahydro-1H-pyrrolo[3,2-f]quinoline-3-carbonyl)pyrazolidin-3-one (single enantiomer), (1R,3S,4R)-4-(9a-((4-fluorophenyl)sulfonyl)-3-(perfluoropropan-2-yl)-6,6a,7,8,9,9a-hexahydro-5H-pyrrolo[2,3-h]quinoline-7-carbonyl)-3-methylcyclohexane-1-carboxamide (single enantiomer), 2,2,2-trifluoro-1-(9a-((3-fluorophenyl)sulfonyl)-3-(perfluoropropan-2-yl)-5,6,6a,8,9,9a-hexahydro-7H-pyrrolo[2,3-h]isoquinolin-7-yl)ethan-1-one (single enantiomer), 1-(7-((2,6-dichlorobenzyl)oxy)-9b-(phenylsulfonyl)-1,2,3a,4,5,9b-hexahydro-3H-pyrrolo[3,2-f]quinolin-3-yl)-2,2,2-trifluoroethan-1-one, or a stereoisomer or pharmaceutically acceptable salt thereof.

18. A pharmaceutical composition comprising one or more compounds according to claim 1 and a pharmaceutically acceptable carrier or diluent.

19. A method of treating a disease or disorder selected from an autoimmune disease or disorder, and a metabolic disease or disorder, the method comprising administering to the subject a therapeutically-effective amount of a compound according to claim 1.

20. The method of claim 19 wherein the autoimmune disease or disorder is selected from psoriasis, rheumatoid arthritis, inflammatory bowel disease, Crohn's disease, ulcerative colitis, acute graft-versus-host disease, psoriatic arthritis, ankylosing spondylitis and multiple sclerosis.

* * * * *